United States Patent
Selifonov et al.

(10) Patent No.: US 8,969,559 B2
(45) Date of Patent: Mar. 3, 2015

(54) KETAL AMIDE COMPOUNDS, METHODS OF MAKING, AND APPLICATIONS

(75) Inventors: Sergey Selifonov, Plymouth, MN (US); Adam E. Goetz, Los Angeles, CA (US); Marc D. Scholten, Saint Paul, MN (US); Ning Zhou, Saint Paul, MN (US)

(73) Assignee: Segetis, Inc., Golden Valley, MN (US)

( * ) Notice: Subject to any disclaimer, the term of this patent is extended or adjusted under 35 U.S.C. 154(b) by 0 days.

(21) Appl. No.: 13/370,860

(22) Filed: Feb. 10, 2012
(Under 37 CFR 1.47)

(65) Prior Publication Data

US 2013/0053564 A1 Feb. 28, 2013

Related U.S. Application Data

(63) Continuation of application No. 13/141,183, filed as application No. PCT/US2009/069101 on Dec. 22, 2009, now abandoned.

(60) Provisional application No. 61/140,137, filed on Dec. 23, 2008.

(51) Int. Cl.
| | | |
|---|---|---|
| *C07D 317/30* | (2006.01) | |
| *C07D 407/12* | (2006.01) | |
| *C07D 407/14* | (2006.01) | |
| *C07D 405/14* | (2006.01) | |

(52) U.S. Cl.
CPC .................................. *C07D 317/30* (2013.01)
USPC ........................... 544/374; 549/370; 549/452

(58) Field of Classification Search
None
See application file for complete search history.

(56) References Cited

U.S. PATENT DOCUMENTS 3,412,069 A    11/1968   Rice et al.

FOREIGN PATENT DOCUMENTS

| JP | 44-32435 | 12/1969 |
|---|---|---|
| WO | WO2004/099173 A1 | 11/2004 |
| WO | WO2007/062118 A2 | 5/2007 |
| WO | WO2008/124133 A1 | 10/2008 |
| WO | WO2009/032905 A1 | 3/2009 |
| WO | 2009049041 A2 | 4/2009 |

OTHER PUBLICATIONS

Lenz et al., caplus an 1970:122322.*
Lenz et al. 2, caplus an 1970:122322, RN 26968-23-0.*
Lenz et al., caplus an 1969:404033.*
International Search Report for PCT/US2009/069101, mailed Mar. 26, 2010, 2 pages.
Boseken, Felix, "Configuration of the pentaerythritol" Laboratory for Organ. Chem. of the Technical University, 1928 (received Feb. 28, 1928), p. 787-790. [Berichte der Deutschen Chemischen Gesellschaft B 1928, v.618B, pp. 787-790] English translation.
Lukes, Robert M., "Preparation of Methyl Esters Containing the 1,3-Dioxane or 2,4,8,10-Tetroxaspiro[5.5]undecane Structure by Ketal Exchange", J. Org. Chem., vol. 26. Jul. 1961 (received Sep. 6, 1960) p. 2515-2518.

* cited by examiner

*Primary Examiner* — Sun Jae Yoo
(74) *Attorney, Agent, or Firm* — Cantor Colburn LLP

(57) ABSTRACT

Disclosed herein are ketal amide compounds. The ketal amide compounds are synthesized by the reaction of ketal acids or ketal esters with amine functional compounds. Also disclosed are methodologies useful to make the ketal amide compounds. Also disclosed herein are formulations and articles containing the ketal amide compounds.

42 Claims, 10 Drawing Sheets

KETAL AMIDE COMPOUNDS, METHODS OF MAKING, AND APPLICATIONS

This application is being filed as a PCT International Patent application on Dec. 22, 2009 in the name of Segetis, Inc., a U.S. national corporation, applicant for the designation of all countries except the U.S., and Sergey Selifonov, a U.S. Citizen, Adam E. Goetz, a U.S. Citizen, Marc Sholten, a U.S. Citizen, and Ning Zhou, a citizen of China, applicants for the designation of the U.S. only, and claims priority to U.S. Patent Application Ser. No. 61/140,137, filed Dec. 23, 2008, the contents of which are herein incorporated by reference.

FIELD OF THE INVENTION

The invention relates to ketal amide functional compounds. The compounds are synthesized by the reaction of ketal acids or ketal esters with polyamines. The invention further relates methodology useful to make the ketal amide functional compounds. The invention further relates to applications of ketal amide functional compounds in various formulations and articles.

BACKGROUND

Many known chemical products such as surfactants, plasticizers, solvents, and polymers are currently manufactured from non-renewable, expensive, petroleum-derived or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods. Using renewable resources as feedstocks for chemical processes will reduce the demand on non-renewable fossil fuels currently used in the chemical industry and reduce the overall production of carbon dioxide, the most notable greenhouse gas.

A potential source of materials that are useful as chemical building blocks are cyclic ketals and acetals of oxocarboxylates with polyols. It is known, for example, that polyhydric alcohols, or polyols, having 1,2 and 1,3 hydroxy conformations can react with a ketone or aldehyde to form a cyclic ketal or an acetal (Carey, F. A. and Sundberg, R. J., "Advanced Organic Chemistry Part B: Reactions and Synthesis" $2^{nd}$ ed., © 1983, Plenum Press, NY, N.Y., p. 544). The 1,2 and 1,3 configurations of hydroxyl groups on a hydrocarbon chain are shown below as (a) and (b), respectively.

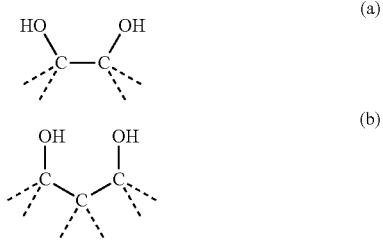

Diols such as 1,2-ethane diol (ethylene glycol) and 1,3 propanediol (propylene glycol) are examples of such polyols. Diols having a 1,2 hydroxyl group configuration will form dioxolanes when reacted with ketone or aldehyde moieties, while 1,3 diols will form dioxanes.

Ketal acids and esters are starting materials from which the compounds of the invention are synthesized. Ketals of glycerol and levulinic acid or an ester thereof are described in U.S. Patent Publication No. 2008/0242721, the entirety of which is incorporated herein by reference. The ketal reaction product of glycerol with a levulinate results in a monoketal acid or monoketal ester as shown below,

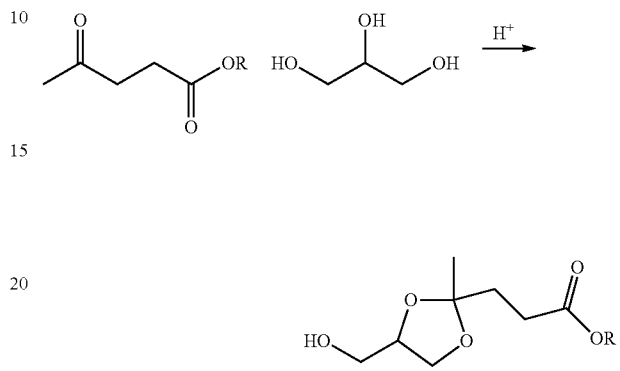

wherein R is hydrogen or an alkyl group. Combining a levulinate ester with glycerol provides a levulinate-glycerol ketal that is bifunctional and available from 100% renewable feedstocks. The levulinate-glycerol ketals are useful for synthesis of a wide variety of surfactants, plasticizers, polymers, and the like. Other monoketals synthesized from various oxocarboxylic acids or esters thereof such as acetoacetates and pyruvates, with triols such as 1,1,1-trimethylolpropane and 1,1,1-trimethylolethane, are described in International Patent Application No. PCT/US2008/075225. The monoketal acids and esters have the general structure

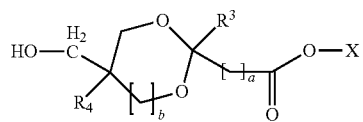

wherein a is 0 or 1, b is 0 or 1, $R_3$ is hydrogen or an alkyl group having between 1 and 12 carbons, $R_4$ is an alkyl group having between 1 and 12 carbons, and X is any substituent. Substituents $R_3$ and $R_4$ may further be substituted with one or more functional groups, such as halogen, ether, cyano, and the like. These materials are useful as, or for the synthesis of, a wide variety of surfactants, plasticizers, polymers, and the like. The compounds described in these applications are capable of self condensation to provide oligomers or polymers having hydroxyl endgroups, and further are capable of condensation with one or more diols to give oligomeric or polymeric polyols. Monoketals are starting materials for the synthesis of the compounds of the invention.

Polyketal acids and polyketal esters, which are compounds having at least two contiguous or semi-contiguous ketal acid or ketal ester moieties per molecule, are described in International Patent Application No. PCT/US2008/079337. Various oxocarboxylic acids and esters are useful in synthesizing the disclosed compounds, as well as various tetrols and higher polyols. In one nonlimiting example, combining a levulinate ester with erythritol provides a bisketal starting material from renewable feedstocks. This reaction is shown below,

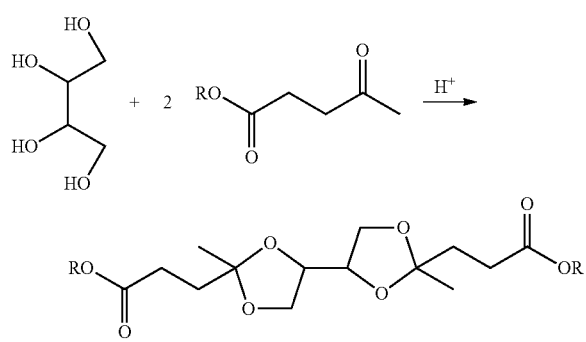

wherein R is hydrogen or an alkyl group. Further, the polyketal acids and esters are useful as, or for the synthesis of, a wide variety of surfactants, plasticizers, polymers, and the like, as disclosed in the application.

Efficient synthetic routes to form various compounds based on the ketals or acetals of oxocarboxylates are described in International Patent Application No. PCT/US08/79083. The synthetic routes described therein are useful as a basis for efficient reaction of a number of oxocarboxylic acids and esters thereof with diols, triols, and higher polyols and are useful in making any of the above mentioned ketal moieties, all of which are starting materials for the compounds of the invention.

SUMMARY

Disclosed herein are ketal amide compounds, which are cyclic ketals and acetals of oxocarboxamides. The compounds of the invention are, in some embodiments, synthesized by the reaction of diamines and higher polyamines with cyclic ketal and acetal acids, cyclic ketal and acetal esters, cyclic ketal and acetal polyesters, cyclic polyketal and polyacetal acids, cyclic polyketal and polyacetal esters, cyclic polyketal polyesters, and cyclic polyacetal polyesters. Polymeric and nonpolymeric compounds, as well as methods to make these compounds, are aspects of the invention.

The compounds of the invention are useful in a number of applications. Nonlimiting examples of uses for the compounds of the invention include plasticizers, surfactants, coalescing solvents, interfacial modifiers, and phase transfer materials in one or more formulations. Some of the ketal amide compounds of the invention are employed, in embodiments, as monomers in the synthesis of various polymers such as polyesters, polyisocyanates, polyurethanes, polyurethane urea)s, poly(ester urethane)s, polycarbonates, polyamides, and copolymers thereof. In other embodiments, the compounds of the invention are functionalized with acrylates, methacrylates, allyl or oxirane groups; these groups are, in embodiments, further reacted or polymerized. In some embodiments, the multiple functionalities of the compounds of the invention serve as crosslinking moieties for one or more polymeric networks.

In embodiments, the compounds of the invention are reacted to form a polymer having a substantial degree of polymerization, that is, a degree of polymerization of about 2 to 500, for example in some embodiments about 10 to 200, or about 10 to 100. Glass transition temperature of some of polymers of the invention is about 0° C. to 110° C., or about 5° C. to 80° C. In some embodiments, the polymers of the invention are ductile. The polymers of the invention are, in some embodiments, transparent to visible light and are light amber to orange in color. The polymers of the invention, in some embodiments, are hydrophilic and therefore compatible with damp surfaces, enabling certain applications of the polymers requiring adhesion to a damp, water-coated, or water-saturated surface.

One aspect of the invention is a novel aminolysis methodology. The methodology is based on use of an organic guanidine type catalyst that drives the polymerization of diesters and diamines to form polyamides at surprisingly low temperatures. Thus, compounds of the invention are employed in conjunction with the method of the invention to result in polyamides under mild conditions.

High polymers and crosslinked polymer networks containing one or more compounds of the invention are useful in a variety of applications. Due to superior properties such as high tensile strength and high glass transition temperatures, the polymeric compounds of the invention are well suited for many commercially valuable applications such as use in fibers for nonwoven or woven fabrics; formation of articles, such as structural members, having high strength; and many other applications that typically and advantageously employ polyamides such as Nylon 6, Nylon 6,6, and other related structures.

Additional advantages and novel features of the invention will be set forth in part in the description that follows, and in part will become apparent upon examination of the following, or may be learned through routine experimentation upon practice of the invention.

DETAILED DESCRIPTION

Figure 1A:
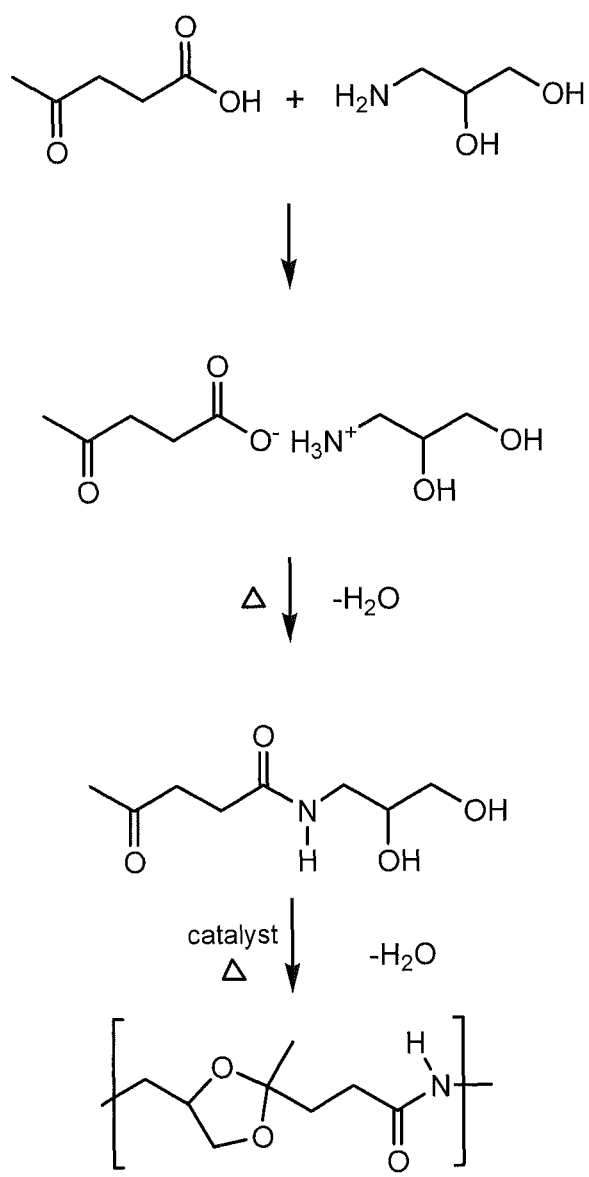
FIG. 1A-1D depict representative synthetic schemes and structures of the invention.

Various embodiments will be described in detail. Reference to various embodiments does not limit the scope of the claims attached hereto. Additionally, any examples set forth in this specification are not intended to be limiting and merely set forth some of the many possible embodiments for the appended claims.

The compounds of the invention have, in embodiments, one or more isomers. Where an isomer can exist, it should be understood that the invention embodies all isomers thereof, including stereoisomers, conformational isomers, and cis, trans isomers; isolated isomers thereof; and mixtures thereof. Structure I.

In some embodiments, the invention embodies compounds having Structure I:

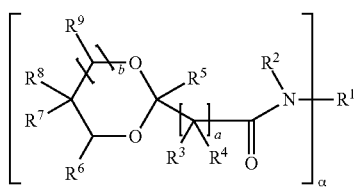

wherein

R¹ is a linear, branched, or cyclic alkyl, alkenyl, or alkynyl group, or an aryl or alkaryl group, or a polymeric group, wherein the alkyl, alkenyl, aryl, alkaryl, or polymeric groups can have one or more heteroatoms; or R¹ together with R² can form a cyclic structure that is the residue of a cyclic diamine, such as piperazine;

R² is hydrogen or an alkyl group having 1 to 6 carbon atoms, wherein each R² may be the same or different; or R² together with R¹ can form a cyclic structure that is the residue of a cyclic diamine, such as piperazine;

R³ and R⁴ are independently hydrogen, halogen, amine, mercapto, phosphate, phosphonooxy, silyl, siloxane, alkynyl, or a linear, branched, or cyclic alkyl or alkenyl groups having 1 to 18 carbon atoms, or an aryl or alkaryl group, wherein the alkyl, alkenyl, aryl, or alkaryl groups can have one or more heteroatoms, and wherein each R³ and R⁴ may be the same or different;

R⁵ is hydrogen, alkynyl, or a linear, branched, or cyclic alkyl or alkenyl group having 1 to 18 carbon atoms, or an aryl or alkaryl group, wherein the alkyl, alkenyl, aryl, or alkaryl groups can have one or more heteroatoms, and wherein each R⁵ may be the same or different;

R⁶, R⁸, and R⁹ are independently hydrogen, halogen, or an alkyl group having between 1 and 6 carbon atoms and optionally one or more heteroatoms, and wherein each R⁶, R⁸, and R⁹ may be the same or different;

R⁷ is —CH₂OH, —CH₂NH₂, —NH₂, —CH₂SH, —CH₂Br,

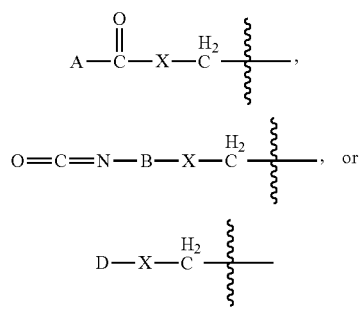

wherein A, B, and D are independently linear, branched, or cyclic alkyl, alkenyl, or alkynyl groups, or aryl or alkaryl groups, wherein the alkyl, alkenyl, alkynyl, aryl, or alkaryl groups have 1 to 36 carbon atoms and can further have one or more heteroatoms; and X is O, S, or NH; wherein each R⁷ may be the same or different;

a is 0 or an integer of between 1 and 12, and each a is the same or different;

b is 0 or 1, wherein b=0 indicates a five membered ring,

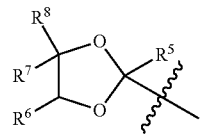

and b=1 indicates a 6 membered ring,

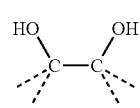

and b is the same or different for each occurrence; and

α is an integer of 1 or more.

"Heteroatoms" present in the one or more R¹, R³, R⁴, R⁵, R⁶, R⁷, R⁸, R⁹, or A groups of Structure I can include, for example, halogen, nitrogen, oxygen, sulfur, silicon, phosphorus, and the like and can be embodied in a functional group such as amino, carbonate, imide, amide, sulfone, sulfonamide, urethane, mercapto, disulfide, ether, ester, phosphate, phosphonooxy, silane, or silyl functional groups, or a combination thereof. The "polymeric group" of R¹ is not particularly limited and can be derived from, for example, a polyethylene having multiple amino residues, a poly(ethyleneimine), a polyoxyalkyleneamine, a branched polyurea having primary amide groups, or some other polymer. The polymeric group can have, in embodiments, a linear, branched, hyperbranched, or starburst morphology. The polymer can be, in embodiments, present as a surface, as a layer on top of a surface, or as a particle surface, a porous particle interior, and the like.

In some embodiments, the compounds of Structure I are made by the reaction of ketal esters with diamines or higher polyamines. The term "ketal ester" means the cyclic ketal or acetal of a keto acid, semialdehyde, or ester thereof. The ketal esters are, in embodiments, any of those disclosed in International Patent Application Nos. PCT/US08/075,225 or PCT/US08/79083, or U.S. Patent Publication No. 2008/0242721, which is incorporated herein by reference. In other embodiments, the ketal esters are made from oxocarboxylates as disclosed in the incorporated references and diols capable of forming cyclic ketals with ketone or aldehyde moieties. In general, such diols are those having 1,2 and 1,3 hydroxy conformations (Carey, F. A. and Sundberg, R. J., "Advanced Organic Chemistry Part B: Reactions and Synthesis" 2ⁿᵈ ed., © 1983, Plenum Press, NY, N.Y., p. 544). The 1,2 and 1,3 configurations of hydroxyl groups on a hydrocarbon chain are shown below as (a) and (b), respectively.

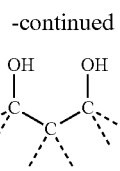
(b)

Diols such as 1,2-ethane diol and 1,3 propanediol are examples of such diols. Other suitable diols include any of those having (a) or (b) type configurations, such as for example 1,2-propanediol, 2,2-dimethyl-1,3-propanediol (neopentyl glycol), 3-aminopropane-1,2-diol (aminoglycerol), 3-sulfanylpropane-1,2-diol(thioglycerol), 1,4-bis-sulfanylbutane-2,3-diol (dithiothreitol), 1,2-butanediol, 1,3-butanediol, cyclohexane-1,2-diol, 1,4-dioxane-2,3-diol, 3-butene-1,2-diol, benzene-1,2-diol (catechol), 3-chlorocatechol, indane-1,2-diol, tartaric acid, and 2,3-dihydroxyisovaleric acid.

Employing a triol to form a ketal ester imparts, in some embodiments, a methylol (e.g. —CH$_2$OH) group to the resulting ketal ester. Trimethylolethane, trimethylolpropane, and glycerol are examples of triols that react with oxocarboxylates to form ketal esters having a methylol group adjacent to the ketal functionality. The methylol group remains intact when a diamine or higher polyamine is reacted with the ester group, providing two or more hydroxyl moieties in the resulting poly(ketal amide). In some embodiments, the triol employed in the reaction is glycerol. Glycerol is an inexpensive renewable compound that is readily available as a by-product of biodiesel production or via fermentation of carbohydrates. Since glycerol forms the backbone of triglycerides, it is produced upon saponification or transesterification of these compounds. Soap-making and biodiesel production are respective examples. Glycerol is a roughly 10% by-product of biodiesel manufacture, via transesterification of vegetable oils.

In some embodiments of Structure I, $R^1$ is —(CH$_2$)$_3$—. In other embodiments, $R^1$ is 1,2-cyclohexyl. In still other embodiments, $R^1$ is —(CH$_2$)$_6$—. In some embodiments, a is 0, 1, or 2. In other embodiments, the value of a is 2 and all $R^3$ and $R^4$ are hydrogen. In embodiments, $R^5$ is methyl. In embodiments, b is 0 and $R^6$ and $R^8$ are hydrogen.

In some embodiments, the compounds of Structure I are formed from the reaction of a diamine or higher polyamine with the ketal formed from pyruvic acid (a=0), acetoacetic acid (a=1, $R^3$, $R^4$=H), or levulinic acid (a=2, all $R^3$, $R^4$=H) or an ester thereof with glycerol (b=0, $R^7$=CH$_2$OH, $R^6$, $R^8$=H), 1,1,1-trimethylolpropane (b=1, $R^7$=—CH$_2$OH, $R^8$=CH$_2$CH$_3$, $R^6$, $R^9$=H), or 1,1,1-trimethylolethane (b=1, $R^7$=—CH$_2$OH, $R^8$=CH$_3$, $R^6$, $R^9$=H). Levulinic acid is an abundant feedstock that is prepared on an industrial scale by acidic degradation of hexoses and hexose-containing polysaccharides such as cellulose, starch, sucrose, and the like.

Suitable diamines and higher polyamines that are, in embodiments, reacted with a ketal acid or ester to form the poly(ketal amide)s of Structure I include hydrazine, ethane-1,2-diamine, 1,6-hexanediamine, but-2-ene-1,4-diamine, Metformin, butane-1,4-diamine, propane-1,2-diamine, piperazine, 2,2,4-trimethyl-1,6-hexanediamine, 2,4,4-trimethyl-1,6-hexanediamine, benzene-1,3-diamine, 2-methylbenzene-1,3-diamine, 4-chlorobenzene-1,3-diamine, methanediamine, 1,3,5-triazine-2,4,6-triamine, N-(2-aminoethyl)ethane-1,2-diamine, N-(6-aminohexyl)hexane-1,6-diamine, N,N'-bis(2-aminoethyl)ethane-1,2-diamine, N-[2-(3-aminopropylamino)ethyl]propane-1,3-diamine, 4-(3,4-diaminophenyl)benzene-1,2-diamine, spermine (N,N'-bis(3-aminopropyl)butane-1,4-diamine), diethylene triamine, dipropylene triamine, dihexylene triamine, 1,2,4-triazole-3,4,5-triamine, 2,4,5-triaminotoluene, melamine (1,3,5-triazine-2,4,6-triamine), benzene-1,3,5-triamine, triethylene tetramine, norspermine, N-[2-(3-aminopropylamino)ethyl]propane-1,3-diamine, 4-(3,4-diaminophenyl)benzene-1,2-diamine, a polyethyleneimine, a polyoxyalkyleneamine having two or more amine groups, such as those sold under the trade name JEFFAMINE® (available from the Huntsman Corp. of Salt Lake City, Utah), or any diamine or higher amine compound such as those sold under the trade name ELASTAMINE® (available from the Huntsman Corporation).

The compounds of Structure I are not particularly limited as to the method employed to make them; in general, any of the known methods of forming an amide from a carboxylic acid or ester thereof may be employed to synthesize a compound having Structure I from a ketal acid or ester thereof and a diamine or higher polyamine. In some embodiments, a ketal acid or ketal ester and a polyamine are simply mixed together and heated to a temperature of about 150° C. to 250° C., or about 180° C. to 210° C. to affect the reaction to form the compounds of Structure I. In some such embodiments, water or alcohol evolved during the course of the reaction is removed. In some embodiments, catalysts are employed in the synthesis of the compounds of Structure I. For example, titanium alkoxides such as titanium (IV) butoxide or titanium (IV) isopropoxide are employed in some embodiments to catalyze the reaction. In other embodiments, a Lewis acid catalyst such as antimony trichloride, aluminum chloride, antimony trifluoride, ferric chloride, antimony pentachloride, niobium pentachloride, tantalum tetrachloride, titanium tetrachloride, boron trifluoride, antimony pentafluoride, stannic fluoride, aluminum bromide, thallium trichloride, uranyl nitrate, uranium tetrachloride, uranyl acetate, uranium oxides such as UO$_2$, and the like are employed in the synthesis of the compounds of Structure I. In embodiments where a catalyst is employed, the reaction proceeds at temperatures as low as about 200° C., or between about 80° C. and 200° C., or even as low as about 80° C. to 180° C.

In another method that is employed, in embodiments, to synthesize the compounds of Structure I, an oxocarboxylate is first reacted with a diamine or higher polyamine to form a bisamide, trisamide, or higher amide functional intermediate compound. The amide functional intermediate compound is then reacted with a diol such as those disclosed above, or a triol or higher polyol such as those disclosed in International Patent Application Nos. PCT/US08/075,225 or PCT/US08/79083, or U.S. Patent Publication No. 2008/0242721, to form the ketal moiety. For example, where the diol used to form the ketal is 1-aminoglycerol, it is advantageous in some embodiments to first employ a polyamine to form an amide functional intermediate, then employ the aminoglycerol to form the ketal functionality, because it avoids a side reaction between aminoglycerol and the carboxyl moiety of the oxocarboxylate.

Some representative compounds having Structure I and made from of ketal esters of pyruvic acid, acetoacetic acid, or levulinic acid with glycerol, aminoglycerol, or trimethylolpropane and further reacted with diamines or triamines are shown below as Ia-Ic; it will be understood that these representative examples are not limiting to the overall body of compounds encompassed by Structure I but rather are intended to illustrate the breadth of structures available.

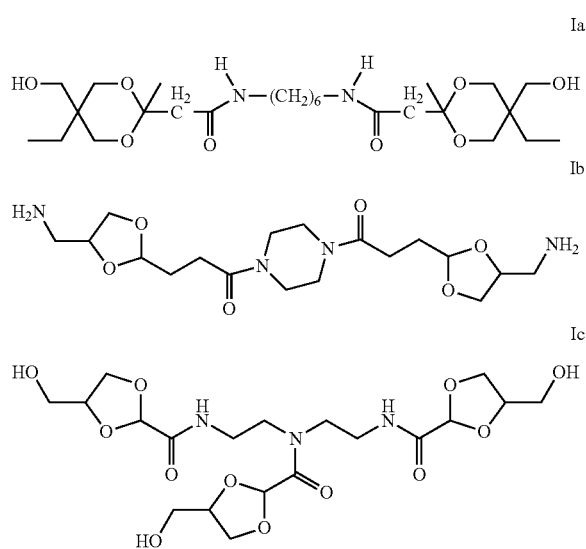

Structure I, Embodiment 1.

Where $R^7$ of Structure I is amino (—NH$_2$), methylol (—CH$_2$OH), methylamino (—CH$_2$NH$_2$), or methylthio (—CH$_2$SH), the compounds of Structure I are, in some embodiments, soluble in water and lower alcohols and hydrophilic coating formulations. In other embodiments, for example wherein $R^7$ is amino, methylol, methylamino, or methylthio; and $R^1$ is a long chain alkyl group, for example dodecyl, the compounds of Structure I are soluble in hydrophobic formulations. In yet other embodiments where $R^7$ is amino, methylol, methylamino, or methylthio, the various other R groups of Structure I determine solubility in one or more formulations; in some such embodiments, the compounds of Structure I are surfactants, solubilizers, interfacial modifiers, and the like.

For the purposes of the invention, compounds having Structure I wherein $R^7$ is methylol are referred to as "poly (ketal amide)ols." In similar embodiments, compounds of Structure I are, where $R^7$ is amino or methylamino are poly (ketal amide) amines; and where $R^7$ is methylthio, poly(ketal amide) thiols. Where α is 2, the compounds of Structure I are bisketal amide diols (or diamines or dithiols); where α is 3, the compounds of Structure I are trisketal amide triols (or triamines or trithiols); and so on. Such poly(ketal amide)s having two or more reactive hydrogen atoms have synthetic applicability to a wide variety of polymeric structures. In embodiments where $R^7$ is described as methylol, it will be understood for the purposes of the discussion that follows that in many embodiments the methylol group can be replaced with amino, methylamino, or methylthiol to provide compounds of similar reactivity in the corresponding structure formation and/or utility in the corresponding formulation.

The various compounds of Structure I, Embodiment 1 are useful for incorporation into various formulations. For example, where the compounds are hydrophilic, they are useful as incorporated into coating formulations such as concrete coatings, floor coatings, and other coatings designed for damp substrates. Due to the hydrophilicity of some compounds of Structure I, Embodiment 1, they are miscible in waterborne and other hydrophilic coating formulations, and provide a compound of substantial molecular weight; this in turn allows the compounds, in some embodiments, to act as a coalescing solvent as the coating dries; in other embodiments, these compounds provide a means for such coatings to gain better adhesion to the desired substrate by increasing compatibility between the coating and the substrate or by some other means. In other embodiments, the poly(ketal amide)ols, the poly(ketal amide)amines, and the poly(ketal amide)thiols are useful as nucleating agents for polymers in the solid state. For example, it is known that polylactide polymers are nucleated by bisamides to induce crystal formation; see, for example, Nishimura et al., U.S. Patent Publication No. 2005/0165142, Tweed et al., U.S. Patent Publication No. 2007/0116909, and McDaniel, U.S. Patent Publication No. 2007/0003774; poly-α-olefins such as poly(1-butene) are also nucleated by bisamide compounds; see, for example, Chatterjee, U.S. Pat. Nos. 4,645,792 and 4,322,503. The compounds of Structure I, Embodiment 1 are, in some embodiments, similarly useful as nucleating agents for one or more polymers that may be polylactide polymers, poly-α-olefins, or various other polymer structures.

Structure I, Embodiment 1A.

Where a of Structure I is 1 and $R^7$ is NH$_2$ or —CH$_2$NH$_2$, homopolymerization of the compound of Structure I leads, in embodiments, to a compound having a structure

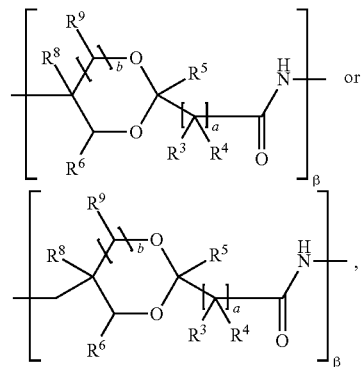

respectively. Such polymeric structures are obtained, in embodiments, by reacting an oxocarboxylic acid with 1-amino-2,3-propanediol or 2-amino-1,3-propanediol (collectively, "aminoglycerols") to result in the ammonium salt, followed by heating to form the amide; heat or catalysis or both would then result in homopolymerization via ketalization. This reaction scheme is shown in FIG. 1A.

The method is carried out, in embodiments of the invention, by starting with a precursor oxocarboxylate having free acid groups, for example pyruvic acid, acetoacetic acid, or levulinic acid. A stoichiometric balance of a precursor oxocarboxylic acid and an aminoglycerol is achieved by forming the 1:1 ammonium salt in aqueous solution of about 10% to 80%, or about 50%, by weight of the combined compounds in water. Stoichiometry is achieved by controlling the pH of the solution by addition of the oxocarboxylic acid to lower the pH, or addition of the aminoglycerol to raise the pH. Subsequent concentration of the salt to a slurry of about 60% by weight or greater is then achieved, in embodiments, by removing some of the water at a temperature of about 100° C. or greater. Concentration is followed by amide formation by heating the concentrated slurry to a temperature greater than 100° C., in embodiments as high as 200° C. or even 250° C. to remove water and form the amide bond. In some embodiments, a pressure of about 1.7 MPa or greater is employed during part of all of the amide formation by allowing escape of water. In some embodiments, no additional catalyst is required to form the amide from the ammonium salt.

After the amide is formed, homopolymerization is carried out under relatively mild conditions by employing a catalyst and heating the reaction to a temperature sufficient to cause ketalization and remove water. The catalyst employed may be a Lewis or Brønsted acid and the conditions and catalyst used to cause polyketalization are the same or similar, in some embodiments, to the methods employed to synthesize ketal esters as described in either U.S. Patent Application No. 2008/0242721, which is incorporated by reference in its entirety herein, or International Patent Application No. PCT/US08/79083.

The compounds of Structure I, Embodiment 1A have unique and useful properties that enable their use in a wide range of applications. In various embodiments, the compounds of Structure I, Embodiment 1A have good transparency, high levels of stiffness, high levels of hardness, good creep resistance, good dimensional stability, little processing shrinkage, good heat distortion properties, high melt viscosity, high melt strength, ability to alloy with other polyamides that are amorphous or semicrystalline to achieve a wide additional range of properties, low water uptake, good surface properties, good barrier properties, resistance to nonpolar solvents, good impact strength, ductility at moderate temperatures, good weatherability, and stress-crack resistance to polar solvents.

Structure I, Embodiment 2.

Where $R^7$ of Structure I is

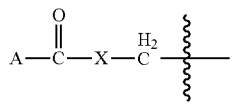

and A is a linear, branched, or cyclic alkyl, alkenyl, or alkynylgroup, or an aryl or alkaryl group, wherein the alkyl, alkenyl, alkynyl, aryl, or alkaryl group has 1 to 36 carbon atoms and can further have one or more heteroatoms; and X is O, S, or NH; the compounds are poly(ketal amide)esters, poly(ketal amide)amides, or poly(ketal amide)thioesters. The character of the A group is easily tailorable to impart the desired property, such as degree of hydrophobicity or hydrophilicity, melting point, and so forth to the compounds of Structure I.

Poly(ketal amide)esters, poly(ketal amide)amides, and poly(ketal amide)thioesters are obtained, in embodiments, by the reaction of, respectively, a poly(ketal amide)ol, poly(ketal amide)amine, or poly(ketal amide)thiol of Structure I, Embodiment 1 with one or more carboxylate compounds. The methylol, methylamino, or methylthio moieties of Structure I, Embodiment 1 have two or more reactive hydrogen atom sites that are available for reaction with, in various embodiments, carboxylic acids, carboxylic acid esters, carboxylic acid anhydrides, or carboxylic acid halides such as a carboxylic acid chloride. Such reactions are well known in the literature and any of the commonly employed methods to form carboxylates from hydroxyl groups, carboxamides from amine groups, or thioesters from mercapto groups are useful in one or more embodiments. Carboxylic acids, carboxylic acid esters, carboxylic acid anhydrides, or carboxylic acid halides useful in such reactions are, in various embodiments, any of the carboxylic acids, carboxylic acid esters, carboxylic acid anhydrides, or carboxylic acid halides found in the literature. Many structural variations of the poly(ketal amide) esters, poly(ketal amide)amides, or poly(ketal amide) thioesters of the invention are easily envisioned.

In one set of embodiments, a fatty acid ester is transesterified with a poly(ketal amide)ol, poly(ketal amide)amine, or poly(ketal amide)thiol of Structure I, Embodiment 1 to give the compounds of Structure I, Embodiment 2. In some such embodiments, the fatty acid ester is a mixture of unsaturated and saturated fatty acid esters. In some such embodiments, the mixture is predominantly unsaturated fatty acid ester. In some such embodiments, the mixture contains a triglyceride of a vegetable oil, such as soybean oil, linseed oil, canola oil, safflower oil, sunflower oil, corn oil, castor oil, or a blend thereof; soybean oil or canola oil are particularly useful. The mixture includes, in some embodiments, high oleic canola oil, an ester of 10-undecylenic acid, or a mixture of methyl esters of fatty acids derived from transesterification of a vegetable oil. In some embodiments, the fatty acid ester is an epoxidized unsaturated fatty acid ester; in some such embodiments the epoxide an unsaturated fatty acid ester is composed of a mixture of an unsaturated fatty acid ester and one or more saturated fatty acid esters. In some such embodiments, the epoxide of an unsaturated fatty acid ester contains at least one epoxidized double bond; in other embodiments, the epoxidized unsaturated fatty acid ester contains a majority of epoxidized double bonds. An unsaturated fatty acid ester is, in some embodiments, partially hydrogenated. In some embodiments, an unsaturated fatty acid ester is isomerized to change position or stereochemistry of the double bonds.

Figure 1B:
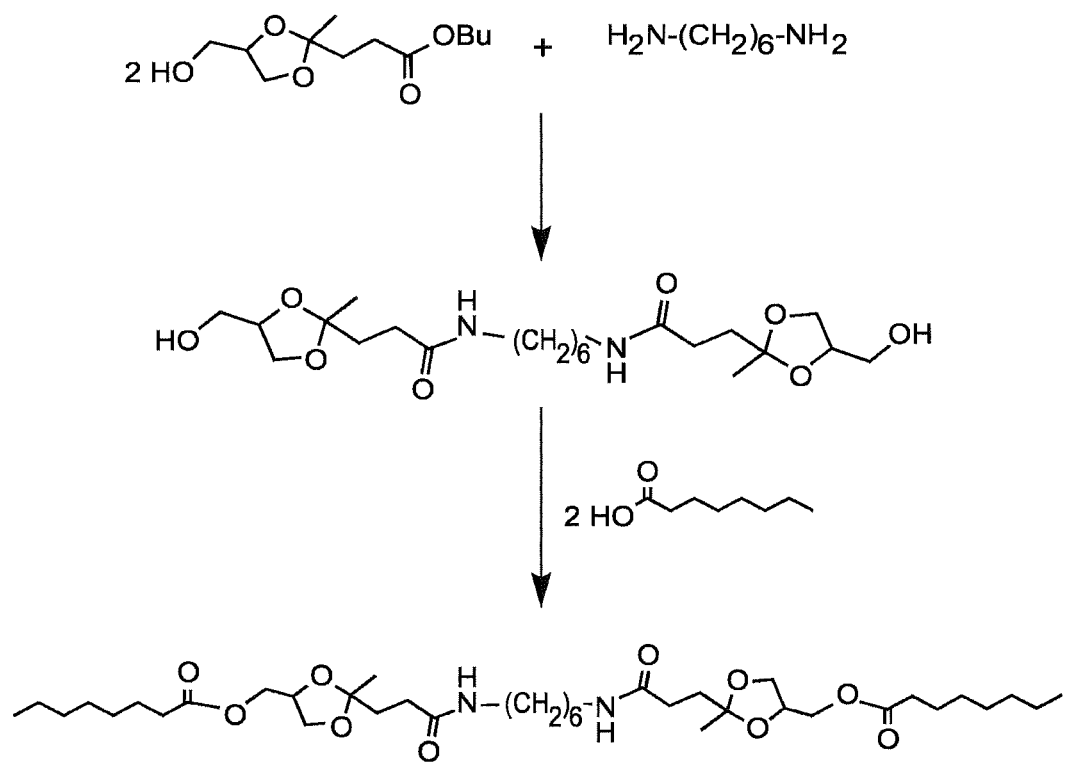
Figure 1C:
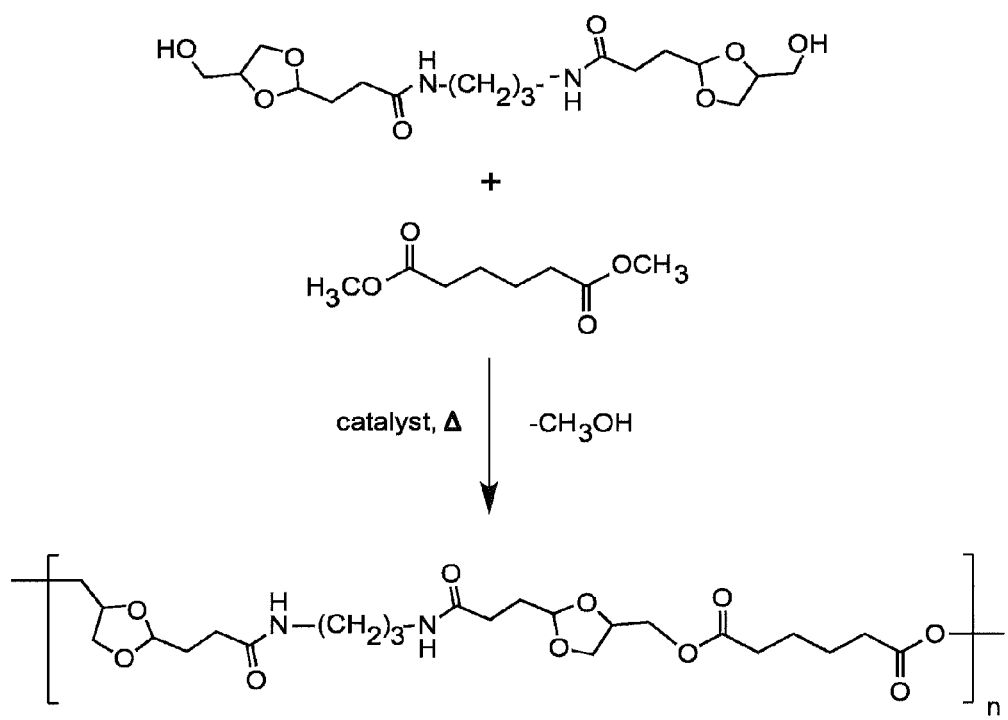

The poly(ketal amide)esters, poly(ketal amide)amides, or poly(ketal amide)thioesters of Structure I, Embodiment 2 are useful in a broad range of applications. For example, in some embodiments where A is an alkyl group having between 1 and 18 carbons, the compounds of the invention are useful as plasticizers, a coalescing solvents, cosolvents, phase transfer agents, compatibilizing agents, interfacial modifiers, or surfactants in one or more formulations. In some embodiments, the compounds are useful as plasticizers in one or more polymer formulations. In still other embodiments, the compounds are nucleating agents for one or more solid polymer formulations. A representative example of one embodiment of Structure I, Embodiment 2 wherein α is 2 and $R^7$ groups are octanoate groups is shown in FIG. 1B.

Structure I, Embodiment 2A.

Where $R^7$ of Structure I is

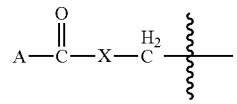

and A contains a secondary or tertiary nitrogen bonded to the C=O group and a linear, branched, or cyclic alkyl, alkenyl, or alkynylgroup, or an aryl or alkaryl group, wherein the alkyl, alkenyl, alkynyl, aryl, or alkaryl group has 1 to 36 carbon atoms and can further have one or more heteroatoms; and X is O, S, or NH, the compounds of Structure I, Embodiment 2A are poly(ketal amide)urethanes, poly(ketal amide)ureas, or poly(ketal amide) thiocarbamates. The A moiety is easily tailorable to impart the desired property, such as degree of hydrophobicity or hydrophilicity, melting point, and so forth to the compounds of Structure I.

The poly(ketal amide)urethanes, poly(ketal amide)ureas, or poly(ketal amide) thiocarbamates are obtained, in embodiments, by the reaction of, respectively, a poly(ketal amide)ol, poly(ketal amide)amine, or poly(ketal amide)thiol of Structure I, Embodiment 1 with one or more monoisocyanate compounds. The methylol, methylamino, or methylthio moieties of Structure I, Embodiment 1 have two or more reactive hydrogen atom sites that are available for reaction with an isocyanate group. Such reactions are well known in the literature and any of the commonly employed methods to form urethanes from hydroxyl groups, ureas from amine groups, or thiocarbamates from mercapto groups are useful in one or more embodiments.

Monoisocyanates useful in such reactions are, in various embodiments, any of the monoisocyanates found in the literature. Examples of suitable monoisocyanates include, in embodiments, methyl isocyanate, ethyl isocyanate, 2-chloroethyl isocyanate, propyl isocyanate, isopropyl isocyanate, n-butyl isocyanate, isobutyl isocyanate, sec-butyl isocyanate, t-butyl isocyanate, hexyl isocyanate, heptyl isocyanate, octyl isocyanate, nonyl isocyanate, decyl isocyanate, 2-(perfluorooctyl)ethyl isocyanate, undecyl isocyanate, dodecyl isocyanate, tetradecyl isocyanate, pentadecyl isocyanate, hexadecyl isocyanate, 8-hexadecyl isocyanate, cyclopentyl isocyanate, cyclohexyl isocyanate, cyclooctyl isocyanate, cyclododecyl isocyanate, p-tolyl isocyanate, o-tolyl isocyanate, benzyl isocyanate, p-anisyl isocyanate, m-fluorophenyl isocyanate, 2-ethoxyphenyl isocyanate, perfluorophenyl isocyanate, p-nitrophenyl isocyanate, 4-phenylbutyl isocyanate, chlorosulfonyl isocyanate, naphthyl isocyanate, allyl isocyanate, furfuryl isocyanate, and the like, as well as mixtures thereof.

The poly(ketal amide)urethanes, poly(ketal amide)ureas, or poly(ketal amide) thiocarbamates are useful in a broad range of applications. For example, in some embodiments where A contains an alkyl group having between 1 and 18 carbons, the compounds of the invention are useful as plasticizers, a coalescing solvents, cosolvents, phase transfer agents, compatibilizing agents, interfacial modifiers, or surfactants in one or more formulations. In some embodiments, the compounds are useful as plasticizers in one or more polymer formulations. In still other embodiments, the compounds are nucleating agents for one or more solid polymer formulations.

Structure I, Embodiment 3.

Where $R^7$ of Structure I is

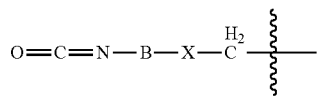

the compounds of Structure I are poly(ketal amide)isocyanates. In such embodiments, B is a linking group that is the residue of the reaction between a poly(ketal amide)ol, poly(ketal amide)amine, or poly(ketal amide)thiol of Structure I, Embodiment 1 and a diisocyanate.

The methylol, methylamino, or methylthio moieties of Structure I, Embodiment 1 have two or more reactive hydrogen atom sites that are available for reaction with a diisocyanate to form a urethane, urea, or thiocarbamate linkage and an isocyanate endgroup. The urethane, urea, or thiocarbamate linkage is thus, in some such embodiments, part of group B. The degree of isocyanate functionality imparted to the compounds of the invention depends, in embodiments, on the value of α. For example, where the trisketal amide triol is formed from the reaction of product of levulinate ester and glycerol, followed by amidation by diethylene triamine (Structure Ic), a trisketal amide triisocyanate is, in some embodiments, formed by reacting the compound of Structure Ic with 3 equivalents of a diisocyanate. In other embodiments employing the poly(ketal amide)ols of the invention, the value of α is 2; in still other embodiments, the value of α is as high as 100 or even 1000 or more. In general, the precursors to poly(ketal amide)isocyanates are any of the compounds of Structure I, Embodiment 1 described above.

In some embodiments, the degree of isocyanate functionality imparted to the compounds of the invention depends on the isocyanate functionality of one or more compounds reacted with the poly(ketal amide)ols of the invention to form one or more poly(ketal amide)isocyanates. For example, where α=2 of Structure I, Embodiment 1, the subsequent reaction with two molar equivalents of a triisocyanates results, in embodiments, in a poly(ketal amide)isocyanate having four isocyanate moieties.

The poly(ketal amide)ols are converted to poly(ketal amide)isocyanates by forming urethane, urea, or thiocarbamate linkages with diisocyanates or higher polyisocyanates, wherein one of the two available isocyanate groups react with an available hydroxyl group of a poly(ketal amide)ol, or the corresponding amino or thiol group of the poly(ketal amide) amine or poly(ketal amide)thiol. Suitable diisocyanates useful for embodiments of the urethane, urea, or thiocarbamate forming reactions include, without limitation, those represented by formula OCN—B'—NCO, in which B' represents a divalent aliphatic hydrocarbon group having 4 to 18 carbon atoms, a divalent cycloaliphatic hydrocarbon group having 5 to 15 carbon atoms, a divalent aralkyl hydrocarbon group having 7 to 15 carbon atoms, or a divalent aromatic hydrocarbon group having 6 to 15 carbon atoms.

Non-limiting examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)methane, 2,4'-dicyclohexyl-methane diisocyanate, 4,4'-dicyclohexyl-methane diisocyanate, 1,3-bis-(isocyanatomethyl)-cyclohexane, 1,4-bis-(isocyanatomethyl)-cyclohexane, bis-(4-isocyanato-3-methyl-cyclohexyl)methane, α,α,α',α'-tetramethyl-1,3-xylylene diisocyanate, α,α,α',α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, 1,5-diisocyanato naphthalene; and mixtures thereof.

Also suitable for making one or more poly(ketal amide) polyisocyanates of the invention are polyisocyanates containing 3 or more isocyanate groups. Nonlimiting examples of suitable polyisocyanates include 4-isocyanatomethyl-1,8-octamethylene diisocyanate, aromatic polyisocyanates such as 4,4',4''-triphenylmethane diisocyanate, and polyphenyl polymethylene polyisocyanates obtained by phosgenating aniline/formaldehyde condensates.

One or more poly(ketal amide) polyisocyanates of the invention are synthesized, in some embodiments, in the form of a poly(ketal amide) polyisocyanate adduct. Suitable poly(ketal amide) polyisocyanate adducts are those containing isocyanurate, uretdione, biuret, urethane, allophanate, carbodiimide and/or oxadiazinetrione groups.

In some embodiments, diisocyanates employed to make one or more poly(ketal amide) polyisocyanates of the invention include the various isomers of diphenylmethane diisocyanate and mixtures thereof, IPDI, 4,4'-dicyclohexyl-methane diisocyanate, and polymeric isocyanates based on diphenylmethane diisocyanate, such as Mondur™ MRS (available from Bayer MaterialScience LLC of Pittsburgh, Pa.).

Methods used to make one or more poly(ketal amide) isocyanates of the invention include conventional techniques known in the literature for the synthesis of polyisocyanates from polyols and diisocyanates. A representative technique for making one or more polyketal polyisocyanates of the invention from one or more poly(ketal amide) polyols is that employed in U.S. Patent Publication No. 2008/0242721, which is incorporated herein by reference in its entirety. The technique of the incorporated Application employs an excess of diisocyanate, as determined by hydroxyl equivalents per mole of polyol, in the presence of dibutyltin dilaurate to give the corresponding polyisocyanate. Poly(ketal amide)amines and poly(ketal amide)thiols are also reacted with diisocyanates and higher polyisocyanates using standard literature techniques. The reaction of poly(ketal amide)amines with isocyanate groups typically requires no catalyst; contacting the primary amine with a polyisocyanate is sufficient, in some embodiments, to bring about the reaction to form a urea group. In other embodiments, the addition of heat to the reaction mixture is required. Similarly, thiocarbamates are formed in some embodiments without the additional of catalyst, wherein addition of heat is sufficient to bring about the reaction between a poly(ketal amide) thiol and a polyisocyanate. Literature methods, such as those described by Iwakura et al., *Can. J. Chem.* 38, 1960, 2418-24; and Movassagh et al., *Monatschefte für Chemie* 139(2), 2007, 137-140, for example, are useful in making poly(ketal amide)thiocarbamates from poly(ketal amide)thiols of the invention. Structure I, Embodiment 4.

Where $R^7$ of Structure I is

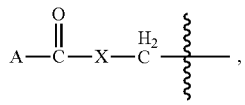

such that A is an ethylene or propylene group and X is O or NH, $R^7$ has the structure

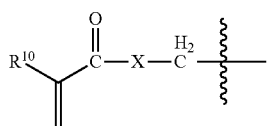

wherein $R^{10}$ is hydrogen or methyl. In such embodiments, Structure I, Embodiment 4 is a poly(ketal amide) acrylate. For example, in such embodiments, Structure I is a bisketal amide diacrylate where α is 2, X is O, and $R^{10}$ is hydrogen; a bisketal amide dimethacrylate where α is 2, X is O, and $R^{10}$ is methyl; an N-bisketal amide bisacrylamide where α is 2, X is NH, and $R^{10}$ is hydrogen; and an N-bisketal amide dimethacrylamide where α is 2, X is NH, and $R^{10}$ is methyl. In general the following discussion relates to the formation of bisketal amide diacrylate structures. However, it will be understood that the corresponding methacrylate, acrylamide, and methacrylamide adducts, as well as higher adducts, e.g. poly(ketal amide)acrylates, poly(ketal amide)methacrylates, poly(ketal amide)acrylamides and poly(ketal amide)methacrylamides, are also generally available by employing the corresponding compounds and methodology, or methodology available in the literature by employing suitable compounds of Structure I wherein α is greater than 2, X is NH, and/or $R^{10}$ of group (b) of $R^7$ in Structure I is methyl. As used herein, the terms "acrylic", "acrylate", and the like is also intended to include and incorporate the corresponding methacrylate, acrylamide, or methacrylamide moieties.

Bisketal amide diacrylates are synthesized by reacting compounds of Structure I, Embodiment 1 wherein α is 2 and $R^7$ is $CH_2OH$ or $CH_2NH_2$ with two equivalents of a suitable acrylate compound. Acrylic functionality is imparted, in embodiments, by employing conventional techniques for the reaction of alkanols to form acrylates. In one such embodiment a bisketal amide diol is employed in an esterification reaction with acrylic acid or to form a bisketal amide diacrylate. Another embodiment employs acrylyl chloride in a reaction with a bisketal amide diol to form the corresponding bisketal amide diacrylate. The reaction results in the formation of hydrochloric acid (HCl) that is advantageously scavenged by a base, for example ammonia.

In a related set of embodiments, a poly(ketal amide) isocyanate of Structure I, Embodiment 3 may be reacted with a hydroxyl-functional acrylate or methacrylate to form a urethane moiety linking the poly(ketal amide) to the acrylate or methacrylate moiety. For example, a bisketal amide diisocyanate is, in embodiments, reacted with a 3-methacrylyl-2-hydroxylpropyl ester to give the corresponding bisketal amide dimethacrylate. In another example, the bisketal amide diisocyanate is reacted with 2-hydroxypropyl acrylate to give the corresponding bisketal amide diacrylate. Urethane acrylates are known in the literature and are typically formed by synthesizing polyurethane from a diol and a diisocyanate, followed by endcapping the polyurethane isocyanate endgroup with a hydroxy functional acrylate or methacrylate as described herein above. Alternatively, the polyurethane is hydroxy endcapped and is esterified with acrylic acid or methacrylic acid. For example, Barbeau, et al., *Journal of Polymer Science Part B: Polymer Physics*, 38(21), 2750-68 (2000) disclose one reaction scheme for a prepolymer that is a polyurethane having isocyanate endgroups, endcapped with an acrylate group. In some embodiments, the poly(ketal amide) isocyanates of the invention are acrylate functionalized using this or a similar method. The acrylate functionality is then polymerized to give an acrylate polymer network. In yet another variation of this chemistry, an isocyanate endcapped material is crosslinked with a hydroxy-functional polymer, such as poly(2-hydroxypropyl acrylate) or poly(vinyl alcohol); see, for example, Decker et al., *Macromol. Mater. Eng.* 286, 5-16 (2001). In some embodiments, the poly(ketal amide)isocyanates of the invention are functionalized with a previously synthesized acrylate polymer using this or a similar method.

The various poly(ketal amide)acrylates and poly(ketal amide)methacrylates of the invention have, in various embodiments, two or more acrylic functionalities. The α,β-unsaturated portion of acrylic functionalities are capable of radical, cationic, or anionic polymerization to result in a polymer network. Such reactions are widely used in the industry and one or more acrylate functional poly(ketal amide)acrylates or poly(ketal amide)methacrylates of the invention may be reacted using any of the known techniques of polymerization or crosslinking of acrylate functionalities. Many references are available that discuss these techniques. Radical polymerization or crosslinking reactions initiated by thermal, redox, electromagnetic radiation such as ultraviolet (UV), or electron beam (ebeam) are the most common of these known techniques. Some useful references discussing such means of polymerization of acrylate functional materials are Decker et al., *Macromol. Mater. Eng.* 286, 5-16 (2001); Burlant, W., U.S. Pat. No. 3,437,514; Endruweit, et al., *Polymer Composites* 2006, 119-128; Decker, C., *Pigment and Resin Technology* 30(5), 278-86 (2001); and Jonsson et al., *Progress in Organic Coatings* 27, 107-22 (1996). Other known and useful methods are those taught by U.S. Pat. Nos. 3,437,514; 3,528,844; 3,542,586; 3,542,587; 3,641,210. Such polymerization reactions are particularly advantageous where one or more poly(ketal amide)acrylates or poly(ketal amide)methacrylates of the invention are polymerized or crosslinked, for example, in situ in a coated formulation, in a syrup preparation for coating, and the like. Any of the techniques employed in these references may be advantageously employed to react the acrylate functional poly(ketal amide)s of the invention, resulting in branched or crosslinked polymer networks.

Many useful extensions of the above embodiments of the invention are readily envisioned wherein poly(ketal amide)acrylates and poly(ketal amide)methacrylates are employed. For example, in one embodiment, a bisketal amide diacrylate is employed as a crosslinker when blended with additional acrylate functional compounds, typically monoacrylate functional compounds, in a radical polymerization reaction. In other embodiments, any one or more of the polymers described above are provided with acrylic functionality by employing the reactions described above, to form polyketal acrylate prepolymers. In some such embodiments, the polyketal acrylate prepolymers are processed, for example by coating, extruding, mold filling, and so forth, with or without additional solvents, prior to reaction of the acrylate groups. The prepolymers may further be blended with one or more additional acrylate functional compounds and/or additional vinyl functional compounds. After processing, the prepolymers are reacted to form a branched and/or crosslinked network. The resulting networks are thermoset or thermoplastic. It is readily understood that the properties of the networks will vary greatly depending on both the nature of the compounds used and crosslink density.

Additional acrylate functional compounds include compounds having one or more acrylate, alkylacrylate, acrylamide, or alkylacrylamide residues. Non-limiting examples of useful acrylate functional compounds include acrylic acid, methacrylic acid, acrylamide, methacrylamide, N-hydroxymethyl acrylamide, methacryloxyethyl phosphate, acrylonitrile, methacrylonitrile, 2-acrylamido-2-methylpropanesulfonic acid and salts thereof; maleic acid, its salt, its anhydride and esters thereof; monohydric and polyhydric alcohol esters of acrylic and alkylacrylic acid such as 1,6 hexane diol diacrylate, neopentyl glycol diacrylate, 1,3 butylene dimethacrylate, ethylene glycol diacrylate, trimethylolpropane triacrylate, pentaerythritol triacrylate, pentaerythritol tetracrylate, etc.; other oxygenated derivatives of acrylic acid and alkylacrylic acids, e.g., glycidyl methacrylate, hydroxyethyl methacrylate, hydroxypropyl methacrylate, etc.; halogenated derivatives of the same, e.g., chloroacrylic acid and esters thereof; and diacrylates and dimethacrylates, e.g., ethylene glycol diacrylate. In some embodiments, the additional acrylate functional compounds are present in blends with poly(ketal amide)acrylates of up to about 99.9 mole percent of the additional acrylate compounds, such as between about 50 mole percent to 99.9 mole percent of additional acrylate functional compounds relative to the poly (ketal amide)acrylates of the invention.

Additional vinyl functional compounds include non-acrylate functional α,β-unsaturated compounds capable of copolymerizing with the acrylate functional compounds and/or poly(ketal amide)acrylates and poly(ketal amide)methacrylates. Non-limiting examples of additional vinyl compounds include aromatic polyvinyl compounds such as divinyl benzene, aromatic monovinyl compounds such as styrene, methyl substituted styrenes such as α-methyl styrene, vinyl toluene, t-butyl styrene, chlorostyrene, and the like; aliphatic monovinyl compounds such as α-olefins, e.g. propylene, 1-octene, and the like. Other additional vinyl functional compounds useful in blends with the poly(ketal amide)acrylates and poly(ketal amide)methacrylates are the divinyl and tetravinyl compounds disclosed in U.S. Pat. Nos. 3,586,526; 3,586,527; 3,586,528; 3,586,529; 3,598,530; 3,586,531; 3,591,626; and 3,595,687.

Structure I, Embodiment 5.

In embodiments of Structure I where $R^7$ is

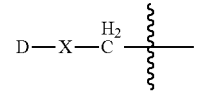

such that X is O or NH and D is

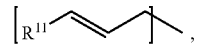

wherein $R^{11}$ is hydrogen, a linear, cyclic, or branched alkyl, alkenyl, or alkynyl group, an aralkyl group, or an aromatic group, the compounds of Structure I are poly(ketal amide) allyl ethers or poly(ketal amide)N-allylamines. For example, in such embodiments, Structure I, Embodiment 5 is a bis (ketal amide)allyl ether where α is 2 and X is O; or a tris(ketal amide)N-allylamine where α is 3 and X is NH. As used herein, the term "allyl functionality" means a —$CH_2$—CH=$CH_2$ moiety that is capable of subsequent polymerization or crosslinking reactions utilizing a free radical or redox mechanism. Allylic (polyketal amide)s are, in general, synthesized from poly(ketal amide)ols or poly(ketal amide)amines with allyl halides.

Examples of suitable allyl halides for use in forming the poly(ketal amide)allyl ethers and poly(ketal amide)-N-allylamines of the invention include, without limitation, allyl chloride, allyl bromide, methallyl chloride, 2-(trimethylsilylmethyl)allyl chloride, 1-halo-2-alkenes such as 1-bromo-2-butene, 1-chloro-2-pentene, 1-bromo-2-cyclohexylethylene, cis/trans isomers thereof, and the like.

In general, any known technique may be employed to form the poly(ketal amide)allyl ethers of the invention. In particular, the reaction of organic alcohols with allyl halides is known in the literature. Typically, sodium hydride (NaH) is employed to facilitate the reaction of allyl bromide and an alkanol to form the corresponding alkyl-allyl ether. For example, see http://www.organic-chemistry.org/protective-groups/hydroxyl/allyl-ethers.htm, citing Green et al., *Protective Groups in Organic Synthesis*, Wiley-Interscience, New York, 1999, 67-74, 708-711. This and other methods are used, in embodiments, to synthesize the poly(ketal amide)allyl ethers of Structure I, Embodiment 5 of the invention. Similarly, literature methods are also known for synthesis of N-allyl alkylamines. For example, de Jesus et al., *React. Kinet. Catal. Lett.* 84, 2, 255-62 (2005) disclose palladium catalyzed formation of allylamines; and Hachemaoui et al., *Mendeleev Commun.* 2005, 15(3), 124-125 disclose a montmorillonite clay catalysis route to allylamines. These techniques are employed, in various embodiments, to synthesize the poly(ketal amide)-N-allyl amines of the invention.

The one or more allylic compounds of Structure I, Embodiment 5 are, in embodiments, polymerized using any of the techniques known in the literature. For example, heating allyl monomers in the presence of thermal free-radical initiators gives polymeric products. Typically, allyl polymers are made by charging the allyl monomer and a free-radical initiator to a reactor, and heating the mixture at a temperature effective to polymerize the monomer (see, e.g. "Kirk-Othmer Encyclopedia of Chemical Technology," $4^{th}$ ed., Volume 2, pp. 161-179). Improved methods of polymerizing allyl compounds are also usefully employed with one or more allylic polyketals of the invention. For example, Guo et al., U.S. Pat. No. 5,420,216 discloses that gradual addition of initiator is key to high conversion in allyl polymerization.

In some embodiments of the invention, the two or more reactive double bonds per poly(ketal amide)allyl ether or poly(ketal amide)-N-allyl amine yield solid, high molecular weight polymers by initiation with a suitable free-radical catalyst. Such embodiments are useful to provide, for example, heat-resistant cast sheets and thermoset moldings. In some such embodiments, the reactivity of compounds having two or more allyl group permits polymerization in two stages: a solid prepolymer containing reactive double bonds is molded by heating; then completion of polymerization gives cross-linked articles of superior heat resistance. In embodiments, the relatively slow rate of polymerizations is controlled more readily than in the polymerization of polyfunctional vinyl compounds to give soluble prepolymers containing reactive double bonds.

One useful embodiment of one or more allylic compounds of Structure I, Embodiment 5 employs minor proportions of one or more polyfunctional poly(ketal amide) allyl ethers or poly(ketal amide)-N-allyl amines for cross-linking or curing preformed vinyl-type polymers. Among the preformed polymers cured by minor additions of allyl functional monomers and catalysts followed by heat or irradiation are polyethylene, PVC, and acrylonitrile-butadiene-styrene (ABS) copolymers. These reactions are examples of graft copolymerization in which specific added peroxides or high energy radiation achieves optimum cross-linking. In other embodiments, small proportions of poly(ketal amide)allyl ethers or poly(ketal amide)-N-allyl amines are added as regulators or modifiers of vinyl polymerization for controlling molecular weight and polymer properties. In yet other embodiments, poly(ketal amide)allyl ethers or poly(ketal amide)-N-allyl amines are of high boiling point and compatibility are employed as stabilizers against oxidative degradation and heat discoloration of polymers.

One useful embodiment of one or more thermoset poly(ketal amide)allyl ethers or poly(ketal amide)-N-allyl amines are of the invention is in moldings and coatings for electronic devices requiring high reliability under long-term adverse environmental conditions. These devices include electrical connectors and insulators in communication, computer, and aerospace systems. Other embodiments are readily envisioned.

Structure I, Embodiment 6.

In embodiments of Structure I where $R^7$ is

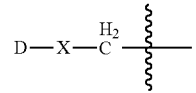

such that X is O and D is

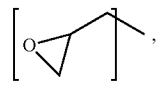

Structure I is a poly(ketal amide) glycidyl ether. Poly(ketal amide)ols are useful, in embodiments, for the synthesis of poly(ketal amide) glycidyl ethers. Such embodiments include bisketal amide diglycidyl compounds derived from Structure I, Embodiment 1 wherein α is 2; or poly(ketal amide) glycidyl compounds wherein α is between about 3 and 100.

In some embodiments, an epihalohydrin such as epichlorohydrin is used to functionalize one or more poly(ketal amide)ols of Structure I, Embodiment 1. The reaction between an alcohol and epichlorohydrin to form a glycidyl ether is known in the literature. For example, the reaction of the alcohol Bisphenol A with epichlorohydrin is a well known reaction by which epoxy resins are formed; see, for example, Andrews et al., U.S. Pat. No. 5,420,312 and Chanda, M. and Roy, S., eds., *Plastics Technology Handbook*, $4^{th}$ ed., © 2007 Taylor & Francis Group, LLC, pp. 4-114 to 4-116. These and other conventional techniques are employed, in embodiments, to react epichlorohydrin with one or more poly(ketal amide)ols of Structure I, Embodiment 1 to form poly(ketal amide) glycidyl ethers of the invention.

Another technique employed, in some embodiments, to provide compounds having Structure I, Embodiment 6 is to react a poly(ketal amide) allyl ether of Structure I, Embodiment 5 with a peroxide. For example, Au, U.S. Pat. No. 5,036,154 discloses a method whereby an ethylenically unsaturated ester group, such as an allyl ester, is reacted with hydrogen peroxide in the presence of an alkali metal or alkaline earth metal salt of tungstic acid, phosphoric acid, and a phase transfer catalyst to give the epoxidized product of the unsaturated moiety. Such a technique is used, in embodiments, to form a poly(ketal amide)glycidyl ether from the corresponding allyl ether. Other techniques employed in the literature are similarly useful to obtain one or more epoxidized products of allyl esters of the invention.

In a related embodiment that results in an oxirane functional compound, one or more unsaturated fatty acid esters of one or more poly(ketal amide)ols, e.g. the poly(ketal amide) esters described in Structure I, Embodiment 2, are reacted with a peroxide to form a poly(ketal amide) oxirane adduct. The techniques that are, in embodiments, employed to carry out such reactions are the same as those described above for the reaction of a peroxide with an allyl ether. Additionally, Du et al., *J. Am. Org. Chem. Soc.* 81(4) 477-480 (2004) describe the esterification of a carboxylate with one or more unsaturated fatty acids, followed by reaction of one or more unsaturated sites of the unsaturated fatty acid ester with hydrogen peroxide to form the corresponding oxiranyl adducts. Any of these methods are used, in various embodiments, to form the oxiranyl adducts of poly(ketal amide) esters of unsaturated fatty acids.

One or more poly(ketal amide) glycidyl ethers or poly(ketal amide) oxiranyl adducts of the invention are, in embodiments, subsequently polymerized using standard techniques such as those found in the literature. The polymerization of epoxy groups, for example with amines, amides, or anhydrides, is widely known. A useful summary of compounds and mechanisms of curing epoxy groups is found in Chanda, M. and Roy, S., eds., *Plastics Technology Handbook*, 4th ed., © 2007 Taylor & Francis Group, LLC, pp. 4-116 to 4-122. Any of the techniques employed or referenced therein are used, in various embodiments, to polymerize the epoxy groups present on one or more poly(ketal amide) glycidyl ethers or poly(ketal amide) oxiranyl esters of the invention to form the corresponding linear or crosslinked polymer.

Applications of polymerized oxiranyl and glycidyl compounds are numerous and broad in scope. Due to their high strength, variable crosslink density, and variable chemical starting materials, such compounds have found broad applicability for numerous applications. Many of the most common applications are set forth in Chanda, M. and Roy, S., eds., *Plastics Technology Handbook*, 4th ed., © 2007 Taylor & Francis Group, LLC, pp. 2-80 to 2-81, 7-26, and 4-124 to 4-125. The resins formed by curing the glycidyl and oxiranyl functional poly(ketal amide) compounds of the invention are, in various embodiments, useful in one or more of these applications.

Structure II.

The invention embodies compounds having one or more fragments corresponding to Structure II

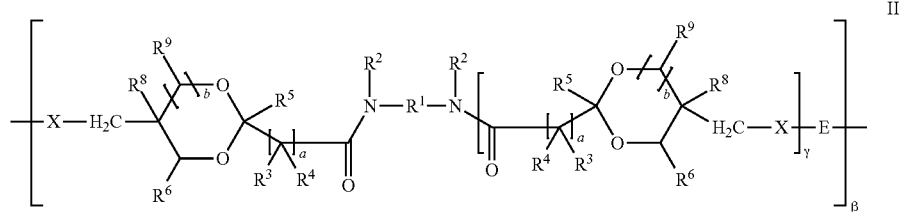

wherein $R^1$, $R^2$, $R^3$, $R^4$, $R^5$, $R^6$, $R^8$, $R^9$, X, a, and b are as defined for Structure I;

γ is 0 or 1;

β is an integer of at least 1; and

E is a linking group selected from (a)-(d) as follows,

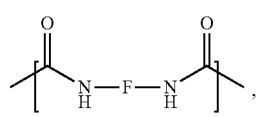

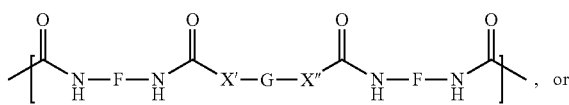, or

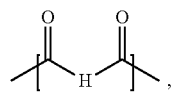

wherein E is the same or different for each repeat unit represented by β.

It will be recognized that where linking group E is (a), the compound of Structure II is the divalent residue of phosgene or an organic bicarbonate; where linking group E is (b) the compound of Structure II is the divalent residue of a diisocyanate; where linking group E is (c), the compound of Structure II is the divalent residue of a diol, diamine, dithiol, or a hybrid compound such as an aminoalcohol, thioalcohol, and the like reacted with a diisocyanate; and where linking group E is (d), the compound of Structure II is the divalent residue of a diacid, diester, anhydride, or diacid chloride.

Combinations of various linking groups E are available, in embodiments, in a single compound corresponding to Structure II. For example, a polymeric compound of Structure II having repeat unit β wherein one or more linking groups are (a) may have terminal groups that are hydroxyl; the hydroxy-terminated compound is then reacted with one or more polyisocyanates to provide linking groups (b). Many other embodiments wherein more than one linking group E is present in a single compound are easily envisioned. Any of these combinations are possible in the Structure II Embodiments 1 through 4 described below and none of the Embodiments described are limited to a single linking group E, but rather are grouped according to discussion of each different linking group E.

In some embodiments of the compounds of Structure II, γ is 1. In some such embodiments, the starting materials for making the compounds of Structure II include one or more fragments that are based on the poly(ketal amide)ols, poly(ketal amide)amines, and poly(ketal amide)thiols of Structure I, Embodiment 1 as well as and poly(ketal amide)isocyanates of Structure I, Embodiment 3. Where the compounds of Structure I are employed as the starting materials for the synthesis of the compounds of Structure II, the compounds of Structure II have γ=1: that is, the bis(ketal amide) diols, bis(ketal amide) diamines, bis(ketal amide) dithiols, and diisocyanates thereof of Structure I, embodied by α=2, are the starting materials in forming the compounds of Structure II. Such starting materials are, for example, the compounds of Structure I, Embodiment 1 wherein α is 2 and both $R^7$ are methylol, methylamino, or methylthiol as well as compounds of Structure I, Embodiment 3 wherein α is 2.

In other embodiments of Structure II where γ is 1, the starting materials for making the compounds of Structure II are ketal esters and diamines, which are the same starting materials as those described for the synthesis of compounds having Structure I, along with fragments attributable to any one of the linking groups E. The ketal esters are, in embodiments, any of those disclosed in International Patent Application Nos. PCT/US08/075,225 or PCT/US08/79083, or U.S. Patent Publication No. 2008/0242721, which is incorporated herein by reference, and substantially as described for Structure I. The ketal esters and diamines are reacted, in various embodiments, with phosgene or an organic bicarbonate; a diisocyanate; a diol, dithiol, or a hybrid compound such as an aminoalcohol, thioalcohol, and the like; a diacid, diester, anhydride, or diacid chloride; or a mixture of one or more of these. When all starting materials are mixed and reacted in a single step, some diamines react, in embodiments, with two equivalents of ketal ester, to result in one or more fragments of Structure II where γ is 1. For example, such fragments can arise where the ketal ester is more reactive toward the diamine than another chemical in the reaction mixture, such as a diester or a bicarbonate, with which the diamine is also capable of reacting.

In similar embodiments, where all starting materials are mixed and reacted in a single step as described immediately above, the resulting compound of Structure II contains a mixture of fragments having γ=1 and γ=0. Such embodiments arise where a diamine reacts both with a ketal ester and with phosgene or an organic bicarbonate; a diisocyanate; a diol, dithiol, or a hybrid compound such as an aminoalcohol, thioalcohol, and the like; a diacid, diester, anhydride, or diacid chloride; or a mixture of one or more of these in a statistical fashion based on stoichiometry, relative reactivities of the various chemical compounds in the reaction mixture, or both.

In some embodiments of the compounds of Structure II, γ is 0. In some such embodiments, the starting materials for making the compounds of Structure II include one or more compounds that are based on the reaction of a diamine with phosgene or an organic bicarbonate; a diisocyanate; a diacid, diester, anhydride, or diacid chloride; or a mixture of one or more of these. These starting materials are then reacted with a ketal ester or a poly(ketal ester) to give the compounds of Structure II. In other words, order of addition of the reagents in various embodiments will result in a compound of Structure II wherein γ is 0, 1, or a mixture wherein fragments having both γ=0 and γ=1 are contained in a single compound.

In some embodiments of Structure II, $R^1$ is —$(CH_2)_3$—. In other embodiments, $R^1$ is 1,2-cyclohexyl. In still other embodiments, $R^1$ is —$(CH_2)_6$—. In some embodiments of Structure II, is 0, 1, or 2. In other embodiments, the value of a is 2 and all $R^3$ and $R^4$ are hydrogen. In embodiments, $R^5$ is methyl. In embodiments, b is 0 and $R^6$ and $R^8$ are hydrogen.

In some embodiments, the compounds of Structure II are formed from starting materials such as, for example, pyruvic acid (a=0), acetoacetic acid (a=1, $R^3$, $R^4$=H), or levulinic acid (a=2, all $R^3$, $R^4$=H) or an ester thereof with glycerol (b=0, $R^7$=CH$_2$OH, $R^6$, $R^8$=H), 1,1,1-trimethylolpropane (b=1, $R^7$=—CH$_2$OH, $R^8$=CH$_2$CH$_3$, $R^6$, $R^9$=H), or 1,1,1-trimethylolethane (b=1, $R^7$=—CH$_2$OH, $R^8$=CH$_3$, $R^6$, $R^9$=H). Levulinic acid is an abundant feedstock that is prepared on an industrial scale by acidic degradation of hexoses and hexose-containing polysaccharides such as cellulose, starch, sucrose, and the like.

Structure II, Embodiment 1

The various embodiments described for Embodiment 1 recite compounds and methods used in the synthesis of the compounds of Structure II that result in γ=1. However, the discussion above regarding order of addition, stoichiometry, and relative reactivity of the compounds employed in the synthesis of the compounds of Structure II apply with equal force to the compounds of Embodiment 1. It will be understood that Embodiment 1 also extends to compounds of Structure II wherein γ is 0, 1, or a mixture thereof.

In embodiments where linking group E of Structure II is (a), the polymeric structure is a poly(bisketal amide carbonate) where X is O, poly(bisketal amide urea) where X is NH, or poly(bisketal amide thiocarbonate) where X is S, Notably, thiocarbonate compounds can be further stabilized against degradation to form CS$_2$ (carbon disulfide) using the techniques set forth in Green II et al., U.S. Pat. No. 5,340,593. The following discussion relates to the formation of poly(bisketal amide carbonate)s. However, it will be understood that the corresponding urea and thiocarbonate functional polymers are also generally available by employing similar compounds and methodology, or methodology available in the literature. Also, it will be readily understood that similar polymeric structures containing branched or crosslinked morphologies are available by employing analogs of Structure I, Embodiments 1 and 3 wherein the value of α is more than 2; such analogs may be present as part of a reactive mixture to form one or more branched or crosslinked analogs of the polymers of Structure II where linking group E is structure (a).

In some embodiments, the poly(bisketal amide carbonate)s of the invention have a value of β that is 1. In other embodiments, β is between 2 and 12. In still other embodiments, the value of β is as high as 100. In still other embodiments, the value of β is as high as 1000.

Poly(bisketal amide carbonate) synthesis is carried out, in embodiments, by employing any known and conventional technique for making polycarbonates. One such technique employs phosgene. For example, in one such embodiment, a bisketal amide diol is treated with sodium hydroxide, followed by an interfacial reaction between the sodium alkoxide of the bisketal amide diol and phosgene. Alternatively, one or more poly(bisketal amide carbonate)s of the invention are synthesized, in embodiments, by transesterification of a polyketal ester with a difunctional carbonate having the general structure

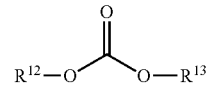

where $R^{12}$ and $R^{13}$ may be the same or different and are, in embodiments, a linear, cyclic, or branched alkyl, alkenyl, or alkynyl group; an aralkyl group, or an aromatic group. In some embodiments, $R^{12}$ and $R^{13}$ together with the carbonate bond forms a cyclic carbonate; in these embodiments, a poly(bisketal amide carbonate) is formed by a ring opening reaction. Poly(bisketal amide carbonate)s are also formed, in embodiments, by reacted a dibromo bisketal amide compound with potassium carbonate. Thus, in one such embodiment, a precursor bisketal amide of Structure I wherein a is 2 and $R^7$ is —CH$_2$Br is reacted with potassium carbonate to form a poly(bisketal amide carbonate) of the invention.

The poly(bisketal amide carbonate)s of the invention have a range of available properties due to the broad range of bisketal amide diols of the invention that are available as starting materials. Polycarbonates are known to be tough, transparent, thermally stable materials suitable for a range of engineering plastics applications. Suitable applications for one or more poly(bisketal amide carbonate)s of the invention include, but are not limited to, fabrication of items requiring molding, laminating, thermoforming such as extruding or coextruding, or machining or other conventional means of working. Examples of useful items include compact discs, riot shields, baby bottles and other water/drink bottles and food containers, electrical components, automobile headlamps, as a component of a safety glass laminate, eyeglass lenses, safety helmets, and the like.

The poly(bisketal amide carbonate)s of the invention do not employ Bisphenol A (4,4'-dihydroxy-2,2-diphenylpropane), the most commonly employed polycarbonate polyol starting material. Bisphenol A has been the subject of toxicity concerns since the 1930s, particularly in food or drink contact applications (e.g., baby bottles, water/drink bottles, food containers). One or more polycarbonates of the invention are, in one or more embodiments, are useful for food or drink applications where it is desirable to eliminate Bisphenol A.

Additionally, some aliphatic poly(bisketal amide carbonate)s of the invention are, in some embodiments, biodegradable. Biodegradable polycarbonates are useful for one or more applications, for example, in food or drink contact applications, to enable disposable embodiments of various containers. Other applications where biodegradability is advantageous include disposable medical supplies such as eye shields and the like. In various embodiments, the polyketal ester polycarbonates of the invention advantageously supply the desirable properties associated with polycarbonates and additionally supply biodegradability thereof.

In some embodiments, poly(bisketal amide carbonate)s of the invention, when terminated by hydroxyl endgroups, are suitable as diols for use in polyurethane synthesis. Poly(bisketal amide carbonate urethane)s are synthesized, in some embodiments, by employing bisketal amide diols in the synthesis of a polycarbonate and controlling stoichiometry of the polymerization in order to provide hydroxyl functionality at the ends of the poly(bisketal amide carbonate). In other embodiments, a poly(bisketal amide carbonate) is transesterified at each end with a diol to provide hydroxyl endgroup. Various poly(bisketal amide carbonate)s having hydroxyl endgroups are reacted, in embodiments, with one or more diisocyanates to form a poly(bisketal amide carbonate urethane). Poly(bisketal amide carbonate urethane)s are synthesized using, in some embodiments, the techniques described below to make polyketal polyurethanes. In other embodiments, techniques used to form the polyketal poly(carbonate urethane)s of the invention are those outlined in Moore et al., *Novel Co-Polymer Polycarbonate Diols for Polyurethane Elastomer Applications*, Proceedings of the Polyurethanes Expo 2003, Oct. 1-3, 2003 (© 2003, American Chemistry Council).

Structure II, Embodiment 2.

The various embodiments described for Embodiment 2 recite compounds and methods used in the synthesis of the compounds of Structure II that result in $\gamma=1$. However, the discussion above regarding order of addition, stoichiometry, and relative reactivity of the compounds employed in the synthesis of the compounds of Structure II apply with equal force to the compounds of Embodiment 2. It will be understood that Embodiment 1 also extends to compounds of Structure II wherein $\gamma$ is 0, 1, or a mixture thereof.

In embodiments where linking group E of Structure II is (b), Structure II is a poly(bisketal amide urethane) where X is O, poly(bisketal amide urea) where X is NH, or poly(bisketal amide thiocarbamate) where X is S. The identity of F within linking group D is not particularly limited; it can be any of the groups B' listed above (in the section Structure I, Embodiment 3) for the diisocyanate structure OCN—B'—NCO. The diisocyanate that results in the residue (b), when incorporated into a poly(bisketal amide urethane), can be any of the diisocyanates and analogs thereof described above, in various nonlimiting examples. In general the following discussion relates to the formation of poly(bisketal amide urethane) structures. However, it will be understood that urea and thiocarbamate functional polymers are also generally available by employing the corresponding compounds and methodology, or methodology available in the literature, where X of Structure II is NH or S, respectively. Also, it will be readily understood that similar polymeric structures containing branched or crosslinked morphologies are available by employing analogs of Structure I where the value of α is more than 2; such analogs may be present as part of a reactive mixture to form one or more branched or crosslinked analogs of the polymers of Structure II where linking group D is structure (b).

Bisketal amide diols having Structure I, Embodiment 1 are reacted, in some embodiments, with diisocyanates such as any of those described above to result in the compounds of Structure II wherein linking group E is (b). Whereas a stoichiometric excess of diisocyanate relative to bisketal amide diol results in a poly(ketal amide)isocyanate as described above, a 1:1 stoichiometric ratio of bisketal amide diol and diisocyanate results in the formation of a linear poly(bisketal amide urethane) having at least one repeat unit corresponding to the repeat unit of Structure II such that $\beta$ is at least 1. In other embodiments, $\beta$ is between 2 and 12. In still other embodiments, the value of $\beta$ is as high as 100. In still other embodiments, the value of $\beta$ is as high as 1000.

While diisocyanates are employed in various embodiments to form the poly(bisketal amide urethane)s of the invention, additional polyisocyanates of higher functionality may also be incorporated. Blends of diisocyanates with polyisocyanates having three or more isocyanate moieties are employed, in embodiments, to provide a tailored level of branching or crosslinking in the resulting poly(bisketal amide urethane) matrix. Additionally, other diols and higher polyols that are not bisketal amide diols are optionally blended with the bisketal amide diols of the invention in a urethane synthesis to provide variation in the properties of the poly(bisketal amide urethane)s of the invention by varying their structure. Useful polyols for such embodiments include any diols and higher polyols listed and/or incorporated by reference in the sections above. Various other embodiments are easily envisioned. In forming polymers with values of $\beta$ greater than about 2 to 12, it is important to control stoichiometry carefully so as to maintain a ratio of hydroxyl to isocyanate functionality of as close to 1:1 as possible. Blends of polyisocyanate functional and polyhydroxylated materials are used, in embodiments, to form poly(bisketal amide urethane)s having a broad range of ketal content, branching and/or crosslink density and a wide range of available physical properties including glass transition temperature, tensile strength, ductility, clarity, rigidity, elasticity and the like.

In one set of embodiments, poly(bisketal amide urethane)s are present as blocks in a copolymer with other polyurethane or poly(urethane urea), or poly(urethane thiocarbamate) blocks. Such block copolymers are easily achieved by controlling stoichiometry of the reactions to reach the desired residual endgroups, then employing those endgroups as initiation points for an additional polymerization reaction with a different monomer mixture. For example, a bisketal amide diol of the invention may be reacted with a first diisocyanate to form a poly(bisketal amide urethane) oligomer; the stoichiometry of the reaction is adjusted, using conventional techniques, to result in hydroxyl endgroups. The hydroxyl terminated poly(bisketal amide urethane) oligomer is then reacted with a second diisocyanate in a blend with a second diol to provide a diblock type polyurethane polymer. Various embodiments that are variations of this embodiment are easily envisioned, such as providing two different bisketal amide diols in two oligomerizations with the same or two different diisocyanates, then reacting the two oligomers in a final reaction to form diblock poly(bisketal amide urethane)s.

In another set of embodiments, a poly(bisketal amide ester) or copolyester thereof is synthesized according to the methods set forth below and employing a one or more bisketal amide diols, adjusting stoichiometry such that residual hydroxyl endgroups are present, $\beta$ is about 2 to 12, or about 12 to 100, or even 100 to 1000, and linking group E is (d) (embodiments which are more fully described below). The hydroxyl endgroups are useful in one or more subsequent reactions to form a poly(bisketal amide urethane) by reacting the hydroxyl terminated polyester or copolyester with a polyisocyanate to produce a poly(bisketal amide ester urethane). Several additional variations of such embodiments are possible.

It will be appreciated that in various embodiments the ketal content of the resulting poly(bisketal amide urethane) polymers is widely variable, and a wide range of physical properties such as glass transition temperature, tensile strength, elasticity, and ductility are attainable in various embodiments of the invention.

The reactions and processes used to form various poly (bisketal amide urethane)s of the invention employ conventional techniques of polyurethane synthesis; such techniques typically involve blending the two reagents in a stoichiometry that will result in oligomeric or polymeric molecular weights. In embodiments, the reaction is catalyzed. Catalysts useful in poly(bisketal amide urethane) formation include, in embodiments, tertiary amines Nonlimiting examples of suitable tertiary amines include dimethylcyclohexylamine, 1,4-diazabicyclo[2.2.2]octane (also called DABCO or TEDA), and bis-(2-dimethylaminoethyl)ether. In other embodiments, organometallic compounds, such as dibutyltin dilaurate, potassium octanoate, or bismuth octanoate may be used to catalyze poly(bisketal amide urethane) formation. In some embodiments where X of Structure II is NH or S, no catalyst is required to drive the reaction. Addition of heat is, in some embodiments, sufficient to bring about the reaction of a bisketal amide diol, bisketal amide dithiol, or bisketal amide diamine with a diisocyanate. The processes described above for the reaction of poly(ketal amide)amines and poly(ketal amide)thiols with polyisocyanates to form poly(ketal amide) isocyanates apply in general to the analogous reactions of bisketal amide diamines and bisketal amide dithiols with diisocyanates to form high polymers having urea and thiocarbamate linkages.

Processes employing the poly(bisketal amide urethane)s of the invention include, in embodiments, reaction injection molding, prepolymerization to a coatable syrup followed by coating and curing, and the like. The various poly(bisketal amide urethane)s of the invention are not particularly limited as to the methods employed in the processing thereof.

Foamed formulations employing the various poly(bisketal amide urethane)s of the invention are useful embodiments of the invention. Foams are formed during the polymerization reaction, typically by the addition of one or more blowing agents. In some embodiments, a blowing agent is added to the polymer during processing to facilitate foaming when the polymer is heated, for example in a thermoforming process. Suitable blowing agents include water, certain halocarbons such as HFC-245fa (1,1,1,3,3-pentafluoropropane) and HFC-134a (1,1,1,2-tetrafluoroethane), and hydrocarbons such as n-pentane. In some embodiments, blowing agents are incorporated into e.g. the polyketal polyol prior to the polymerization; in other embodiments the blowing agent is added as an auxiliary stream. Halocarbons and hydrocarbons are chosen such that they have boiling points at or near room temperature; these blowing agents volatilize into a gas during the exothermic polymerization reaction. In addition, high density microcellular foams are formed, in embodiments, without the addition of blowing agents by mechanically frothing or nucleating the polyol component of the reaction mixture prior to polymerization.

In some embodiments, surfactants are employed to modify the characteristics of the foam during the foaming process. In embodiments, they are used to emulsify the liquid components, regulate cell size, and stabilize the cell structure to prevent collapse and surface defects. Rigid foam surfactants produce, in embodiments, very fine cells and very high closed cell content. In other embodiments, flexible foam surfactants stabilize the reaction mass while maximizing open cell content to prevent the foam from shrinking. The need for, and choice of, surfactant is determined, in embodiments, by choice of reaction components, component compatibility, system reactivity, process conditions and equipment, tooling, part shape, and shot weight.

Various embodiments of the poly(bisketal amide urethane)s of the invention are useful in a broad range of applications. Polyurethane polymers, in general, are compounds of exceptional industrial utility; they find numerous applications because the final properties of the resulting polymer can be influenced greatly through selection of active hydrogen monomers (typically, polyhydroxyl compounds) and isocyanates used, and by selecting the conditions used to prepare the finished polymer products. In various embodiments, the poly(bisketal amide urethane)s of the invention are lightweight, strong, durable and resistant to abrasion and corrosion. Depending on choice of monomers, poly(bisketal amide urethane)s range from stiff to flexible at ambient temperatures. The broad range of bisketal amide diol chemistry as well as the range of linkages available from ester, urethane, urea, and thiocarbamate in various embodiments provides extensive flexibility in choice of structure that leads to a broad range of properties and, in turn, applications.

Without providing any particular limitations, the various poly(bisketal amide urethane)s of the invention are useful, in embodiments, as adhesives or sealants, particularly for exterior uses or building construction applications where extremely challenging conditions are encountered; as binders; as coating materials where durability and/or challenging environmental conditions exist; in reactive spray coatings of 100% solids; as elastomers for applications such as rollers and belts for carrying heavy and/or abrasive materials, roller blades, and other footwear parts such as shoe soles; as vibration damping materials; and in the fabrication of medical devices, for example for surface modification, as a protective coating, or within moving parts (e.g. for elastomeric materials). In foamed form, these materials also find utility as insulation materials; low density vibration damping materials; flexible foam for indoor furniture such a seat cushions and mattresses, and other similar applications such as automobile seat cushions.

Structure II, Embodiment 3.

The various embodiments described for Embodiment 3 recite compounds and methods used in the synthesis of the compounds of Structure II that result in $\gamma=1$. However, the discussion above regarding order of addition, stoichiometry, and relative reactivity of the compounds employed in the synthesis of the compounds of Structure II apply with equal force to the compounds of Embodiment 3. It will be understood that Embodiment 1 also extends to compounds of Structure II wherein $\gamma$ is 0, 1, or a mixture thereof.

Similarly to polymeric compounds of Structure II where linking group E is (b), in embodiments where linking group E of Structure II is (c), Structure II is a poly(ketal amide urethane), poly(bisketal amide urea), poly(bisketal amide thiocarbamate), or any one of a variety of hybrid heteroatomic structures depending on whether X, X', and X" are O, NH, or S. It will be understood that the various linking groups E available having substructure (c) are the result of the reaction of compounds with two active hydrogen atoms, HX'-G-X"H, with the poly(ketal amide)isocyanate compounds of Structure I, Embodiment 3 to result in linking group (c). Compounds HX'-G-X"H are dithiols, diols, diamines, or "hybrid" compounds such as amino alcohols (e.g. compounds such as ethanolamine). Any of the diols, dithiols, or diamines listed in the above sections are useful in forming the linking groups (c) in combination with the poly(ketal amide)isocyanates of Structure I, Embodiment 3. Such diols, dithiols, or diamines include the bisketal amide diols, bisketal amide diamines, or bisketal amide dithiols described in Structure I, Embodiment 1.

Suitable "hybrid" compounds include, without limitation, 2-aminoethanol, 3-aminopropan-1-ol, isopropanolamine, 2-aminopropan-1-ol, 2-aminobutan-1-ol, 2-amino-3-methylbutan-1-ol, 2-amino-4-methylpentan-1-ol, 6-aminohexan-1-ol, 1-amino-3-chloropropan-2-ol, 7-aminobicyclo[2.2.2]octan-8-ol, 2-aminopyridin-3-ol, 2-amino-4-phenylphenol, 5-aminonaphthalen-1-ol, 4-(4-aminophenyl)phenol, 2-mercaptoethanol, 3-methyl-3-hydroxybutane-1-thiol, pyridoxine-4-thiol, 11-mercapto-1-undecanol, and the like.

It will be readily understood that similar polymeric structures containing branched or crosslinked morphologies are available by employing analogs of Structure I, Embodiments 1 and 3 where the value of $\alpha$ is more than 2; such analogs may be present as part of a reactive mixture to form one or more branched or crosslinked analogs of the polymers of Structure II where linking group E is structure (c). Similarly, multifunctional bisketal amide polyisocyanates, formed by the reaction of bisketal amide dithiols, bisketal amide diols, or bisketal amide diamines with polyisocyanates having more than two isocyanate functionalities, are employed in some embodiments of the invention as compounds of Structure II wherein linking group E is (c) to provide branching and/or crosslinking to the polymer matrixes formed therefrom.

In general, the reagents employed, methodology, physical properties of the resulting polymer matrixes, and applications that are addressed using the above described poly(bisketal amide urethane)s wherein linking group E is (b) are the same or similar to those described where linking group E is (c). Some additional variations, however, bear discussion.

In some embodiments, poly(bisketal amide urethane)s, poly(bisketal amide urea)s, or poly(bisketal amide thiocarbamate)s are formed by the reaction of one or more bisketal amide diols, bisketal amide dithiols, or bisketal amide diamines of the invention with one or more bisketal amide diisocyanates or bisketal amide polyisocyanates of the invention. In still other embodiments, one or more bisketal amide diisocyanates or bisketal amide polyisocyanates are reacted with one or more polyols that are not bisketal amide diols, to form a poly(bisketal amide urethane).

Additionally, in some embodiments, one or more isocyanate moieties of the bisketal amide diisocyanates or bisketal amide polyisocyanates of the invention are partially reacted with water to form the corresponding amine group and carbon dioxide. It is known that an isocyanate can be reacted with water to form a primary amine group and carbon dioxide; the primary amine is then available to react with another isocyanate group to form a urea linkage. Thus, in embodiments, one or more bisketal amide diisocyanates or bisketal amide polyisocyanates of the invention are reacted with water to form one or more poly(bisketal amide urethane urea)s via a this known pathway. In some such embodiments, the evolution of carbon dioxide acts as a foaming agent as the reaction progresses, thus providing for a foamed poly(ketal amide urethane urea)s matrix. Water reacts with isocyanate groups to create carbon dioxide gas, which fills and expands cells created during the mixing process, and causes the formation of urea groups.

In still other embodiments, one or more bisketal amide diisocyanates or bisketal amide polyisocyanates are reacted with one or more polyamines or polythiols to form poly(ketal amide urethane urea)s or poly(ketal amide urethane thiocarbamate)s, respectively. Suitable polyamines for forming one or more poly(bisketal amide urethane urea)s of the invention include, for example, hydrazine, ethane-1,2-diamine, 1,6-hexanediamine, but-2-ene-1,4-diamine, Metformin, butane-1,4-diamine, propane-1,2-diamine, benzene-1,3-diamine, 2-methylbenzene-1,3-diamine, 4-chlorobenzene-1,3-diamine, methanediamine, 1,3,5-triazine-2,4,6-triamine, N-(2-aminoethyl)ethane-1,2-diamine, N-(6-aminohexyl)hexane-1,6-diamine, N,N'-bis(2-aminoethyl)ethane-1,2-diamine, N-[2-(3-aminopropylamino)ethyl]propane-1,3-diamine, 4-(3,4-diaminophenyl)benzene-1,2-diamine, spermine (N,N'-bis(3-aminopropyl)butane-1,4-diamine), a polyethyleneimine, a polyoxyalkyleneamine having two or more amine groups, such as those sold under the trade name JEFFAMINE®, (available from the Huntsman Corp. of Salt Lake City, Utah), or any diamine or higher amine compound such as those sold under the trade name ELASTAMINE® (available from the Huntsman Corporation). Suitable polythiol compounds include, for example, dithiols such as ethane-1,2-dithiol, propane-1,3-dithiol, propane-1,2-dithiol, propane-1,1-dithiol, 3-chlorobutane-1,2-dithiol, 1-chlorobutane-2,3-dithiol, 2-chloro-2-methylpropane-1,3-dithiol, butane-1,4-dithiol, butane-1,3-dithiol, hexane-1,6-dithiol, octane-1,8-dithiol, decane-1,10-dithiol, 3-ethoxypropane-1,2-dithiol, 3,4-dimethoxybutane-1,2-dithiol, 2-methyl-5-(1-sulfanylpropan-2-yl)cyclohexane-1-thiol, benzene-1,2-dithiol, benzene-1,3-dithiol, 4-methylbenzene-1,2-dithiol, 4-(4-sulfanylphenyl)benzenethiol, butane-1,4-dithiol, 3-(phenoxy)propane-1,2-dithiol; and trithiols such as ethane-1,1,2-trithiol, propane-1,2,3-trithiol, pentane-1,3,5-trithiol, octane-1,3,8-trithiol, cyclohexane-1,2,4-trithiol, cyclododecane-1,4,8-trithiol, 1,3,5-trithiane-2,4,6-trithiol, nonane-1,5,6-trithiol, benzene-1,2,3-trithiol, benzene-1,3,5-trithiol, 2-methylbenzene-1,3,5-trithiol, and naphthalene-1,2,3-trithiol.

Structure II, Embodiment 4.

The various embodiments described for Embodiment 4 recite compounds and methods used in the synthesis of the compounds of Structure II that result in $\gamma=1$. However, the discussion above regarding order of addition, stoichiometry, and relative reactivity of the compounds employed in the synthesis of the compounds of Structure II apply with equal force to the compounds of Embodiment 4. It will be understood that Embodiment 1 also extends to compounds of Structure II wherein $\gamma$ is 0, 1, or a mixture thereof.

In embodiments where linking group E of Structure II is (d), Structure II is a poly(ketal amide ester) where X is O, poly(ketal amide amide) where X is NH, or poly(ketal amide thioester) where X is S. In general the following discussion relates to the formation of polyester structures. However, it will be understood that polyamide and polythioester adducts are also generally available by employing the corresponding compounds and methodology, or methodology available in the literature, where X of Structure II is NH or S, respectively.

Also, it will be readily understood that similar polymeric structures containing branched or crosslinked morphologies are available by employing analogs of Structure I where the value of α is more than 2; such analogs may be present as part of a reactive mixture to form one or more branched or crosslinked analogs of the polymers of Structure II where linking group E is structure (d).

Poly(ketal amide ester)s are formed by reacting one or more bisketal amide diol with one or more diacids or diesters having structures incorporating moiety H in linking group D of structure (d). The identity of H within linking group D is not particularly limited. For example, bisketal amide diols as described in Structure I, Embodiment 1 are, in embodiments, polymerized with one or more diacids or diesters thereof, such as adipic acid or methyl isophthalate, to give a perfectly alternating copolyester. A nonlimiting, representative example of a bisketal amide diol and a diester is shown in FIG. 1B. Other structural variations are easily envisioned. The polyesters include, in some embodiments, one or more additional diols, or a mixture of diacids or diesters, in order to provide structural variability. Additionally, in some embodiments, triols such as a trisketal amide triol (i.e. where α is 3 in Structure I, Embodiment 1) or another triol, or a higher polyol, a higher poly(ketal amide)ol, a triacid, triester or higher poly(acid) or ester thereof, are incorporated to provide crosslinking or branching sites to the polyester. Other diols or higher polyols, such as any of the those described above, are also incorporated, in embodiments, via one or more copolymerization reactions in conjunction with diacids or diesters and one or more bisketal amide diols of the invention to result in one or more poly(ketal amide ester) copolymers.

In various embodiments, the poly(ketal amide ester)s of the invention have a value of β that is 1. In other embodiments, β is between 2 and 500. In still other embodiments, the value of β is between about 10 and 200. In still other embodiments, the value of β is between about 10 and 100. It will be appreciated that by varying the structure of a diacids or diesters employed in the copolymerization, a wide range of properties are available, for example, hydrophobicity, hydrophilicity, amphiphilic character, tensile strength, solvent resistance, crystallinity, optical transparency, glass transition temperature, and the like.

Non-limiting examples of suitable diacids (or esters of diacids) for use in a polymerization reaction to provide poly(ketal amide esters) and copolymers thereof include aliphatic, cycloaliphatic or aromatic dicarboxylic acids, for example, succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioic acid, dimerized fatty acids, or hydrogenated dimerized fatty acids. The methyl, ethyl, propyl, butyl or phenyl esters of the acids listed above are suitable substitutes for the diacid component, as well as acid anhydrides such as o-phthalic, maleic or succinic acid anhydride or a mixture thereof. Some examples of suitable triacids include 1,3,5-trimethylcyclohexane-1,3,5-tricarboxylic acid, cis or trans aconitic acid, propane-1,2,3-tricarboxylic acid, hemmellitic acid, isocitric acid, and the like.

Copolyesters are also formed where mixtures of diacids and/or diesters are employed, as well as additional diols such as any of the diols described above. Additionally, mixtures of bisketal amide diols are used in some embodiments to form poly(ketal amide ester) copolymers of the invention.

In embodiments, the poly(ketal amide ester)s and copolymers thereof are synthesized using conventional transesterification and/or polymerization catalysts and conditions. The catalyst may be any of the known esterification or transesterification catalysts in general. For example, acidic catalysts such as a toluenesulfonic acid, sulfuric acid, sulfamic acid, or a sulfonic acid are employed in various embodiments. In a preferred embodiment an organometallic catalyst is employed, for example a catalyst based on titanium or tin, such as titanium (IV) tetrabutoxide (Ti(OBu)$_4$), or tin (II) octanoate. The choice of catalyst is not particularly limited within the scope of the invention. In embodiments, reaction conditions are optimized to reach high molecular weight. Such reaction conditions include, in embodiments, the techniques, conditions, and catalysts employed in polyesterification reactions described in U.S. Patent Publication No. 2008/0242721, the entirety of which is incorporated herein by reference.

In other embodiments, the bisketal amide diols or poly(ketal amide)ols of the invention are employed in the ring opening reaction of one or more lactones to form the corresponding poly(ketal amide ester). In such embodiments, β is at least 1 and in many such embodiments β equals 1. Ring opening polymerization of lactones is carried out using one or more catalysts and using reaction conditions suitable for ring opening polymerization. Catalysts and reaction conditions employed in such reactions are any of those used in the art for ring opening reactions of lactones. For example, some ring opening polymerization catalysts are based on transition metals such as zinc, tin, or titanium. Without limiting the species of catalysts or reaction conditions employed, any of the catalysts or reaction conditions described in Hori et al., U.S. Pat. No. 5,516,883 or Schechtman et al., U.S. Pat. No. 5,648,452 are useful. Activated carbon as employed by Endo et al., EP1857484 or organic catalysts employed as described in a web-published article from IBM Company of Armonk, N.Y., at www.almaden.ibm.com/st/chemistry/ps/catalysts/RingOpening/ may be used to affect the ring opening polymerization of lactones using the poly(ketal amide) polyols of the invention as the initiating polyol. The above examples are not limiting as to the type of catalyst or set of reaction conditions that can be employed in a ring opening polymerization of lactones.

Suitable lactones for the ring opening polymerization initiated by one or more poly(ketal amide)ols of the invention include, without limitation, propiolactone, pivalolactone, diketene, dimethyldiketene, β-butyrolactone, 4-butyrolactone, 4-valerolactone, δ-caprolactone, ε-caprolactone, 5-ethenyl-5-methyloxolan-2-one, gluconolactone, glucuronolactone, D-galactonolactone, coumarin, hydrocoumarin, ascorbic acid lactone, α-angelicalactone, 2-acetylbutyrolactone, 6-propyloxan-2-one, 6-ethyloxan-2-one, ribonolactone, arabonolactone, 2-nonalactone, bicyclononalactone, 5-nonalactone, λ-decalactone, pantolactone, 2-dehydropantolactone, 5-butoxolan-2-one, isocrotonolactone, 6-hexyloxan-2-one 5-heptyloxolan-2-one, 5-propyloxolan-2-one, 6-[(b)-pent-2-enyl]oxan-2-one, cocolactone, isocitric lactone, 2-hydroxy-6-methylpyran-4-one, 1-oxacyclododecan-2-one, E-dodecalactone, 1-oxacyclopentadecan-2-one, 1-oxacycloheptadecan-2-one, L-arabino-1,4-lactone, 4-hydroxy-4-methyloxan-2-one, homoserine lactone, 4-methyl-7-propan-2-yloxepan-2-one, and the like.

In one embodiment of a lactone ring opening polymerization, one or more poly(ketal amide)ols of the invention are employed in the ring opening polymerization of SEGETOLIDE™ (available from Segetis, Inc. of Golden Valley, Minn.) or its dimer to form the corresponding ketal functional polyester. The structure of SEGETOLIDE™ and its dimer, as well as methods for the ring opening polymerization of both compounds, are found in U.S. Patent Publication No. 2008/0242721, the contents of which are incorporated by reference herein in their entirety. The methods disclosed therein are suitable, in embodiments, for initiating the ring opening polymerization using the poly(ketal amide) polyols of the invention as initiators.

It will be understood that many additional variations are possible employing the poly(ketal amide)ols of the invention, as well as their poly(ketal amide)thiol and poly(ketal amide) amine analogs. The thermal and environmental stability of one or more poly(ketal amide ester)s or copolymers thereof is excellent. The poly(ketal amide esters) and copolymers based on one or more poly(ketal amide)ols of the invention are, in some embodiments, stable in air up to about 150° C. In other embodiments, the copolyesters of the invention are stable in air up to 200° C. Under an inert atmosphere or under conditions where oxygen is excluded, such as in one layer of a multilayer film, the copolyesters of the invention are stable up temperatures as high as 300° C. The poly(ketal amide esters) and copolyesters of the invention also have, in embodiments, excellent tensile properties that make them useful for a wide variety of commercial applications. Many other embodiments will be readily envisioned; it will be appreciated that the ketal content of the resulting polymers are variable, and a wide range of physical properties such as glass transition temperature, tensile strength, elasticity, and ductility are attainable in various embodiments of the invention.

Structure III.

The invention embodies compounds having one or more fragments corresponding to Structure III:

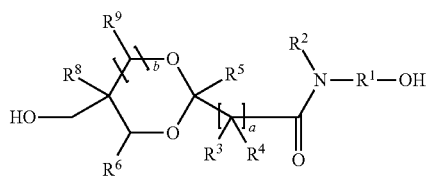

wherein:
$R^1$ is a linear, branched, or cyclic alkyl, alkenyl, or alkynyl group, or an aryl or alkaryl group, wherein the alkyl, alkenyl, aryl, alkaryl groups can have one or more heteroatoms;

$R^2$ is hydrogen or an alkyl group having 1 to 6 carbon atoms and can further include a hydroxyl group;

$R^3$ and $R^4$ are independently hydrogen, halogen, amine, mercapto, phosphate, phosphonooxy, silyl, siloxane, alkynyl, or a linear, branched, or cyclic alkyl or alkenyl groups having 1 to 18 carbon atoms, or an aryl or alkaryl group, wherein the alkyl, alkenyl, aryl, or alkaryl groups can have one or more heteroatoms, and each $R^3$ and $R^4$ may be the same or different;

$R^5$ is hydrogen, alkynyl, or a linear, branched, or cyclic alkyl or alkenyl group having 1 to 18 carbon atoms, or an aryl or alkaryl group, wherein the alkyl, alkenyl, aryl, or alkaryl groups can have one or more heteroatoms;

$R^6$, $R^8$, and $R^9$ are independently hydrogen, halogen, or an alkyl group having between 1 and 6 carbon atoms and optionally one or more heteroatoms;

a is 0 or an integer of between 1 and 12; and b is 0 or 1, wherein b=0 indicates a five membered ring,

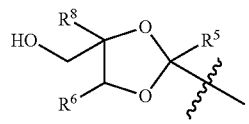

and b=1 indicates a 6 membered ring,

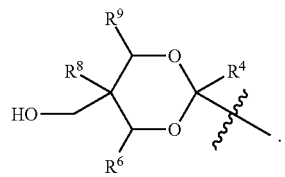

"Heteroatoms" present in the one or more $R^1$, $R^3$, $R^4$, $R^5$, $R^6$, $R^8$, or $R^9$ groups can include, in various embodiments, halogen, nitrogen, oxygen, sulfur, silicon, phosphorus, and the like and can be embodied in a functional group such as amino, carbonate, imide, amide, sulfone, sulfonamide, urethane, mercapto, disulfide, ether, ester, phosphate, phosphonooxy, silane, or silyl functional groups, or a combination thereof.

The compounds of Structure III are ketal amide diols or, where $R^2$ contains an additional OH group, ketal amide triols. It will be understood that the compounds of Structure III are analogs to the compounds of Structure I wherein $R^2$ is $CH_2OH$. In some embodiments, the ketal amide diols and triols of Structure III are made by the reaction of ketal esters with aminoalcohols. The ketal esters are, in embodiments, those described above for Structures I and II. Examples of suitable aminoalcohols include, without any particular limitation, those described in Structure II, Embodiment 3. The methods employed to make the compounds of Structure III include, in general, the same methods employed to make the compounds of Structure I, except that the stoichiometry of the ketal ester to aminoalcohol is, in embodiments, different from that of the ketal ester to diamine. This is because compounds having Structure I represent the reaction product of two moles of ketal ester to one mole of diamine, while compounds of Structure III represent the reaction product of one mole of ketal ester to one mole of aminoalcohol.

In some embodiments of Structure III, $R^1$ is $-(CH_2)_2-$. In other embodiments, $R^1$ is $-(CH_2)_6-$. In some embodiments, a is 0, 1, or 2. In other embodiments, the value of a is 2 and all $R^3$ and $R^4$ are hydrogen. In embodiments, $R^5$ is methyl. In embodiments, b is 0 and $R^6$ and $R^8$ are hydrogen.

In some embodiments, the compounds of Structure III are formed from pyruvic acid (a=0), acetoacetic acid (a=1, $R^3$, $R^4$=H), or levulinic acid (a=2, all $R^3$, $R^4$=H) or an ester thereof with glycerol (b=0, $R^6$, $R^8$=H), 1,1,1-trimethylolpropane (b=1, $R^8$=$CH_2CH_3$, $R^6$, $R^9$=H), or 1,1,1-trimethylolethane (b=1, $R^8$=$CH_3$, $R^6$, $R^9$=H). Levulinic acid is an abundant feedstock that is prepared on an industrial scale by acidic degradation of hexoses and hexose-containing polysaccharides such as cellulose, starch, sucrose, and the like.

The compounds having Structure III are useful in various formulations. The compounds of Structure III are, in some embodiments, soluble in water and lower alcohols and hydrophilic coating formulations. In other embodiments, for example wherein $R^1$ is a long chain alkyl group, for example dodecyl, the compounds of Structure III are soluble in hydrophobic formulations. In yet other embodiments, the various other R groups of Structure III determine solubility in one or more formulations; in some such embodiments, the compounds of Structure III are coalescing solvents, surfactants, solubilizers, interfacial modifiers, and the like.

The compounds having Structure III are, in various embodiments, useful to make a variety of compounds via subsequent reaction pathways. In general, any of the Embodiments listed for Structure I arising from embodiments wherein $R^7$ is $CH_2OH$ are available as analogs of Structure III by employing similar reagents and methodology. For example, the ketal amide diols of Structure III are useful in transesterification reactions to provide diesters, analogous to those of Structure I, Embodiment 2. In other embodiments the ketal amide diols of Structure III are useful in reactions with polyisocyanates to form isocyanate capped compounds, analogous to those of Structure I, Embodiment 3. In other embodiments the ketal amide diols of Structure III are useful in reactions with acrylate, methacrylate, acrylamide, or methacrylamide compounds to form the acrylate functional compounds that are analogs to the acrylate compounds of Structure I, Embodiment 4; subsequent reactions to form the radically or ionically polymerized analogs thereof are also available. In other embodiments the ketal amide diols of Structure III are useful in reactions with allylic compounds to provide allyl capped materials analogous to those of Structure I, Embodiment 5; subsequent reactions to form the polymerized analogs thereof are also available. And in other embodiments the ketal amide diols of Structure III are useful in reactions with epoxy functional compounds, such as epihalohydrins, to provide glycidyl and other epoxy functional compounds analogous to those of Structure I, Embodiment 6; subsequent reactions to form the polymerized analogs thereof are also available.

Structure IV.

The invention embodies compounds having one or more fragments corresponding to Structure IV

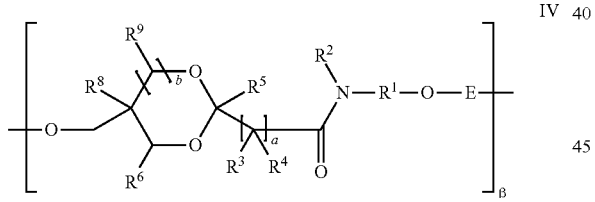

wherein
$R^1, R^2, R^3, R^4, R^5, R^6, R^8, R^9$, X, a, and b are as defined for Structure III;
β is an integer of at least 1; and
E is a linking group as defined for Structure II.

The compounds of Structure IV encompass oligomers of the compounds of Structure III, wherein β is about 2 to 12, as well as polymers wherein β is about 12 to 500, or about 10 to 200, or about 10 to 100. It will be understood that the compounds of Structure IV are analogous to those compounds of Structure II wherein X is O and that arise, in turn, from compounds of Structure I wherein $R^2$ is $CH_2OH$. Thus, analogs of various Embodiments described for Structure II wherein X is O are also available as their Structure IV counterparts by employing similar reagents and methodology in conjunction with the ketal amide diols and triols of Structure III. For example, in embodiments, ketal amide diols of Structure III are useful in making polycarbonate compounds analogous to those of Structure II, Embodiment 1. Employing some ketal amide triol in such a reaction incurs branching or crosslinking. In other embodiments, the ketal amide diols of Structure III are useful in making polyurethane compounds analogous to those of Structure II, Embodiments 2 and 3. And in other embodiments, the ketal amide diols of Structure III are useful in making polyester compounds analogous to those of Structure II, Embodiment 4.

By employing a ketal amide triol in replacement of or partial replacement of a ketal amide diol, branching and/or crosslinking may be incurred. The ketal amide triol is available in embodiments wherein the amine employed to react with the ketal ester is, for example, diethanolamine Structure V.

The invention embodies compounds having one or more fragments corresponding to Structure V:

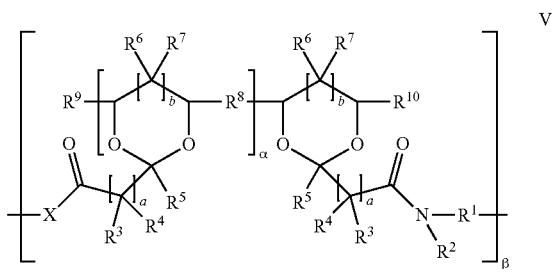

wherein
α is an integer of at least 1;
β is an integer of at least 1;
$R^1$ is a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ may be the same or different for each occurrence;
$R^2$ is hydrogen or an alkyl group having between 1 and 6 carbon atoms;
$R^3, R^4, R^5, R^6$, and $R^7$ are independently hydrogen, a linear, branched, or cyclic alkyl, a linear, branched, or cyclic alkenyl, alkynyl, aryl, or alkaryl; and optionally contains one or more heteroatoms; and $R^3, R^4, R^5, R^6$, and $R^7$ may be the same or different for each occurrence;
$R^8$ is a covalent bond, methylene, ethylene, hydroxymethylene, oxygen, or —$CH_2$—O—$CH_2$— and $R^7$ is the same or different for each occurrence;
$R^9$ and $R^{10}$ are independently hydrogen, a linear, branched, or cyclic alkyl, a linear, branched, or cyclic alkenyl, alkynyl, aryl, alkaryl, or a polymeric moiety; and optionally contains one or more heteroatoms;
X is O or $NR^2$, wherein $R^2$ is as defined above;
a is 0 or an integer of 1 to 12; and
b is 0 or 1, wherein b=0 indicates a five membered ring:

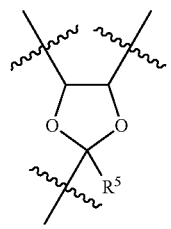

and b=1 indicates a 6 membered ring:

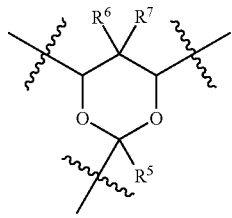

and b may be the same or different for each occurrence.

The invention also embodies compounds having one or more fragments corresponding to Structure V':

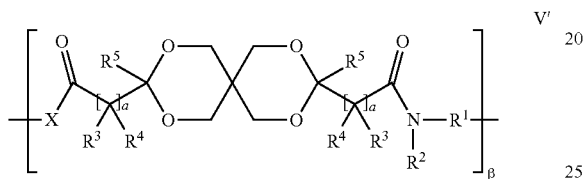

wherein $R^1$, $R^2$, $R^3$, $R^4$, $R^5$, X, a, and β are as defined for Structure V. Structure V' is an analog of Structure V, wherein the tetrol basis for the bisketal functionality is pentaerythritol, $C(CH_2OH)_4$.

The compounds of Structures V and V' are polyketal polyamides. Polyketal polyamides are derived from precursor polyketal compounds; the precursor polyketal compounds are any of those described in International Patent Application No. PCT/US08/79337. The precursor polyketal compounds to Structure V have the structure

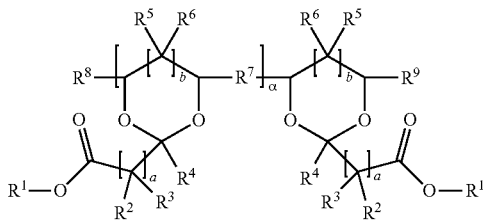

wherein

α is an integer of at least 1;

$R^1$ is hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms; and $R^1$ may be the same or different for each occurrence;

$R^2$, $R^3$, $R^4$, $R^5$, and $R^6$ are independently hydrogen, a linear, branched, or cyclic alkyl, a linear, branched, or cyclic alkenyl, alkynyl, aryl, or alkaryl; and optionally contains one or more heteroatoms; and $R^2$, $R^3$, $R^4$, $R^5$, and $R^6$ may be the same or different for each occurrence;

$R^7$ is a covalent bond, methylene, ethylene, hydroxymethylene, oxygen, or —$CH_2$—O—$CH_2$— and $R^7$ is the same or different for each occurrence;

$R^8$ and $R^9$ are independently hydrogen, a linear, branched, or cyclic alkyl, a linear, branched, or cyclic alkenyl, alkynyl, aryl, alkaryl, or a polymeric moiety; and optionally contains one or more heteroatoms;

a is 0 or an integer of 1 to 12; and b is 0 or 1, wherein b=0 indicates a five membered ring:

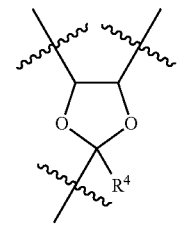

and b=1 indicates a 6 membered ring:

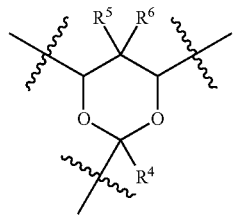

and b may be the same or different for each occurrence.

The precursor polyketal compounds to Structure V' have the structure

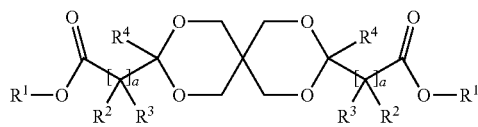

wherein each $R^1$ is independently hydrogen, a metal cation, an organic cation, a linear, branched, or cyclic alkyl, a linear, branched, or cyclic alkenyl, alkynyl, aryl, alkaryl, or an oligomeric or polymeric moiety; and optionally contains one or more heteroatoms;

each $R^2$ and $R^3$ are independently hydrogen, a linear, branched, or cyclic alkyl, a linear, branched, or cyclic alkenyl, alkynyl, aryl, or alkaryl; and optionally contain one or more heteroatoms;

each $R^4$ is independently linear, branched, or cyclic alkyl; linear, branched, or cyclic alkenyl; alkynyl; aryl; or alkaryl; and optionally contains one or more heteroatoms; and each a is independently 0 or an integer of 1 to 12.

Figure 1D:
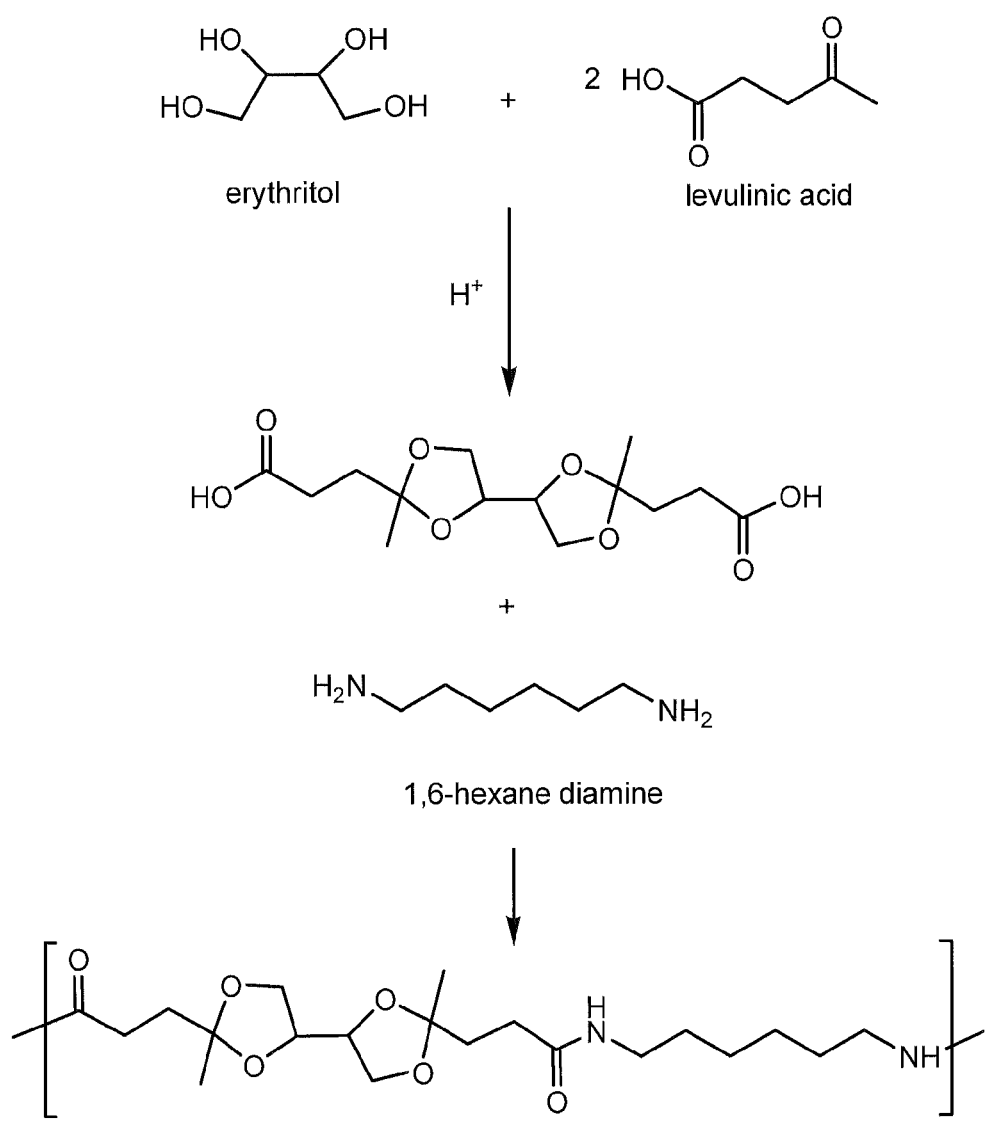

The precursor polyketal compounds to compounds of Structure V are the reaction product of at least two molar equivalents of an oxocarboxylate with one molar equivalent of a first polyol which is a tetrol or higher polyol. The precursor compounds to compounds of Structure V' are bisketal adducts of pentaerythritol, $C(CH_2OH)_4$, with two molar equivalents of a keto acid or ester thereof. Precursor polyketal compounds for the polyketal polyamides having Structure V, and precursor bisketal compounds for polyketal polyamides having Structure V' are collectively referred to herein as "precursor polyketal compounds." One example of a reaction wherein a precursor polyketal compound is formed is shown in FIG. 1D.

In some embodiments of Structures V and V', $R^1$ is —$(CH_2)_3$—. In other embodiments of Structures V and V', $R^1$ is 1,2-cyclohexyl. In still other embodiments of Structures V and V', $R^1$ is —$(CH_2)_6$—. In still other embodiments of Structures V and V', $R^1$ and $R^2$ combine to form a cyclic moiety, for example the residue of piperazine. In some embodiments of Structures V and V', a is 0, 1, or 2. In other embodiments of Structures V, the value of a is 2 and all $R^3$ and $R^4$ are hydrogen; similarly, for Structure V', all $R^2$ and $R^3$ are hydrogen. In embodiments of Structures V and V', $R^4$ is methyl. In embodiments of Structure V, b is 0 and $R^6$ and $R^8$ are hydrogen. In embodiments of Structures V and V', β is 1. In other embodiments of Structures V and V', β is 2 or greater. In embodiments of Structures V and V', β is between about 2 and 500. In other embodiments of Structures V and V', β is about 10 to 200. In other embodiments of Structures V and V', β is about 10 to 100.

In some embodiments, the compounds of Structure I are formed from pyruvic acid (a=0), acetoacetic acid (a=1, $R^3$, $R^4$=H), or levulinic acid (a=2, all $R^3$, $R^4$=H) or an ester thereof with glycerol (b=0, $R^7$=$CH_2OH$, $R^6$, $R^8$=H), 1,1,1-trimethylolpropane (b=1, $R^7$=—$CH_2OH$, $R^8$=$CH_2CH_3$, $R^6$, $R^9$=H), or 1,1,1-trimethylolethane (b=1, $R^7$=—$CH_2OH$, $R^8$=$CH_3$, $R^6$, $R^9$=H). Levulinic acid is an abundant feedstock that is prepared on an industrial scale by acidic degradation of hexoses and hexose-containing polysaccharides such as cellulose, starch, sucrose, and the like.

Some illustrative examples of polyketal precursor compounds that are suitable for use in the synthesis of polyketal polyamides having Structure V and V' are, without limiting the full range of structures as described in the incorporated application:

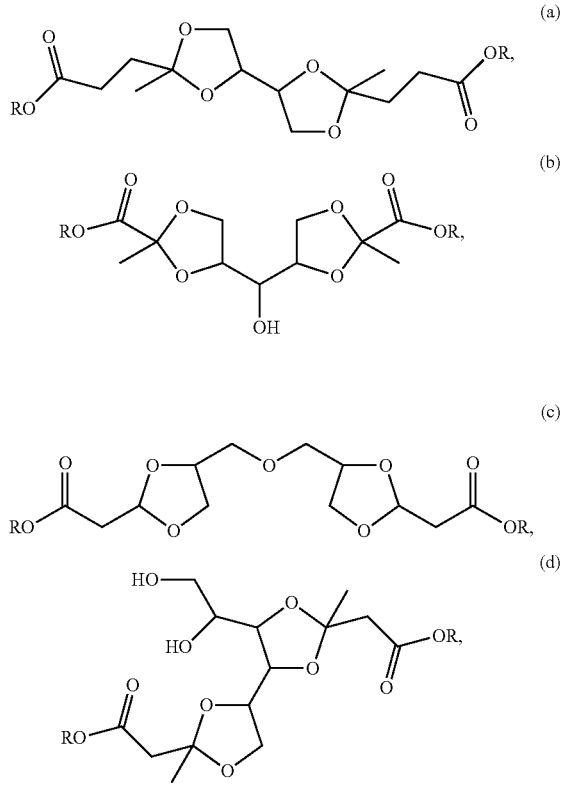

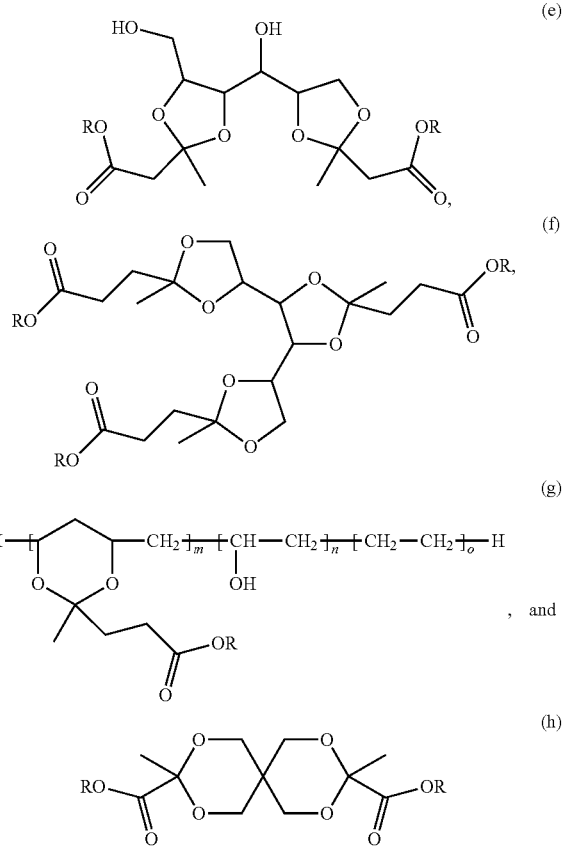

wherein each R is independently hydrogen, a metal cation, an organic cation, a linear, branched, or cyclic alkyl, a linear, branched, or cyclic alkenyl, alkynyl, aryl, or alkaryl, and optionally contains one or more heteroatoms, and m, n, and o are integers of 1 or more. The polyketal precursors to compounds of Structures V and V' are bisketals and higher polyketals of tetrols and higher polyols with two or more equivalents of an oxocarboxylate. In some embodiments, such as in polyketal precursor (a), the polyol employed is erythritol. In other embodiments, such as in polyketal precursors (d), (e), and (f), the polyol employed is sorbitol. In other embodiments, such as in polyketal precursor (c), the polyol employed is diglycerol (a tetrol that is a mixture of glycerol dimers). For compounds of Structure V' the polyol employed is pentaerythritol and polyketal precursor compounds are those such as (h).

As used herein, erythritol and threitol, which are diastereomers, are used interchangeably in various embodiments of the reaction. Similarly, sorbitol and its stereoisomer mannitol are used interchangeably in various embodiments. Where no stereochemistry is indicated in a chemical structure, any stereoisomer may be employed in the embodiments of the invention. Further, any indication of stereochemistry is not meant to limit any particular embodiment to that stereochemistry only; any stereochemical isomer may be used in one or more embodiments of the compounds of the invention.

In some embodiments, a precursor polyketal compound is reacted with one or more diamines or higher polyamines to result in a polyketal polyamide of Structure V or V'. In some such embodiments, X is $NR^2$. In other embodiments, a precursor polyketal compound is polymerized to form the corresponding polyketal polyester by reaction with diol, and then the polyester so formed is subsequently reacted with one or more diamines or higher polyamines to result in a polyketal polyamide of Structure V or V'. In some such embodiments, X is O or $NR^2$ or a mixture of these. In still other embodiments, a polyketal polyamide is subjected to transamidation with a diamine or higher polyamine to result in a new polyketal polyamide structure. In such embodiments, X is $NR^2$. It will be appreciated that copolymers of any of these structures are easily obtained. It will also be appreciated that certain methods of chain extension, such as reacting amino endgroups of a polyketal polyamide of the invention with a diisocyanate, are also available as an extension of any of the synthetic methodology and the unique polyketal polyamide structures of the invention to increase molecular weight, or otherwise effect the physical properties of the polyketal polyamides of the invention.

In forming the polyketal polyamides of the invention from the precursor polyketal compounds, any of the diamines or higher polyamines described for the embodiments of Structure I are suitable. One representative, nonlimiting example of a polyketal polyamide synthetic scheme, starting from a precursor polyketal compound, is shown in FIG. 1D.

One useful method for making the polyketal polyamides of the invention is to form a "nylon salt" of the precursor polyketal compound and a diamine, followed by heating to form a polyketal polyamide of Structure V or V'. The method is carried out, in embodiments of the invention, by starting with a precursor polyketal compound having free acid groups; thus, for example, compounds (a)-(h) wherein R is H. A stoichiometric balance of a precursor polyketal and a diamine or higher polyamine is achieved by forming the 1:1 ammonium salt in aqueous solution of about 10% to 80%, or about 50%, by weight of the combined compounds in water. Stoichiometry is achieved by controlling the pH of the solution by addition of the polyketal precursor or the diamine. Subsequent concentration of the salt to a slurry of about 60% by weight or greater is then achieved by removing some of the water at a temperature of about 100° C. or greater. Concentration is followed by polymerization by heating the concentrated slurry to about 200° C. or greater, or between about 200° C. and 250° C., or to about 210° C. During the polymerization, the temperature is, in some embodiments, raised to about 260° C. to 300° C., or to about 275° C. In some embodiments, a pressure of about 1.7 MPa or greater is employed during part of all of the polymerization reaction by allowing escape of water. No additional catalyst is required using this method. Notably, in such embodiments, all X of Structure II fragments will be $NR^2$— only endgroups of the compounds formed using this method will have X as O.

The polyketal polyamides having Structures V and V' are, in embodiments of the invention, synthesized via amidolysis. In amidolysis, a precursor polyketal ester, for example any of compounds (a)-(h) wherein R is a linear, branched, or cyclic alkyl, a linear, branched, or cyclic alkenyl, alkynyl, aryl, or alkaryl group, is reacted with one or more diamines or higher polyamines to form a polyketal polyamide of Structure V or V'. As with the nylon salt method, in such embodiments, all X of Structure II fragments will be $NR^2$— only endgroups of the compounds formed using this method will have X as O.

Aminolysis is carried out, in some embodiments, by employing one of the techniques known in the literature. For example, methods of reacting of diesters with diamines to form polyamides is described employed in Pryde et al., U.S. Pat. No. 3,223,683; Tashiro et al., U.S. Pat. No. 3,597,376; Brill, U.S. Pat. No. 3,763,234. In embodiments, a polyketal precursor compound and a diamine or higher polyamine are contacted in a vessel in amounts that correspond to a 1:1 molar amount of ester to primary amine groups. The contacted compounds are simply heated to affect the reaction, by allowing for removal of the product alcohol that forms upon reaction of the amines with the ester groups. The compounds are heated to about 200° C., in embodiments between about 200° C. and 250° C., in other embodiments between 250° C. and 300° C., and in still other embodiments to about 300° C. A vacuum is applied, in some embodiments, in order to help drive the reaction to form the polyketal polyamide by facilitating removal of the alcohol byproduct of the aminolysis reaction, which corresponds to the ester group. In some embodiments, an inert solvent is employed to facilitate the reaction; for example, benzene, toluene, xylene, hexane, octane, chlorinated aliphatic hydrocarbons such as 1,1,2-trichloroethane, and the like may be used in various embodiments of the reaction. In some embodiments, for example where the amine is a liquid at room temperature, it is preferable to employ no solvent.

In some embodiments, a Lewis acid is employed as a catalyst in the aminolysis reaction to form the polyketal polyamides of the invention. Examples of suitable Lewis acids include, in embodiments, antimony trichloride, aluminum chloride, antimony trifluoride, ferric chloride, antimony pentachloride, niobium pentachloride, tantalum tetrachloride, titanium tetrachloride, boron trifluoride, antimony pentafluoride, stannic fluoride, aluminum bromide, thallium trichloride, uranyl nitrate, uranium tetrachloride, uranyl acetate, uranium oxides such as $UO_2$, and the like. In embodiments where a Lewis acid catalyst is employed, the reaction proceeds at temperatures as low as about 250° C., or between about 100° C. and 250° C., or even as low as about 80° C. to 100° C.

In other embodiments, aminolysis can be carried out using mild conditions when organic catalysts are employed. For example, Sabot et al., *Tetrahedron Letters* 48 (2007) 3863-6 disclose solvent-free aminolysis of monoesters with monoamines catalyzed by 1,5,7-triazabicyclo[4.4.0]dec-5-ene, or TBD, as low as room temperature. In the reactions of the invention, the addition of heat is required in order to reach appreciable molecular weight, because of the general tendency of polyamides to form high melting, very hard solids even with a low degree of polymerization such as 2-3; raising the temperature allows a higher degree of polymerization to be reached than the same reaction at ambient temperatures.

However, we have found, surprisingly, that lower temperatures than those required to synthesize polyamides in any of the previously described techniques may be employed and similar degrees of polymerization are reached, in embodiments, to those reached by employing the high temperatures to synthesize polyketal polyamides described above. For example, a polyketal polyamide is formed, in embodiments, by contacting a bisketal ester with a diamine at molar ratios of about 2:1 to about 1:2, or in some embodiments about 3:2, in other embodiments about 1:1, and in still other embodiments about 1.1:1 to 1.2:1 [bisketal ester]:[diamine]; and adding TBD in an amount of about 200-2000 ppm, or in some embodiments about 750-1000 ppm, based on the mass the combined reagents, to form a reaction mixture. In some embodiments, one or more inert solvents such as toluene, hexane, and the like are added to the reaction mixture; in some embodiments, no solvent is added to the reaction mixture. In embodiments, no heat is added to the reaction mixture; in other embodiments, the reaction mixture is heated to a temperature of about 20° C. to 200° C.; in other embodiments, the reaction mixture is heated to a temperature of about 70° C. to 150° C.; in other embodiments, the reaction mixture is heated to a temperature of about 120° C. to 140° C. The reaction of the bisketal ester with the diamine is carried out for about 1 minute to 50 hours, in some embodiments about 1 hour to 45 hours, in other embodiments about 10 to 40 hours, and in still other embodiments about 30 to 40 hours.

It will be understood that the method of the invention is not limited by the nature of either the diester or the diamine employed in the reaction. That is, the method is employed in various embodiments with non-ketal based diesters in addition to the polyketal precursor compounds that are employed in various embodiments in the synthesis of polyketal polyamides having Structure V and V'. The mildness of the reaction conditions and the favorable polyamide products of narrow polydispersity are advantageous in many polyamide syntheses, some embodiments of which include the synthesis of the polyketal polyamides of the invention.

The result of the reaction carried out using the method of the invention is the formation of a polyamide having a degree of polymerization of about 2 to 500, or about 10 to 200, or about 10 to 100 depending on reaction stoichiometry, temperature, and reaction time. The polymers formed by the method of the invention are characterized by a narrow polydispersity. For example, for polymers having a molecular weight of about 2000 to 10,000 g/mol, polydispersity index (the ratio of weight average molecular weight to number average molecular weight) is, in embodiments, about 1 to 3. In other embodiments, the polydispersity index is about 1.7 to 1.8.

The polymers formed by the method of the invention are, in embodiments, subjected to further reactions to increase molecular weight or add functionality to the resulting polymer. For example, where a stoichiometric excess of diamine is contacted with bisketal ester, such that amine endgroups are formed in the resulting polymer, the polymer is, in embodiments, additionally contacted with a diisocyanate to form polyurea linkages between chains initially formed by aminolysis. In another example, where a stoichiometric excess of bisketal ester is contacted with a diamine such that ester endgroups are formed in the resulting polymer, the polymer is, in embodiments, additionally contacted with a diol to form polyester linkages between chains initially formed by aminolysis.

In a related embodiment, aminolysis of a polyketal polyester is carried out to form the polyketal polyamides of the invention. In such embodiments, the starting ester functionality is a residue of a polyketal polyester instead of a precursor polyketal compound. Polyketal polyesters, copolyesters thereof, and their synthesis are described in International Patent Application No. PCT/US08/79337 and have at least one repeat unit corresponding to the structure

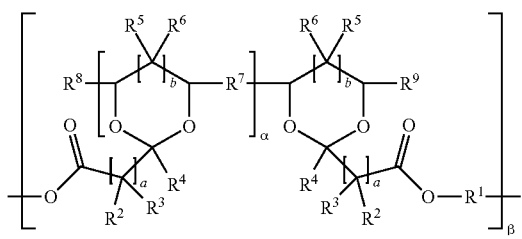

wherein
R$^1$ is a linear, branched, or cyclic alkyl, a linear, branched, or cyclic alkenyl, alkynyl, aryl, alkaryl, or an oligomeric or polymeric moiety; and optionally contains one or more heteroatoms; and R$^1$ is the same or different for each occurrence;

R$^2$, R$^3$, R$^4$, R$^5$, and R$^6$ are independently hydrogen, a linear, branched, or cyclic alkyl, a linear, branched, or cyclic alkenyl, alkynyl, aryl, or alkaryl; and optionally contains one or more heteroatoms; and R$^2$, R$^3$, R$^4$, R$^5$, and R$^6$ is the same or different for each occurrence;

R$^7$ is a covalent bond, methylene, ethylene, hydroxymethylene, oxygen, or —CH$_2$—O—CH$_2$— and R$^7$ is the same or different for each occurrence;

R$^8$ and R$^9$ are independently hydrogen, a linear, branched, or cyclic alkyl, a linear, branched, or cyclic alkenyl, alkynyl, aryl, alkaryl, or a polymeric moiety; and optionally contains one or more heteroatoms;

a is 0 or an integer of 1 to 12; and b is 0 or 1 wherein b=0 indicates a five membered ring,

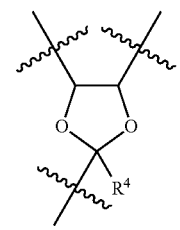

b=1 indicates a 6 membered ring,

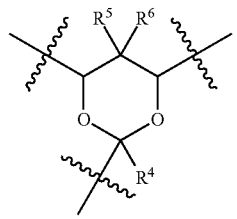

and b may be the same or different for each occurrence;

α is an integer of at least 1; and

β is an integer of at least 1.

Other polyketal polyesters additionally have, in embodiments, the structure

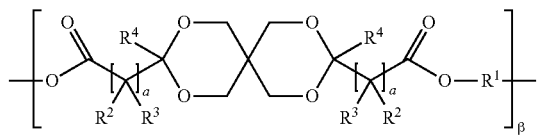

wherein
R$^1$ is a linear, branched, or cyclic alkyl, a linear, branched, or cyclic alkenyl, alkynyl, aryl, alkaryl, or an oligomeric or polymeric moiety; and optionally contains one or more heteroatoms; and R$^1$ is the same or different for each occurrence;

R$^2$ and R$^3$ are independently hydrogen, a linear, branched, or cyclic alkyl, a linear, branched, or cyclic alkenyl, alkynyl, aryl, or alkaryl; and optionally contains one or more heteroatoms; and R$^2$ and R$^3$ are the same or different for each occurrence;

$R^4$ is a linear, branched, or cyclic alkyl, a linear, branched, or cyclic alkenyl, alkynyl, aryl, or alkaryl; and optionally contains one or more heteroatoms; and $R^4$ is the same or different for each occurrence;

a is 0 or an integer of 1 to 12; and

β is an integer of at least 1.

These structures are also described in International Patent Application No. PCT/US08/79337.

The polyketal polyesters are the polyester analogs of the polyketal precursor compounds described above. They are formed, in embodiments, by polyesterification techniques, employing precursor polyketal compounds and diols, as described in International Patent Application No. PCT/US08/79337. Aminolysis of the polyketal polyesters is generally carried out according to the techniques described above and employs the same catalysts, solvents or lack thereof, and reaction conditions. In embodiments where no solvent is employed to affect the reaction, the polyester is heated to its melt temperature in the presence of a diamine or higher polyamine in order to affect the aminolysis. In such embodiments, no catalyst is required to affect the reaction and the reaction proceeds smoothly to high molecular weights using conventional methods. In some such embodiments, application of vacuum during the reaction is useful for removing diol molecules that are the byproduct of the aminolysis.

The aminolysis reaction between diamines or higher polyamines and polyketal polyesters is, in some embodiments, only a partial aminolysis. In such embodiments, the polyamine reacts with the polyketal polyester to form a polyketal poly(ester amide), or a compound of Structure V or V' wherein X is O or a mixture of O and $NR^2$. How far the aminolysis reaction proceeds to complete the removal of diol and form a polyketal polyamide with very few or no fragments wherein X is O is dependent, in embodiments, upon both reaction conditions and stoichiometry of amine to ester functionality. For example, where less than 100 mole % of amine groups are added to an aminolysis reaction, compared to ester groups, the reaction proceeds to form a polyketal poly(ester amide). In some embodiments, about 99 mole % to 95 mole % of amine groups are added as compared to ester groups. In other embodiments, about 95 mole % to 80 mole % of amine groups are added as compared to ester groups. In still other embodiments, as low as 50% of amine groups are added compared to ester groups. In general, as the mole % of amine groups are lowered with respect to ester groups, the glass transition temperature of the resulting copolymer is observed to become lower. Thus, glass transition temperatures of amide-ester copolymers of the invention are targeted based on the desired end use.

In other embodiments, the polyketal polyamides of the invention are synthesized using transamidation of an amide and a polyamine. For example, a polyketal polyamide is, in some embodiments, synthesized employing one of the above-described methods; the polyketal polyamide is then subjected to transamidation with a second diamine or higher polyamine using techniques described, for example, in Stahl et al., U.S. Pat. No. 7,154,004 to arrive at a polyketal polyamide having an polyamino fragment attributable to the second polyamine. In other embodiments, a precursor polyketal ester, for example any of compounds (a)-(h) wherein R is a linear, branched, or cyclic alkyl, a linear, branched, or cyclic alkenyl, alkynyl, aryl, or alkaryl group, is reacted with a monoamine such as 1-aminohexane, 1-propanamine, N-butylhexan-1-amine, or any other primary or secondary alkyl or alkenyl monoamine, to form a precursor polyketal amide; the polyketal amide is then subjected to transamidation with a diamine or higher polyamine to result in a polyketal polyamide of the invention. In embodiments, a metal catalyst based on Sc, Ti, or Al is employed to catalyze the transamidation reaction. In some embodiments, the catalyst employed is $Sc(OTf)_3$; in other embodiments, $Ti(NMe_2)_4$ or $Al_2(NMe_2)_6$ are used. The reactions are preferably carried out at temperatures of about 250° C. or less. An inert solvent, such as toluene, is employed in some embodiments; in other embodiments, no solvent is employed to affect the transamidation reaction.

By using any of the above methods described to make compounds having Structures V and V', a wide range of copolymers are easily formed. A mixture of precursor polyketal compounds are used, in embodiments, in a single reaction to form a polyketal copolyamide. Similarly, a mixture of diamines or higher polyamines are employed in other embodiments. In some embodiments, combining one or more precursor polyketal compounds with one or more diacids that are not precursor polyketal compounds in a "nylon salt" reaction together with one or more diamines or higher polyamines results in polyketal copolyamides. Suitable diacids that are employed in such reactions include, for example, aliphatic, cycloaliphatic or aromatic dicarboxylic acids such as succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioc acid, dimerized fatty acids, or hydrogenated dimerized fatty acids.

Similarly, one or more precursor polyketal compounds are combined with one or more diesters that are not precursor polyketal compounds in an aminolysis reaction together with one or more diamines or higher polyamines to result in various polyketal copolyamides. Any of the known ester moieties, such as the methyl, ethyl, propyl, butyl or phenyl esters of any of the diacids listed above, are suitable for copolymerization with precursor polyketal compounds and polyamines. In some embodiments, it is advantageous to provide an ester group that corresponds to an alcohol byproduct that is easily removed from a reaction vessel during the reaction, in order to help drive the reaction to completion. For example, in embodiments where vacuum and/or heat is employed in an aminolysis reaction, it is advantageous to employ an ester having an alcohol byproduct that boils at or below the temperature of the reaction to facilitate removal of the alcohol by evaporation.

Combining one or more polyketal polyesters with a second polyester in an aminolysis reaction together with a diamine or higher polyamine also results in a polyketal copolyamide. Combining one or more polyketal polyesters with one or more diesters that are not precursor polyketal compounds in an aminolysis reaction together with one or more diamines or higher polyamines results in various polyketal copolyamides. And combining one or more precursor polyketal compounds with one or more polyesters that are not polyketal polyesters in an aminolysis reaction together with one or more diamines or higher polyamines results in various polyketal copolyamides. Transamidation similarly lends itself to a wide range of copolyamide structures, as will be easily envisioned. A wide range of copolyamides is available using the described techniques, resulting in materials with a wide range of properties including tensile strength, ductility, thermal stability, and the like.

Crosslinked or branched analogs of the polyketal polyamides of the invention are readily formed by employing a major proportion of precursor polyketal compounds or polyesters thereof, diacids or esters thereof, and diamines with a minor proportion of, in embodiments, tricarboxylic acid or higher polyacid or ester thereof, or triamine or higher polyamine in any of the polyamide forming reactions described above. The precursor polyketal compounds are, in some embodiments, trisketal compounds or precursor polyketal compounds of higher functionality.

Additional functionality and increase in molecular weight of the polyketal polyamides are also realized, in embodiments, by providing additional reagents to the polyketal polyamides during or after the polymerization methods described above. For example, by including a diol or higher polyol into an amidation reaction between a precursor polyketal compound and a diamine or higher polyamine, residual ester endgroups are taken up by transesterification reactions and ultimate chain length is increased; a polyketal poly(ester amide) is thereby formed. Similarly, by adding diisocyanate at the end of a reaction in which a polyketal polyamide is formed having amino endgroups, chain extension by formation of urea groups results in a polyketal poly (amide urea). Many other variations are possible, such as reacting residual endgroups of a polyketal polyamide to provide reactive acrylate, allyl, or oxirane functionalities that in turn can be polymerized to provide chain extension, crosslinking, or branching. It will be recognized that many conventional techniques can be employed to provide further variations in structure and molecular weight of the polyketal polyamides of the invention.

The amide-functional polymers and copolymers of the invention have unique and useful properties that enable their use in a wide range of applications. In various embodiments, the amide-functional polymers and copolymers of the invention have good transparency, high levels of stiffness, high levels of hardness, good creep resistance, good dimensional stability, little processing shrinkage, good heat distortion properties, high melt viscosity, high melt strength, ability to alloy with other polyamides that are amorphous or semicrystalline to achieve a wide additional range of properties, low water uptake, good surface properties, good barrier properties, resistance to nonpolar solvents, good impact strength, ductility at moderate temperatures, good weatherability, and stress-crack resistance to polar solvents.

Amide-functional polymers and copolymers incorporating one or more repeat units attributable to Structures I-V are useful in a wide variety of industrially useful and significant applications. The amide-functional polymers and copolymers of the invention are, in embodiments, used in blends, optionally obtained by reactive extrusion. Blends include blends of various species of the amide-functional polymers and copolymers of the invention as well as blends with such polymers as aliphatic/aromatic copolyesters, as for example polybutylene terephthalate adipate (PBTA), polybutylene terephthalate succinate (PBTS), and polybutylene terephthalate glutarate (PBTG); biodegradable polyesters such as polylactic acid, poly-ε-caprolactone, polyhydroxybutyrates such as poly-3-hydroxybutyrates, poly-4-hydroxybutyrates and polyhydroxybutyrate-valerate, polyhydroxybutyrate-propanoate, polyhydroxybutyrate-hexanoate, polyhydroxybutyrate-decanoate, polyhydroxybutyrate-dodecanoate, polyhydroxy-butyrate-hexadecanoate, polyhydroxybutyrate-octadecanoate, and polyalkylene succinates and their copolymers with adipic acid, lactic acid or lactide and caprolactone and their combinations, and the like; polystyrene and copolymers thereof; polyurethanes; polycarbonates; polyamides such as Nylon 6 and Nylon 6,6; polyolefins such as polyethylene, polypropylene, and copolymers thereof; or any other industrially useful polymeric compounds. Blends also include, in some embodiments, composites with gelatinized, destructed and/or complexed starch, natural starch, flours, and other materials of natural, vegetable or inorganic origin. The amide-functional polymers and copolymers of the invention are, in some embodiments, blended with polymers of natural origin, such as starch, cellulose, chitosan, alginates, natural rubbers or natural fibers (such as for example jute, kenaf, hemp). The starches and celluloses can be modified, such as starch or cellulose esters with a degree of substitution of between 0.2 and 2.5, hydroxypropylated starches, or modified starches with fatty chains, among others.

In some embodiments, alloys of two or more polyamide polymers or copolymers, including at least one polymer having one or more repeat units attributable to Structures I-V, are formed in blends thereof. The term "alloy" means a blend wherein the two or more polymers have a chemical interaction evidenced by a shift in glass transition temperatures as described in M. Kohen, ed., "Nylon Plastics Handbook", © 1995 by Carl Hanser Verlag, Munich, Germany, p. 380-1. The polyamide blended with the at least one polyamide or copolyamide of the invention is, in embodiments, a second polyamide or copolyamide of the invention, or some other polyamide that is amorphous or semicrystalline.

The amide-functional polymers and copolymers according to the invention, and blends of thereof, possess properties and values of viscosity that render them suitable for use, by appropriately adjusting the molecular weight, in numerous practical applications, such as films, injection-molded products, extrusion coated products, fibers, foams, thermoformed products, extruded profiles and sheets, extrusion blow molding, injection blow molding, rotomolding, stretch blow molding and the like.

In the case of films, production technologies like film blowing, casting, and coextrusion can be used. Moreover such films can be subject to monoaxial or biaxial orientation in line or after film production. It is also possible that the stretching is obtained in presence of an highly filled material with inorganic fillers. In such a case, the stretching can generate micropores and the so obtained film can be suitable for hygiene applications.

The amide-functional polymers and copolymers according to the invention are suitable for the production of films. A "film" is defined, for the purposes of the invention, as a sheet type material that is flexible to e.g. bending and is between about 1 μm to 5 mm thick. Films employing the amide-functional polymers and copolymers of the invention are, in embodiments, one-directional or two-directional, single layer or multilayer, and employ the polyketal polymers of the invention as a single component or in a blend with other materials, as described above. The films are useful for various applications including agricultural mulching films; printable films for graphics or text; cling films (extensible films) for foodstuffs, films for bales in the agricultural sector and for wrapping of refuse; shrink films such as for example for pallets, mineral water, six pack rings, and so on; bags and liners such as for collection of refuse, holding foodstuffs, gathering mowed grass and yard waste, and the like; thermoformed single-layer and multilayer packaging for foodstuffs, such as for example containers for milk, yogurt, meat, beverages, etc.; and in multilayer laminates with layers of paper, plastic materials, aluminum, metalized films for a wide variety of applications.

The amide-functional polymers and copolymers of the invention are also useful for coatings that form a layer on top of a film, an article, and the like. Coatings of the invention are applied, in embodiments, by extrusion coating, die coating, slot coating, brush coating, spray coating, or any other generally known technique employed in the coating industry. Coatings employing the amide-functional polymers and copolymers of the invention are useful as protective coatings, paint components, adhesives or glues, barrier layers, and the like. The coatings of the invention are applied, in embodiments, with or without additional solvent(s), such as coalescing solvents, and with our without additives such as UV blocking agents, antibacterial agents, colorants, fillers, and the like. The coatings of the invention are, in some embodiments, crosslinked after application.

The amide-functional polymers and copolymers of the invention are also useful in forming articles. An "article", as defined for the purposes of the invention, includes objects that are be rigid or flexible; that exist as standalone objects or as part of an assembly or laminate; and that include one or more amide-functional polymers and copolymers of the invention or a blend thereof, optionally with one or more additional materials. Some examples of useful articles that include amide-functional polymers and copolymers of the invention are punnets for foodstuffs, 1-beams for construction, casings for e.g. pens, computer screens, and the like; parts for automobile construction, table tops, and the like; decorative items such as lamp parts, jewelry, vases, architectural features, and the like; children's toys; drink bottles; and many other articles. The invention is not particularly limited in terms of what articles may be formed employing the amide-functional polymers and copolymers of the invention.

Articles that can be formed using the amide-functional polymers and copolymers of the invention include, in various embodiments, loose covers for optical wave guides, e.g. loose jacketing; measuring and pressure reservoirs for liquids and gases, e.g. filter bowls; pump casings, styled articles such as toiletry, glasses frames, handles, and the like; shaped articles for medical and biological apparatus, barrier layers in foodstuff packaging, and the like. The transparent nature of many of the amide-functional polymers and copolymers of the invention make them ideally suited for many useful applications where tough polyamide properties are required and transparency is also desirable or required.

Other examples of articles that can be formed using the amide-functional polymers and copolymers of the invention are foamed articles. Foaming of polyurethanes is discussed above; these techniques and others generally known in the industry are used, in embodiments, to form foamed articles from the various amide-functional polymers and copolymers of the invention. Foamed articles include both rigid and flexible foams. Some examples of useful foamed materials include cushions for automobile seats, interior or exterior furniture, and the like; foamed or foamable beads for the production of pieces formed by sintering; foamed blocks made up of pre-foamed particles; foamed sheets, thermoformed foamed sheets, and containers obtained therefrom for the packaging of foodstuffs.

Articles also include fibrous articles. Examples of fibrous articles include standard scale fibers, microfibers, nanofibers, and composite fibers. Composite fibers have, in embodiments, a core constituted by a rigid polymer such as PLA, PET, PTT, etc. and an external shell made with one or more polyketal polymers of the invention; other composite fibers have various section configurations (from round to multi-lobed). Fibers also include flaked fibers, woven and non-woven fabrics or spun-bonded or thermobonded fabrics for the sanitary sector, the hygiene sector, the agricultural sector, georemediation, landscaping and the clothing sector.

EXPERIMENTAL SECTION

General Experimental Procedures

Gas Chromatography (GC) and GC-Mass Spectrometry (GC-MS) Analyses

GC and GC-MS analyses are carried out according to standard laboratory techniques. Standard GC analysis is carried out by flame ionization detector. The integration peak areas of all peaks in the chromatogram are automatically calculated by an Agilent Technologies ChemStation (Agilent Technologies of Santa Clara, Calif.). The calculated peak areas are reported as a weighted percent (expressed as abundance) relative to the area of all of the detected peaks in the chromatogram (total area). These calculations are used elsewhere herein to report all percent yield, percent yield "based on theoretical", percent yield "as determined by GC-MS", and any other percent reaction statements resulting from GC or GC-MS analyses.

Gel Permeation Chromatography (GPC)

Molecular weight determination is carried out by GPC using a Waters Isocratic HPLC System (from Waters Corp. of Milford, Mass.) that includes a Waters 2414 Differential Refractometer, Waters 1515 Isocratic Pump, Waters 717 Autosampler, and Waters Column Heater and Empower GPC Software for molecular weight analysis. For samples with an expected molecular weight of 20,000-400,000 Daltons a PLgel Mixed D 5 µm column, 300×7.5 mm, is used; for samples with an expected molecular weight of less than 20,000 a PLgel Mixed E 5 µm column, 300×7.5 mm, is used; and for samples with an expected molecular weight between 20,000 and 2,000,000 a PLgel Mixed C 5 µm column, 300×7.5 mm is used. All columns were obtained from Polymer Labs, a division of Varian Inc. of Palo Alto, Calif.

All samples are analyzed using either tetrahydrofuran (THF) or dimethyl formamide (DMF) mobile phase. The THF mobile phase is employed at 1 ml/min and weight average molecular weight ($M_w$) is calculated against polystyrene narrow molecular weight standards. The DMF mobile phase with 0.05M lithium bromide is employed at 1 ml/min and weight average molecular weight ($M_w$) is calculated against polymethylmethacrylate narrow molecular weight standards.

Differential Scanning calorimetry (DSC)

Glass transition temperature ($T_g$) is determined by following ASTM D-3418, employing a TA Q200 instrument with refrigerated cooling and TA Thermal Advantage software (from TA Instruments of New Castle, Del.). Homogeneous samples of between about 5 and 15 mg are prepared, weighed, placed in a Tzero pan and crimped with a Tzero lid, (pan and lid both available from TA Instruments). The mass of the sample is entered into the Thermal Advantage software. The thermal analysis is carried out according to one or the sets of parameters below:

Cycle 0: Equilibrate at −40° C.
Isotherm for 2.00 minutes
End of Cycle 0
Cycle 1: Ramp 10° C./min to 240° C.
Isotherm for 2.00 minutes
End of Cycle 1
Cycle 2: Ramp 10° C./min to −40° C.
Isotherm for 2.00 minutes
End of Cycle 2
Cycle 3: Ramp 10° C./min to 240° C.
Isotherm for 2.00 minutes
End of Cycle 3
Repeat at Cycle 0
Cycle 0: Equilibrate at −80° C.
Isotherm for 2.00 minutes
End of Cycle 0
Cycle 1: Ramp 10° C./min to 200° C.
Isotherm for 2.00 minutes
End of Cycle 1
Cycle 2: Ramp 10° C./min to −80° C.

Isotherm for 2.00 minutes
End of Cycle 2
Cycle 3: Ramp 10° C./min to 200° C.
Isotherm for 2.00 minutes
End of Cycle 3
Repeat at Cycle 0

Synthesis of Certain Starting Materials

The following ketal compounds were synthesized for further reactions in the Examples.

EtLGK

The glycerol ketal of ethyl levulinate, 1,3-dioxolane-2-propanoic acid, 4-(hydroxymethyl)-2-methyl, ethyl ester, was prepared according to the procedure set forth in Example 2 of International Patent Application No. PCT/US08/79083. The ketal will be referred to as "EtLGK".

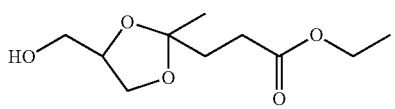

EtLGK

EtBLEK

The erythritol bisketal of ethyl levulinate, [4,4'-bi-1,3-dioxolane]-2,2'-dipropanoic acid, 2,2'-dimethyl-,2,2'-diethyl ester, was prepared and purified according to the procedure of Example 12 of International Patent Application No. PCT/US08/79337. The bisketal will be referred to as "EtBLEK".

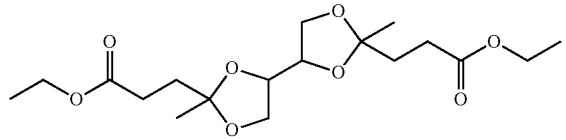

EtBLEK

Et BLPK

The pentaerythritol bisketal of ethyl levulinate was synthesized according to the procedure set forth in Example 7 of International Patent Application No. PCT/US08/79337. The bisketal will be referred to as "EtBLPK".

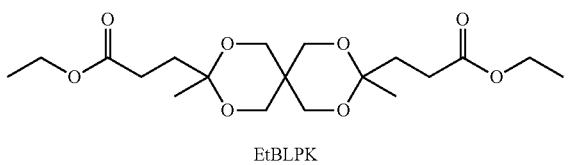 [SMILES: CCOC(=O)CCC1(C)OCC2(CO1)COC(C)(CCC(=O)OCC)OC2]

EtBLPK

EtBPEK

The bisketal of erythritol and ethyl pyruvate was synthesized as follows. A 1000 mL, three neck round bottom flask was charged with 122.12 g (1.00 mol) erythritol (obtained from Cargill of Wayzata, Minn.), 348.36 g (3.00 mol) ethyl pyruvate (obtained from the Sigma-Aldrich Company of St. Louis, Mo.), and 235 g toluene (obtained from Fisher Scientific of Waltham, Mass.). The flask was equipped with a thermocouple, mechanical stirrer, and Dean-Stark trap with an attached condenser. A bubbler was attached to the top of the condenser of the Dean Stark trap to release positive pressure in the flask.

The reaction was stirred and heated to 110° C. using a heating mantle. Upon reaching 110° C., 29 μL of concentrated sulfuric acid (obtained from the Sigma-Aldrich Company of St. Louis, Mo.) was quickly added by metered micropipette. A liquid was observed to collect in the Dean-Stark trap; the trapped liquid separated into two layers upon cooling. The top layer was presumed to be toluene, and the bottom layer presumed to be water. The top layer was allowed to return to the flask while the bottom layer continued to collect in the Dean-Stark trap. Heating and stirring were continued for approximately 5 hours, at which time ⅔ the theoretical amount of water had been collected in the Dean-Stark trap. The contents of the flask were allowed to cool to room temperature. The cooled contents of the flask were analyzed by GC-MS. The GC trace showed about 10% yield of the bisketal structure of erythritol and ethyl pyruvate, referred to as "EtBPEK". The toluene was stripped from the contents of the flask by rotary evaporation.

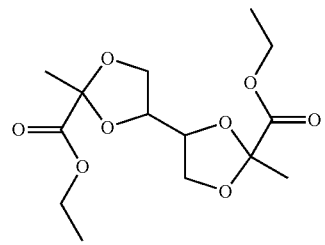

EtBPEK

EtBLDK

The bisketal of diglycerol (3,3'-oxybis-1,2-propanediol) and ethyl levulinate was prepared according to the procedure of Example 8 of International Patent Application No. PCT/US08/79337. The bisketal will be referred to as "EtBLDK".

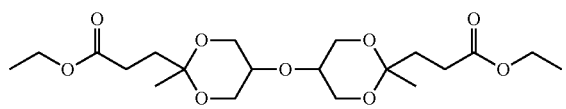

EtBLDK

EtBAEK

The bisketal of erythritol and ethyl acetoacetate was prepared according to the procedure of Example 11 of International Patent Application No. PCT/US08/79337. The bisketal will be referred to as "EtBAEK".

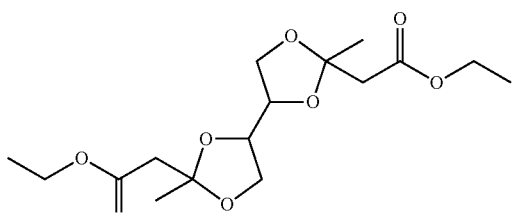

EtBAEK

Example 1

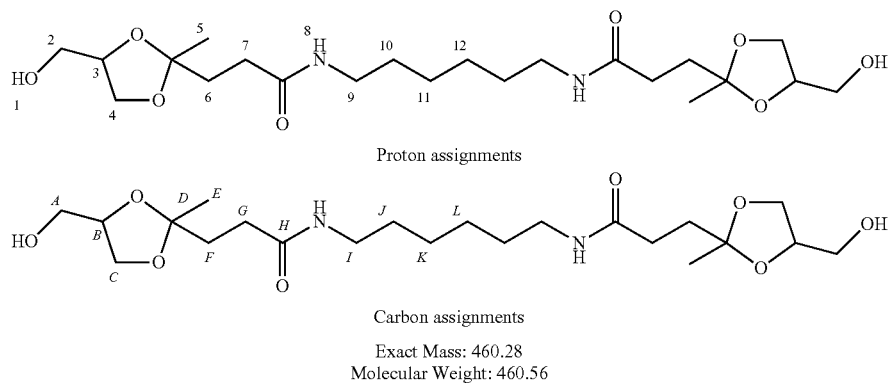

Proton assignments

Carbon assignments

Exact Mass: 460.28
Molecular Weight: 460.56

A flame-dried 250 mL four-necked flask was cooled under a stream of nitrogen and equipped with a Dean-Stark apparatus. To this flask was added 33.5 g (153 mmol) EtLGK and 8.95 g (77 mmol) 1,6-hexamethylene diamine (obtained from Acros Organics of Geel, Belgium). The reaction mixture was heated to 200° C. for 2.5 hours, after which time 7 mL of a liquid accumulated in the Dean Stark trap (theoretical yield of ethanol=8.8 mL). The liquid was removed and vacuum of about 5 torr was applied to the reaction mixture for 3 hours. The reaction mixture was then allowed to cool to ambient temperature. Upon cooling, 0.132 g of a yellow viscous oil was isolated for characterization.

IR (cm$^{-1}$)=3306 (OH, NH amide), 2935 (CH aliphatic), 1647 (C=O amide). $^1$H NMR (CDCl$_3$) δ (ppm)=6.15, 5.96 (2H, br s, 8); 4.20 (2H, m, 3); 0.88 (4H, m, 4); 3.86 (2H, t, 1); 3.64 (4H, m, 2); 3.21 (4H, m, 9); 2.29 (4H, m, 7); 2.11 (2H, m, CH$_2$ 12); 1.98 (4H, m, 6); 1.48 (4H, br t, 10); 1.36, 1.32 (6H, s, 5); 1.32 (4H, s, 11). $^{13}$C NMR (CDCl$_3$) δ (ppm)=174.24, 173.26 (C=O amide, H); 110.36, 110.04 (D); 77.10, 76.49 (B); 66.26, 65.50 (C); 63.08, 62.11 (A); 39.17, 39.09 (G); 34.96, 34.38 (F); 31.38, 31.07 (E); 29.34, 29.15 (I); 25.96 (J); 24.91 (K); 23.90 (L).

Example 2

To the crude product of Example 1 was added 14.92 g (77 mmol) dimethyl terephthalate (obtained from the Sigma Aldrich Company of St. Louis, Mo.) under nitrogen purge. The mixture was heated to 180° C. and then 7.6 μL (300 ppm) Ti(O-nBu)$_4$ (obtained from Acros Organics of Geel, Belgium) added. The reaction mixture was heated to 200° C. for 2 hours, then 220° C. for 5 hours, after which time 1.5 mL of a liquid (theoretical yield of methanol is 3.0 mL) was collected. The collected methanol was removed from the Dean Stark trap and a vacuum of about 5 torr was applied to the reaction flask and maintained for 5 hours. The contents of the reaction flask were then allowed to cool to room temperature and the vacuum was released. Upon cooling, the reaction contents were transparent, brittle, and amber-colored.

Yield: 12.84 g, 22.0%. GPC: M$_n$=1314 PDI=2.31. DSC (−40 to 240° C.): Tg=54.08° C. (ΔH=0.45 J/(g*° C.)).

Example 3

A 250 mL, 3-neck roundbottom flask was charged with 53.82 g (0.247 mol) of EtLGK, 15.97 g (0.082 mol) of dimethyl terephthalate, "DMT" (obtained from the Sigma Aldrich Company of St. Louis, Mo.), and 10.30 g (0.166 mol) ethylene glycol, "EG" (obtained from Fisher Scientific of Waltham, Mass.), for a mole ratio of 3:1:2 EtLGK:DMT:EG, respectively. The flask was equipped with a Dean Stark trap and condenser, mechanical stirrer, nitrogen/vacuum inlet, and nitrogen outlet. The system was degassed and backfilled with N$_2$ a total of five times, applying a vacuum of about 20 torr, and after the five degassing cycles the system was backfilled with nitrogen and a nitrogen sweep was commenced from the inlet through the outlet. Titanium(IV) n-butoxide (16.2 μL, 200 ppm) (obtained from Acros Organics of Geel, Belgium) was injected using a metered micropipette and the mixture was stirred. The flask was immersed in an oil bath heated to 190° C. for approximately 22.5 hours. Liquid was observed to collect in the Dean Stark trap, and once the liquid neared the theoretical yield of ethanol based on observed volume in the trap, a vacuum of approximately 15 torr was applied to the system. The vacuum was maintained for about 2 hours. The flask was then filled with nitrogen and cooled, and a sample taken for GPC analysis.

Then, 9.13 g (0.079 mol) of 1,6-hexamethylene diamine, "HD" (obtained from Acros Organics of Geel, Belgium) was added to the flask. The flask was then degassed/backfilled by alternating vacuum and nitrogen an additional three times, followed by filling the flask with nitrogen and applying a nitrogen sweep through the flask. The flask was immersed in an oil bath set to 180° C. for 1 hour. The temperature of the oil bath was then increased to 200° C. and this was maintained for an additional 1 hour. The temperature of the oil bath was increased again to 210° C. for an additional hour. At this point, vacuum was applied using 2 Teflon pumps (approximately 10 torr) for 3 hours, and then high vacuum applied using an oil pump (500-750 mtorr). The high vacuum was maintained for 1 hour, and then the temperature of the oil bath was increased to 220° C. This temperature and vacuum was then maintained for an additional 48 hours. The flask was placed under nitrogen and cooled to ambient temperature, and the polymer removed from the flask for analysis by GPC and DSC. The results of the analysis are shown in Table 1.

Examples 4-7

Employing the methodology of Example 3, reactions were carried out with varying ratios of reagents EtLGK, DMT, EG, and HD and with varying time under high vacuum. Table 1 shows the reactions and the results of analysis for Examples 4-7.

TABLE 1

Reaction parameters and analytical results obtained for syntheses of Examples 3-7.

| Example No. | Molar ratios | | | | Properties | | | Time Under High Vacuum |
|---|---|---|---|---|---|---|---|---|
| | Et-LGK | DMT | EG | HD | Polyol MW, g/mol | Tg, °C | Observations at end of reaction | |
| 3 | 3 | 1 | 2 | 0.96 | Mn = 1708 Mw = 2670 | 36 | viscous (but not climbing stir rod) | 48.33 hrs. |
| 4 | 1 | 1 | 2 | 0.9 | Mn = 1296 Mw = 2369 | 62 | not very viscous (but still crystalline) | 135 min. |
| 5 | 2 | 1 | 2 | 0.84 | Mn = 1248 Mw = 1969 | 30 | not very viscous | 13 hrs. |
| 6 | 2 | 1 | 2 | 0.9* | Mn = 6664 Mw = 23204 | 49 | very viscous (polymer climbing stir rod) | 21.66 hrs. |
| 7 | 5 | 1 | 2 | 0.87 | Mn = 1494 Mw = 2272 | 25 | viscous (but not climbing stir rod) | 31.25 hrs. |

*In this experiment, the diamine was added as two separate fractions. The first fraction accounted for 0.5 mol equiv., and the second fraction (which was added approximately 22 hrs. later) accounted for 0.4 mol equiv.

Example 8

A flame-dried 250 mL four-necked flask was cooled under a stream of nitrogen and equipped with a mechanical stirrer, Dean-Stark trap, nitrogen inlet, and nitrogen outlet/vacuum port. To the flask was added 7.79 g (67 mmol) 1,6-hexamethylene diamine (obtained from Acros Organics of Geel, Belgium), 24.98 g (67 mmol) of EtBLEK, and 10 mg (0.07 mmol) 1,5,7-triazabicyclo[4.4.0]dec-5-ene (obtained from Acros Organics). With mechanical stirring under a slow nitrogen sweep, the mixture was heated to 50° C. for 16 hours, then 200° C. for 4 hours, during which a liquid was observed to collect in the Dean-Stark trap. At the end of the 20 hours reaction time, liquid collection subsided. Heating for an additional 16 hours at 200° C. resulted in increased solution viscosity. Subsequent application of vacuum (8 torr) at 220° C. for 2 hours was accompanied by bubbling of the reaction mixture and further increase in solution viscosity.

The contents of the reaction flask were cooled to ambient temperature, yielding a transparent, brittle, amber-colored material. Yield was 19.63 g, or 59.8 wgt %. GPC analysis revealed $M_n$=2153, PDI=1.33. DSC was carried out using temperature profile 3; Tg=56.91° C. ($\Delta$H=0.37 J/(g*° C.)).

Example 9

A 250 ml 3 neck round bottom flask was charged with 50.4 g (0.135 mol) of EtBLEK, 17.0 g (0.27 mol) of ethylene glycol (obtained from the Fisher Scientific Company of Waltham, Mass.) and 13.5 μl (200 ppm) of titanium tetrabutoxide (Ti(O-nBu)$_4$, obtained from Acros Organics of Geel, Belgium). The flask was equipped with a mechanical stirrer, a Dean Stark trap and condenser, and a nitrogen inlet and nitrogen/vacuum outlet. The contents of the flask were degassed at room temperature by subjecting to 5 vacuum/nitrogen purge cycles. After the degassing cycles were completed the flask was backfilled with nitrogen and a slow nitrogen sweep was commenced. The flask was placed in an oil bath set to a temperature of 190° C. The flask was stirred in the oil bath for about 13 hours. At this point a vacuum was applied to the contents until the pressure was between 2 and 3.5 torr. This was maintained for about half an hour, after which time the temperature in the oil bath was increased to 210° C. The temperature and vacuum were maintained for about 1.5 hours.

The contents of the flask were then cooled to about 65° C., at which point a sample was removed for analysis. GPC showed that the number average molecular weight ($M_n$) was 3,600 g/mol and weight average molecular weight ($M_w$) was about 7,400 g/mol, for a polydispersity index of about 2.8.

The reaction flask was then additionally charged with 13.5 g (0.116 mol) of 1,6-hexamethylenediamine (obtained from Acros Organics of Geel, Belgium) and the flask was degassed with a 3 vacuum/nitrogen purge cycles. At the end of the degassing cycles, the flask was backfilled with nitrogen, and a slow nitrogen sweep was initiated with stirring. The flask was placed in an oil bath having a temperature preset to 180° C. This temperature was maintained for 1 hour and then the temperature of the oil bath was increased to 200° C. This temperature was maintained for another hour and then the temperature was increased to 210° C. This temperature was maintained for about 1.5 hours, then a vacuum was applied to the flask until the pressure in the flask reached between about 3 and 5 torr. Over the ensuing 3 hours, the vacuum in the flask was observed to decrease to about 0.5 torr (500 millitorr). The contents of the reaction flask were observed to undergo significant increase in viscosity during this time. The reaction was stopped when the contents of the reaction flask could no longer be stirred due to the contents climbing the stir rod.

Upon cooling the contents of the flask to ambient temperature, a transparent, orange solid was obtained. The solid was insoluble and could not be broken by hand. Glass transition temperature was measured by DSC to be about 60° C.

Tensile testing was carried out according to ASTM D638-90, specimen type IV. The specimens for testing were prepared by removing material from the flask and placing it between TEFLON® coated aluminum foil sheets (BYTAC®, obtained from Fisher Scientific of Waltham, Mass.) and pressing with a spacer of 1.5 mm using a Carver Model 4122 pneumatic heated platen press (obtained from Carver, Inc. of Wabash, Ind.) preheated to 180° C., at a pressure of about 2268 kg, for about 10 minutes. The pressed sample was removed from the press and cut into pieces. The pieces were placed on top of TEFLON® molds machined to specifications of ASTM D638-90, specimen IV, 1 mm deep. A BYTAC® sheet was placed on top of the samples and mold. The BYTAC® sheet, samples, and mold were pressed at 180° C. at 2268 kg for about 10 minutes. The samples were cooled to room temperature and placed in a vacuum oven at 50° C. for about 16 hours; the samples were removed from the oven immediately prior to tensile testing.

Figure 2:
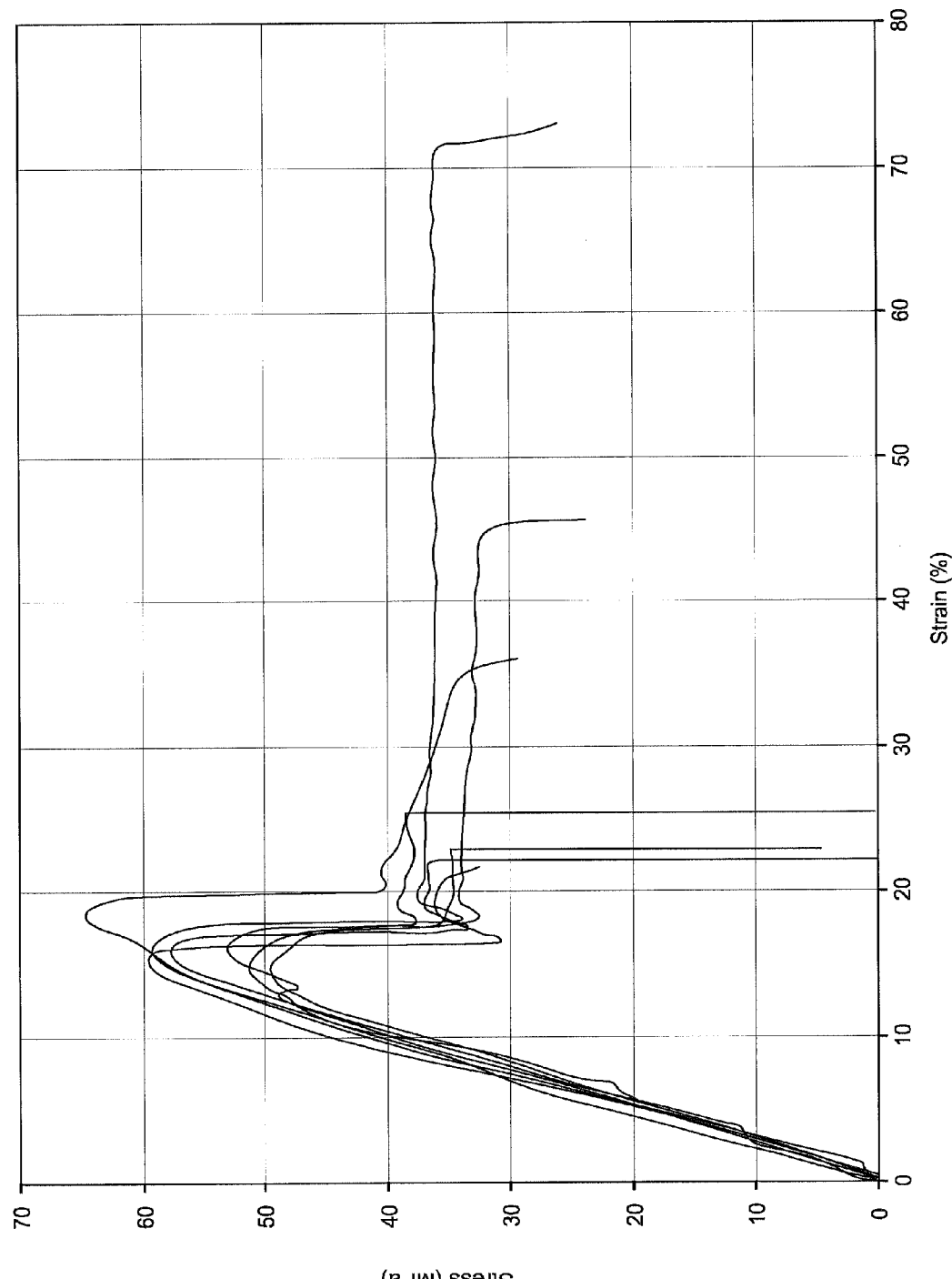
FIG. 2 is a plot of the stress-strain measurements for a compound of the invention.

Testing was performed with nominal strain at outset of about 0.17. The result of tensile tests carried out on seven samples prepared as described above are shown in Table 2. The stress-strain curve for each of the seven samples is shown in FIG. 2. It can be observed in FIG. 2 that the samples are ductile, having a yield stress at about 15-20% strain, but ultimate strain between about 22-72%.

Examples 10-12

The procedure of Example 9 was repeated, except that the mole percent (mol %) of 1,6-hexamethylenediamine ("HD") to EtBLEK was varied. Glass transition temperature was measured by DSC; tensile data were measured using the technique of Example 9. The mol % HD and thermal and tensile data are reported in Table 2.

TABLE 2

HD content and resulting properties for polymers of Examples 9-12.

| Example No. | HD, mol % based on EtBLEK | $T_g$, ° C. | Tensile Properties | | |
|---|---|---|---|---|---|
| | | | Yield stress, MPa | Tensile strength, MPa | Strain at break, % |
| 9 | 86% | 60 | 57 | 36 | 34 |
| 10 | 95% | 65 | — | — | — |
| 11 | 98% | 66 | 67 | 45 | 29 |
| 12 | 100% | 66 | 69 | 45 | 22 |

Example 13

A 250 mL, three-neck roundbottom flask was charged with 31.5 g (81.2 mmol) EtBLPK and 10.1 g (163 mmol) ethylene glycol (obtained from Fisher Scientific of Waltham, Mass.), and 8.3 mL (200 ppm) Ti(O-nBu)$_4$ (obtained from Acros Organics of Geel, Belgium). The flask was equipped with a mechanical stirrer, Dean Stark trap, nitrogen/vacuum inlet, and nitrogen outlet. The flask was degassed with three cycles of evacuating the flask to approximately 5 torr followed by backfilling with nitrogen. After the three cycles, the flask was backfilled with nitrogen and a nitrogen sweep through the flask was commenced. The mixture was stirred in an oil bath set to about 190-210° C. under nitrogen sweep for about 18.5 hours, and then under a vacuum of about 4-13 torr for about 4 hours, then under a vacuum of 0.4 torr for about 2.5 hrs.

The flask was then cooled to room temperature and 8.5 g (73.3 mmol) 1,6-hexamethylenediamine (obtained from Acros Organics of Geel, Belgium) was added to the flask contents. The flask was placed in an oil bath at a temperature of between about 180-210° C. under nitrogen sweep for about 5 hours, then a vacuum of about 26 torr was applied for about 3.5 hours. The contents of the flask were cooled to room temperature and a sample was removed for analysis by DSC. The contents of the flask were found to have a Tg of about 7° C.

Example 14

A 250 mL three-neck roundbottom flask was equipped with a mechanical stirrer, Dean Stark trap, nitrogen/vacuum inlet, and nitrogen outlet. The flask was charged 39.4 g (124 mmol) EtBPEK and 14.5 g (125 mmol) 1,6-hexamethylene-diamine (obtained from Acros Organics of Geel, Belgium). The flask was degassed with three cycles of evacuating the flask to approximately 20 torr followed by backfilling with nitrogen. After the three cycles, the flask was backfilled with nitrogen and a nitrogen sweep through the flask was commenced. The mixture was stirred in an oil bath set to a temperature of about 190-200° C. for 20 hours, then the temperature of the oil bath was increased to about 200-210° C. and a vacuum of 10-35 torr was applied to the flask for about 7 hours The contents of the flask were cooled to room temperature and a sample was removed for analysis by DSC. The contents of the flask were found to have a Tg of about 45° C.

Example 15

A 250 mL, three neck roundbottom flask was charged with 7.6 g (0.0392 mol) dimethyl terephthalate (obtained from the Sigma-Aldrich Company of St. Louis, Mo.), 7.6 g (0.0392 mol) dimethyl isophthalate (obtained from the Sigma-Aldrich Company), 27.3 g (0.073 mol) EtBLEK, and 18.0 g (0.155 mol) of 1,6-hexamethylene diamine (obtained from Acros Organics of Geel, Belgium). The flask was equipped with a Dean Stark trap, mechanical stirrer, nitrogen/vacuum inlet, and nitrogen outlet. The flask was degassed 5 times by applying a vacuum of about 5.0 torr and then releasing the vacuum with a nitrogen flow. After the five degassing cycles vacuum was released by applying a nitrogen sweep through the flask. The flask was placed in an oil bath set to a temperature of 180° C. with stirring for about 30 minutes. The temperature in the oil bath was then increased to 210° C. and this temperature was maintained for about 2 hours with stirring. After that the vacuum was applied to the flask. Over a period of about 2 hours the vacuum in the flask was observed to go from about 18.0 torr to about 1.0 torr. The temperature and stirring were maintained with vacuum for the next 11 hours during which time the vacuum was observed to fall to 0.5 torr. At the end of the 11 hours the contents of the reaction flask were observed to have sufficiently high viscosity that stirring could not be maintained and the contents of the flask were allowed to cool to room temperature.

Figure 3:
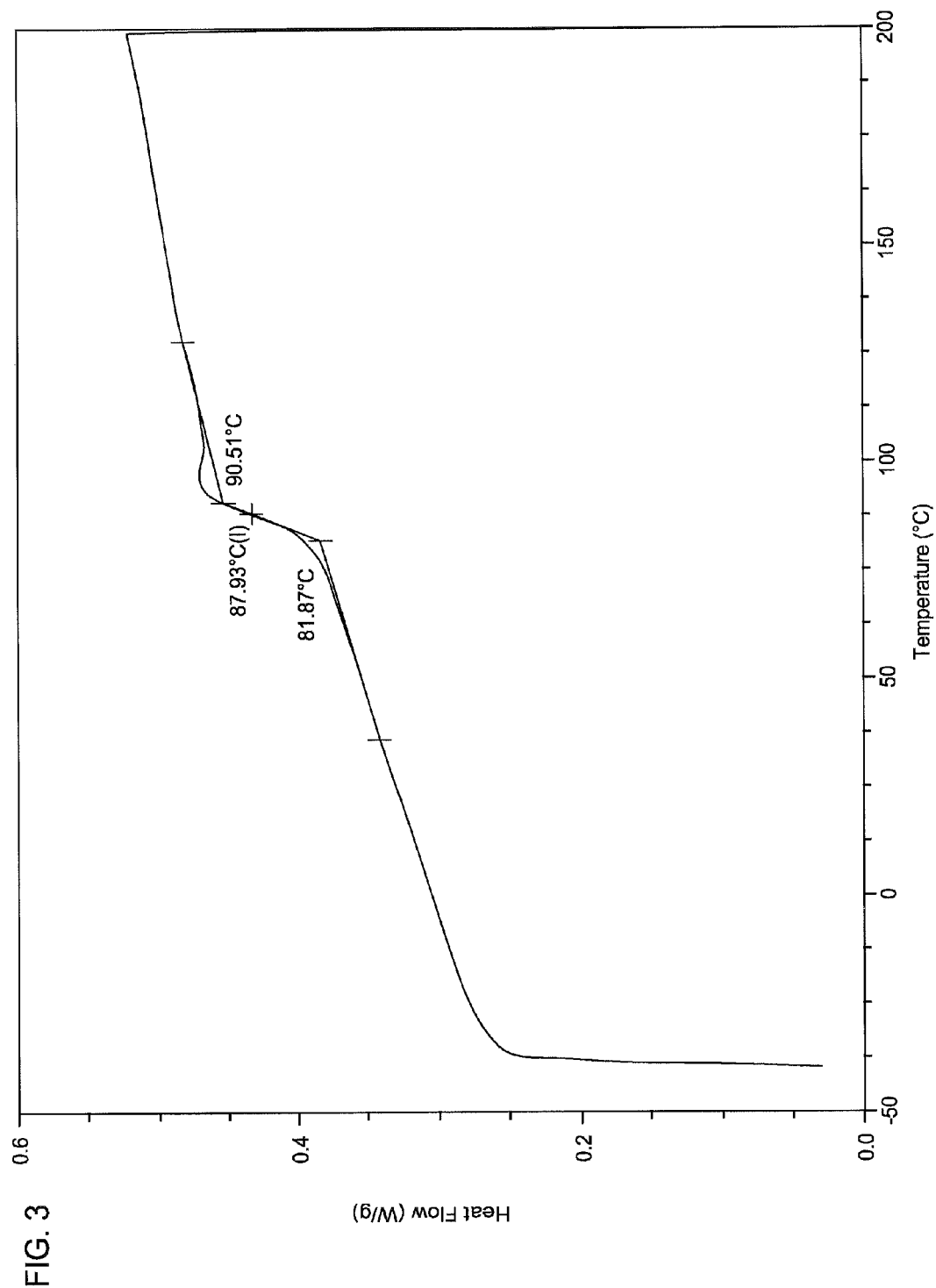
FIG. 3 is a plot of the differential scanning calorimetry measurements for a compound of the invention.

A portion of the contents of the flask were removed for DSC analysis, which revealed that the glass transition temperature ($T_g$) was about 88° C. No crystalline transition was observed in the DSC trace. The DSC trace is shown in FIG. 3.

Example 16

Figure 4:
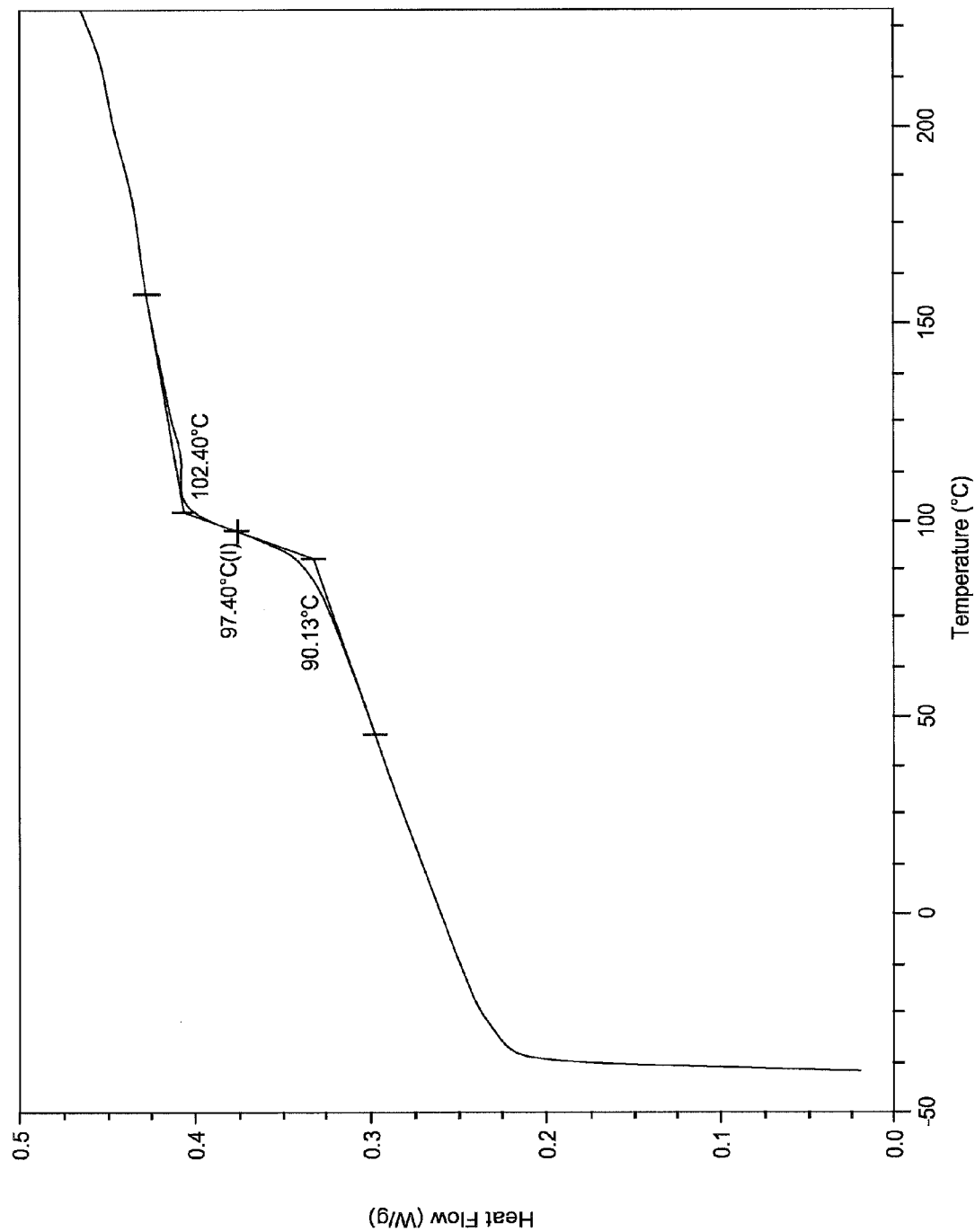
FIG. 4 is a plot of the differential scanning calorimetry measurements for a compound of the invention.

The procedure of Example 15 was repeated except that 27.88 g (0.0745 mol) of EtBLEK, 18.38 g (0.158 mol) 1,6- hexamethylene diamine, 16.4 g (0.0845 mol) of dimethyl terephthalate, and no dimethyl isophthalate was used. The contents of the reaction flask at the end of the procedure were determined by DSC to have a glass transition temperature of 97° C. and no crystalline transition. The DSC trace is shown in FIG. 4.

Example 17

A 3 neck 250 ml flask was charged with 50.50 g (0.135 mol) EtBLEK and 12.0 g (0.103 mol) of 1,6-hexamethylene diamine (obtained from Acros Organics of Geel, Belgium). The flask was equipped with a Dean Stark trap, mechanical stirrer, and nitrogen/vacuum inlet and outlet. The flask was subjected to 5 degassing cycles by alternating between a vacuum of about 10 torr and nitrogen sweep. At the end of the 5 cycles the flask was placed under a nitrogen sweep, and with stirring was placed in an oil bath set to 180° C. The temperature of the oil bath was then ramped at about 2° C./hour until the final temperature of 200° C. was reached. The temperature of 200° C. was then maintained for the next 4 hours. A vacuum was then applied to the flask and the vacuum in the flask was observed to go from 10.7 torr to about 2.8 torr over the period of about 1 hour. The oil bath was then shut off and allowed to slowly cool to 100° C.

After the oil bath had cooled to about 100° C. the vacuum to the flask was released by backfilling with nitrogen, and the flask was quickly opened under nitrogen and charged with 47.4 g (0.244 mol) of dimethyl terephthalate (obtained from the Sigma-Aldrich Company of St. Louis, Mo.), 32.1 g (0.35 mol) of 1,4-butane diol (obtained from the Sigma Aldrich Company), and 16.1 μl (200 ppm) of Ti(O-nBu)$_4$ (obtained from Acros Organics). The flask was then closed and degassed with 5 cycles of a vacuum of about 10 torr alternated with a nitrogen sweep. After the degassing cycles the flask was placed under nitrogen sweep and the temperature of the oil bath was ramped up to 180° C. with stirring. This temperature was maintained for about 2 hours and then the temperature in the flask was increased to 200° C. and this temperature was maintained for about 2 hours. Then with the temperature still at 200° C. a vacuum was applied to the flask and the vacuum inside the flask was observed to go from 34.4 torr to 7.7 torr over a period of 2.5 hours. The temperature of the oil bath was then increased to 210° C. while still under vacuum and the temperature was then maintained for another ½ hour and then the temperature of the oil bath was increased to 220° C. for the next hour. The contents of the reaction flask were then observed to be at sufficiently high viscosity that stirring could not be continued and stirring was stopped and the flask was allowed to cool to room temperature.

The contents of the reaction flask were subjected to DSC, which showed the reaction product had a glass transition temperature ($T_g$) of 39° C. and a melt temperature ($T_m$) of 130° C.

Example 18

A flame-dried 250 mL three-neck flask was charged with 41.82 g (100 mmol) EtBLDK and 11.84 g (102 mmol) 1,6-hexamethylene diamine (obtained from Acros Organics of Geel, Belgium). The flask was equipped with a mechanical stirrer, nitrogen inlet, nitrogen outlet, and Dean Stark trap. Nitrogen sweep was applied through the flask. The flask was immersed in an oil bath set to 180° C., and the temperature was gradually raised to 200° C. at the rate of about 2° C./min. Heating was continued at 200° C. for an additional 14 hours, resulting in collection of 15.5 mL of liquid in the Dean-Stark trap. After the liquid in the Dean-Stark trap was drained, a vacuum of 10-20 torr was applied to the flask for 1 hour. The vacuum level was then decreased to about 6 torr while the temperature of the oil bath was raised to 210° C. Heating was continued for 6 hours, and the vacuum level was gradually decreased from 6 Torr to 0.2 Torr. The crude polymer was isolated after slight cooling. The crude polymer was isolated as a red brittle solid and analyzed by DSC and GPC. Yield: 33.19 g. DSC (−80 to 200° C., 10° C./min, $T_g$=34.9° C.). GPC: Mn=10700, PDI=10.1.

Example 19

A flame-dried, 250 mL four-neck roundbottom flask was charged with 38.31 g (111 mmol) EtBAEK and 14.02 g (226 mmol) ethylene glycol (obtained from Fisher Scientific of Waltham, Mass.). The flask was equipped with a mechanical stirrer, Dean-Stark trap, and nitrogen/vacuum inlet. The flask was degassed at room temperature with three repetitions of evacuating the flask to about 1.5 torr and back-filling with nitrogen. After degassing, the flask was back-filled with nitrogen and 10.5 μL (200 ppm) Ti(OBu)$_4$ (obtained from Acros Organics of Geel, Belgium) was added to the reaction mixture. The flask was placed in an oil bath with a temperature set to 190° C. and was stirred under nitrogen for 14 hours. The temperature of the oil bath was then increased to 200° C. and was maintained at that temperature for 2.5 hours, then the temperature of the oil bath was increased to 210° C. and was maintained at the temperature for 30 minutes. During this time about 4.0 g of a liquid was observed to collect in the Dean Stark trap. The liquid was drained, and a vacuum was applied to the flask. The vacuum level started at about 20 torr, and was gradually lowered to 5 torr over the next 3 hours while the oil bath temperature was maintained at 210° C. After 3 hours, the flask was back-filled with nitrogen and was allowed to cool to room temperature.

At this point, 11.68 g (101 mmol) 1,6-hexamethylene diamine (obtained from Acros Organics of Geel, Belgium) was added to the flask. The flask was placed in an oil bath set to a temperature of 180° C. with stirring under nitrogen, and held at this temperature for 1 hour; then the temperature of the oil bath was increased to 200° C. and held at this temperature for 30 minutes; then the temperature of the oil bath was increased to 220° C. and held at this temperature for 1 hour. At this point a vacuum of about 4-10 torr was applied to the flask while the temperature of the oil bath was maintained at 220° C. for 15 hours. Then the flask was back-filled with nitrogen and allowed to cool slightly before the crude reaction product was isolated.

The crude reaction product was isolated as a black brittle solid and was analyzed by DSC and GPC. Yield: 12.29 g. DSC: $T_g$=36.9° C.). GPC: Mn=5500, PDI=2.62.

Example 20

A 500 mL four-neck roundbottom flask was flame-dried and charged with 99.25 g (265 mmol) EtBLEK, 33.38 g (538 mmol) ethylene glycol (obtained from Fisher Scientific of Waltham, Mass.), and 27 μL (200 ppm) Ti(O-nBu)$_4$ (obtained from Acros Organics of Geel, Belgium). The flask was equipped with a mechanical stirrer, Dean Stark apparatus, and nitrogen/vacuum inlet. The system was degassed while stirring in an oil bath set to 40° C. with three repetitions of evacuating the flask to approximately 1 torr and back-filling with nitrogen. After degassing, the flask was backfilled with nitrogen. The temperature of the oil bath was increased to 190° C. and the contents of the flask were stirred for 22 hours, resulting in collection of 22 mL of liquid in the Dean Stark trap. At this point a vacuum of about 10 torr was applied to the flask for 1 hour, then the temperature of the oil bath was increased to 210° C. and this temperature was maintained for 1.5 hours, resulting in 13 mL of liquid collected in the Dean Stark trap. The flask was back-filled with nitrogen, and the contents of the flask were allowed to cool before collecting the crude reaction product. The reaction crude product was analyzed by GPC to determine $M_n$=1117, PDI=2.0.

A 250 mL three-neck round bottom flask was charged with the 31.58 g of the crude reaction product. The flask was equipped with a mechanical stirrer, Dean Stark apparatus, and nitrogen/vacuum inlet. An addition funnel was installed and charged with 10.6 g (102 mmol) bis(2-aminoethyl)amine (obtained from Acros Organics of Geel, Belgium). The flask was warmed to about 40° C. using an oil bath before degassing with three repetitions of evacuating the flask to approximately 1 torr and back-filling with nitrogen. After degassing, a nitrogen sweep was applied through the flask. The temperature of the oil bath was then increased to 190° C. and the contents of the flask were stirred under nitrogen sweep while bis(2-aminoethyl)amine was added dropwise over about 1 hour. After the addition was complete, stirring was continued for 1 additional hour at 190° C. under nitrogen, at which point a vacuum was applied to the flask. The reaction mixture was then stirred at 190° C. under 0.5 torr vacuum for 40 minutes, resulting in collection of 5.5 mL of liquid in the Dean Stark trap. The temperature was increased to 210° C. and 0.5 torr applied for 1 additional hour. At this point the flask was back-filled with nitrogen and allowed to cool slightly before the crude product was isolated as a brittle red solid and analyzed by DSC and GPC. Yield: 23.28 g. DSC revealed $T_g$=72.68° C. ($\Delta H$=0.42 J/(g*° C.)). GPC (DMF mobile phase: $M_n$=5293, PDI=1.93.

Example 21

A 250 mL four-neck roundbottom flask was charged with 12.63 g (32.5 mmol) EtBLPK, 13.72 g (32.8 mmol) EtBLDK, and 7.31 g (62.9 mmol) 1,6-hexamethylene diamine (obtained from Acros Organics of Geel, Belgium). The flask was equipped with a mechanical stirrer, Dean Stark trap, and nitrogen/vacuum inlet. The flask was degassed at ambient temperature with three repetitions of evacuating the flask to approximately 1 torr and back-filling with nitrogen. The flask was placed in an oil bath with temperature set to 150° C. and was stirred under nitrogen for 2 hours, resulting in collection of 6 mL of liquid in the Dean Stark trap. The temperature of the oil bath was increased to 190° C. and this temperature was maintained for 1 hour; then the temperature of the oil bath was increased to 200° C. and this temperature was maintained for 16 hours, resulting in collection of 1.2 mL of liquid in the Dean Stark trap.

The contents of the flask were allowed to cool slightly before the crude product was collected. The crude product was isolated as a hard orange solid that was insoluble in THF and DMF and was analyzed by DSC to determine that $T_g$=37.14° C. ($\Delta H$=0.40 J/(g*° C.)).

Example 22

A flame-dried 250 mL four-neck roundbottom flask was flame dried, then cooled to ambient temperature under nitrogen. The flask was charged with 40.2 mg (0.29 mmol) 1,3,4,6,7,8-hexahydro-2H-pyrimido[1,2-a]-pyrimidine (TBD, obtained from the Sigma-Aldrich Company of St. Louis, Mo.), 12.78 g (110 mmol) 1,6-hexamethylene diamine (obtained from the Fluka Chemical Corporation of Milwaukee, Wis.) and 41.16 g (110 mmol) EtBLEK. The flask was equipped with a mechanical stirrer, Dean Stark trap, and nitrogen/vacuum inlet. The contents of the flask were degassed with three repetitions of evacuating the flask to approximately 1 torr and back-filling with nitrogen. After degassing, the flask was back-filled with nitrogen. The flask was placed in an oil bath set to a temperature of 120° C. and was stirred for 29 hours, resulting in the collection of 3 mL of liquid in the Dean Stark trap. A sample of the contents of the flask was removed for analysis by GPC: $M_n$=4903, PDI=1.69.

Then the flask was placed in an oil bath set to a temperature of 140° C. for 16 hours under nitrogen, leading to collection of an additional 1 mL of liquid in the Dean Stark trap. A sample of the contents of the flask was removed for analysis by GPC: $M_n$=6627, PDI=1.83.

Finally, the flask was placed in an oil bath set to a temperature of 180° C. for 4 hours, then 200° C. for 0.5 hours, under nitrogen. When the oil bath reached 200° C. a vacuum of 0.5 torr was applied to the flask for about 1 hour, resulting in a viscous amber mixture. The vacuum was released by back-filling with nitrogen and the contents of the flask were isolated after slight cooling. Yield: 26.25 g.

Example 23

A 500 mL four-neck flask was flame dried and cooled under nitrogen. The flask was charged with 99.25 g (265 mmol) EtBLEK, 33.38 g (538 mmol) ethylene glycol (obtained from Fisher Scientific of Waltham, Mass.), and 27 µL (200 ppm) Ti(O-nBu)$_4$ (obtained from Acros Organics of Geel, Belgium). The flask was equipped with a mechanical stirrer, Dean Stark trap, and nitrogen/vacuum inlet. The flask was placed in an oil bath set to 40° C. and was degassed with three repetitions of evacuating the flask to approximately 1 torr and back-filling with nitrogen. After degassing, the flask was back-filled with nitrogen. The temperature of the oil bath was increased to 190° C. and the flask was stirred under nitrogen for 22 hours, resulting in collection of 22 mL of liquid in the Dean Stark trap. Then a 10 torr vacuum was applied to the flask while maintaining the oil bath temperature at 190° C. for 1 hour. The temperature of the oil bath was then increased to 210° C. and this temperature was maintained for 1.5 hours, resulting in an additional 13 mL of liquid collected in the Dean Stark trap.

The crude product was analyzed by GPC: $M_n$=1117, PDI=2.0.

A 250 mL four-neck roundbottom flask was flame-dried and cooled under nitrogen. The flask was charged with 30.63 g of the crude reaction product of EtBLEK and ethylene glycol, 8.34 g (72 mmol) 1,6-hexamethylene diamine (obtained from Acros Organics of Geel, Belgium), and 24.82 g (143 mmol) dimethyl adipate (obtained from the Sigma-Aldrich Company of St. Louis, Mo.). The flask was equipped with a mechanical stirrer, Dean Stark trap, and nitrogen/vacuum inlet. The flask was placed in an oil bath at a temperature of about 40° C. and was degassed with three repetitions of evacuating the flask to approximately 1 torr and back-filling with nitrogen. The oil bath temperature was then increased to about 220° C. and the contents of the flask were stirred under nitrogen for 1.5 hours, resulting in collection of 2 mL of liquid in the Dean Stark trap. At this point a vacuum of 3 torr was applied to the flask for 45 minutes, resulting in collection of an additional 10 mL of liquid. Then the temperature of the oil bath was decreased to about 210° C. and a vacuum of 0.5 torr was applied to the flask for 22 hours, resulting in collection of 1.3 mL of liquid in the Dean Stark trap. The flask was back-filled with nitrogen and cooled to room temperature.

The flask was then additionally charged with 7.01 g (113 mmol) ethylene glycol (obtained from Fisher Scientific of Waltham, Mass.) and the contents of the flask were stirred in the reactor at 100° C. under nitrogen over 16 hours. An additional 14 μL (200 ppm) Ti(O-nBu)$_4$ was added and the flask, and the temperature of the oil bath was then increased to about 210° C. The contents of the flask were stirred under nitrogen for 17 hours, resulting in collection of 1.3 mL of liquid in the Dean Stark trap. A vacuum of 0.5 torr was then applied to the flask for 16 hours, resulting in an additional 4.7 mL of liquid collected and substantial buildup in viscosity of the reaction mixture. The flask was then back-filled with nitrogen and removed from the oil bath, and allowed to cool slightly before the crude product was isolated. The crude product was a brown, rubbery solid and was analyzed by DSC and GPC. Yield: 34.56 g. DSC: $T_g$=9.78° C., ΔH=0.42 J/(g*° C.)). GPC: $M_n$=13700, PDI=4.95.

Example 24

A 250 mL four-neck round bottom flask was charged with 26.06 g (69.6 mmol) EtBLEK and 8.40 g (72.3 mmol) 1,6-hexamethylene diamine (obtained from Acros Organics of Geel, Belgium). The flask was equipped with a mechanical stirrer, Dean Stark apparatus, and nitrogen/vacuum inlet. The contents of the flask were placed in an oil bath set to a temperature of 50° C. and stirred under nitrogen purge for 16 hours. The contents of the flask were then degassed with three repetitions of evacuating the flask to approximately 1 torr and back-filling with nitrogen. After degassing, the flask was back-filled with nitrogen. The flask was additionally charged with 6.9 μL (200 ppm) Ti(O-nBu)$_4$ (obtained from Acros Organics of Geel, Belgium). The temperature of the oil bath was increased to 190° C. and the contents of the flask were stirred for 21 hours under nitrogen. The temperature of the oil bath was then increased to 210° C. and a vacuum of about 0.5 torr was applied to the flask for 7 hours. The flask was then back-filled with nitrogen and the contents of the flask allowed to cool slightly before a sample of the crude reaction product was removed for analysis by DSC: $T_g$=55.11° C., ΔH=0.37 J/(g*° C.)).

Dimethyl adipate (obtained from the Sigma-Aldrich Company of St. Louis, Mo.) was dried by placing an aliquot of the compound in a flask, which was placed in an oil bath set to a temperature of 60° C. under nitrogen sweep for 16 hours. The flask containing the crude reaction product of EtBLEK and 1,6-hexamethylene diamine was then additionally charged with 12.16 g (70 mmol) of the dried dimethyl adipate. The flask was placed in an oil bath set to a temperature of 90° C. and degassed with three repetitions of evacuating the flask to approximately 1 torr and back-filling with nitrogen. The temperature of the oil bath was then increased to about 210° C. and he contents of the flask were stirred under nitrogen for 1 hour, after which time the reactor was equipped with an addition funnel charged with 7.23 g (62.2 mmol) 1,6-hexamethylene diamine. The contents of the addition funnel were melted with a heat gun and then added dropwise over about 7 hours to the reaction mixture stirred at 210° C. under nitrogen. A marked increase in solution viscosity was observed, accompanied by 4.0 mL of liquid collecting in the Dean Stark trap. The temperature of the oil bath was then increased to 220° C. and a vacuum of 0.5 torr was applied to flask for 3.5 hours. The temperature of the oil bath was then increased to 240° C. under 0.5 torr vacuum for 3.0 hours. The flask was back-filled with nitrogen and allowed to cool slightly before the contents of the flask were isolated. Upon cooling to room temperature, the isolate was an amber opaque solid that was completely insoluble in THF and DMF. The isolate was analyzed by DSC: $T_g$=45.08° C. ΔH=0.39 J/(g*° C.), $T_m$=170.9° C.

Example 25

A 250 mL three-neck roundbottom flask was charged with 25.35 g (67.7 mmol) EtBLEK and 7.83 g (67.4 mmol) 1,6-hexamethylene diamine (obtained from Acros Organics of Geel, Belgium). The flask was equipped with a mechanical stirrer, Dean Stark trap, and nitrogen/vacuum inlet. The contents of the flask were degassed in an oil bath set to a temperature of 30° C. by three repetitions of evacuating the flask to approximately 1 torr and back-filling with nitrogen. After degassing, the flask was back-filled with nitrogen. The temperature of the oil bath was increased to 190° C. and the contents of the flask were stirred under nitrogen for 16 hours. The temperature of the oil bath was then increased to 210° C. for 2 hours, resulting in 3 mL of liquid collected in the Dean Stark trap and an observed increase in solution viscosity. A sample of the contents of the flask were removed for analysis by DSC: $T_g$=50.76° C., ΔH=0.39 J/(g*° C.) and GPC: $M_n$=10967, PDI=1.81.

Dimethyl adipate (obtained from the Sigma-Aldrich Company of St. Louis, Mo.) was dried by placing an aliquot of the compound in a flask, which was placed in an oil bath set to a temperature of 60° C. under nitrogen sweep for 16 hours. The flask containing the crude reaction product of EtBLEK and 1,6-hexamethylene diamine was then additionally charged with 11.94 g (68.5 mmol) of the dried dimethyl adipate and 8.55 g (127.7 mmol) ethylene glycol (obtained from Fisher Scientific of Waltham, Mass.). The flask was placed in an oil bath set to a temperature of 60° C. for 16 hours while a nitrogen sweep was applied across the flask. Then 16 μL (300 ppm) Ti(O-nBu)$_4$ (obtained from Acros Organics of Geel, Belgium) was added. The contents of the flask were degassed with three repetitions of evacuating the flask to approximately 1 torr and back-filling with nitrogen. Once degassed, the reaction mixture back-filled with nitrogen and stirred for 24 hours at in an oil bath set to a temperature of 190° C. Then a vacuum of 0.3 torr was applied to the flask for 1.5 hours. The temperature of the oil bath was increased to 210° C. for 2 hours under a vacuum of 0.4 torr. The flask was back-filled with nitrogen and allowed to cool slightly before the contents were isolated. The isolate was analyzed with DSC: $T_g$=18.74° C., ΔH=0.38 J/(g*° C.) and GPC: =14441, PDI=2.47.

Example 26

Figure 5:
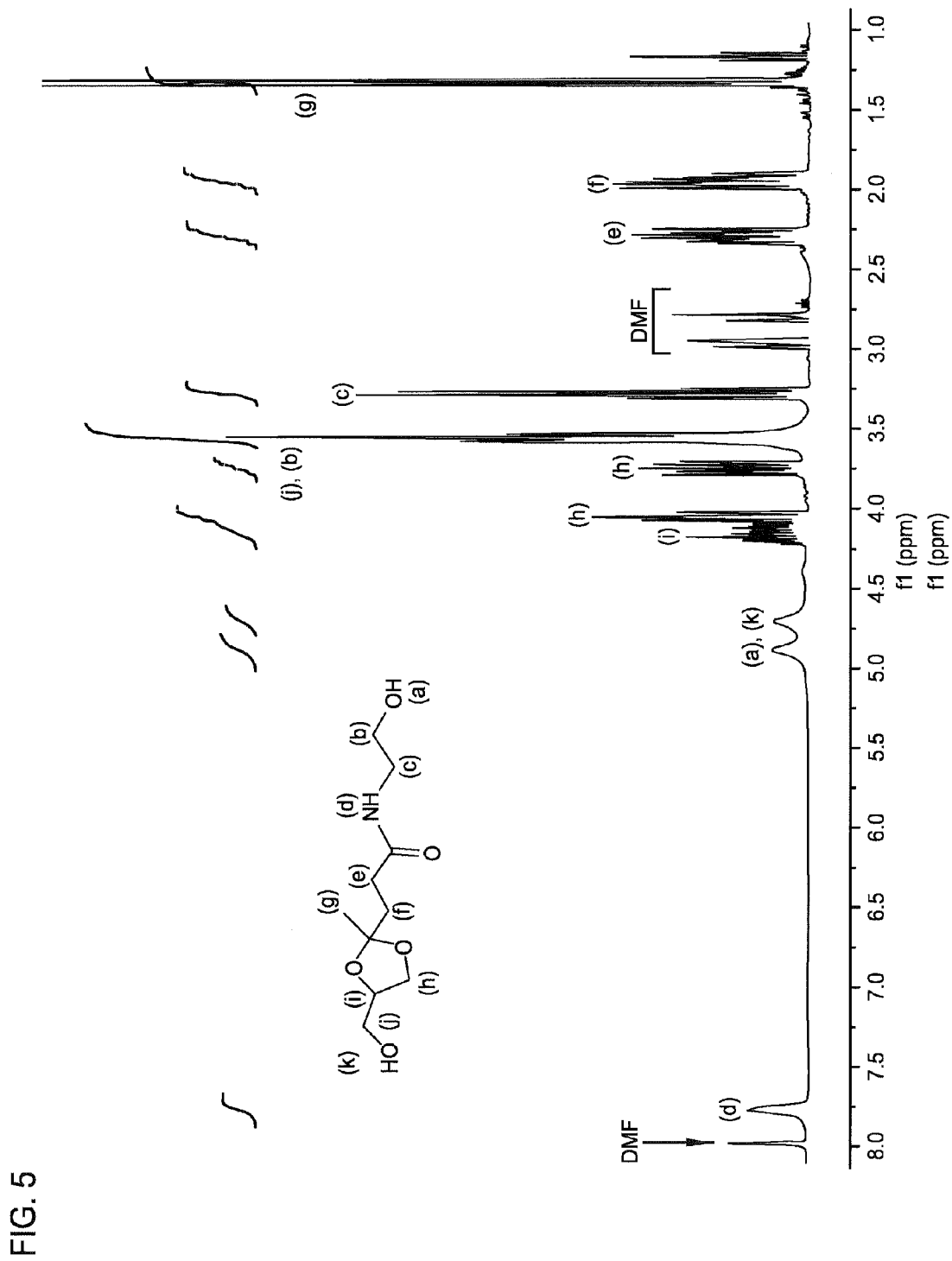
FIG. 5 is a plot of the $^1$H NMR measurements for a compound of the invention.

A 250 mL 3-neck roundbottom flask was charged with 38.07 g (0.174 mol) EtLGK and 10.70 g (0.175 mol) 2-aminoethanol (obtained from TCI America of Portland, Oreg.). The flask was equipped with a mechanical stirrer, a Dean-Stark trap, and a nitrogen inlet/outlet. The flask was degassed by three repetitions of applying vacuum of about 40 torr to the flask, followed by back-filling with nitrogen at room temperature. After degassing was complete, the flask was back-filled with nitrogen and 16.7 μL (200 ppm) Ti(O-nBu)$_4$ (obtained from Acros Organics of Geel, Belgium) was added to the flask. The flask was degassed an additional three times and back-filled with nitrogen. Then the flask was placed in an oil bath at room temperature and the oil bath was then heated to 150° C., and the flask was stirred under nitrogen for about 20.5 hours. The flask was removed from the oil bath and cooled to about 100° C. A sample of the contents of the flask was removed for analysis by $^1$H NMR (300 MHz, DMF-d$_7$ solvent); the carboxamide structure was confirmed. The $^1$H NMR is shown in FIG. 5.

Dimethyl terephthalate (obtained from the Sigma-Aldrich Company of St. Louis, Mo.) was ground into a powder and 33.68 g (173 mmol) of the powder was added to the flask. The flask was placed under nitrogen in the warm oil bath and the bath temperature was set to 210° C. This temperature was maintained for about 6.5 hours with stirring, and then a vacuum of approximately 100 torr was applied to the flask. After 1 hour, the pressure was decreased to approximately 1 torr. After three more hours the flask was back-filled with nitrogen and removed from the oil bath.

The contents of the flask were analyzed by DSC and GPC. GPC: $M_n$=8131, $M_w$=19129, PDI=2.35. DSC: $T_g$=64° C.

Example 27

A 250 mL 3-neck roundbottom flask was charged with 25.61 g (132 mmol) dimethyl terephthalate (obtained from the Sigma-Aldrich Company of St. Louis, Mo.) and 8.36 g (137 mmol) 2-aminoethanol (obtained from TCI America of Portland, Oreg.). The flask was equipped with a mechanical stirrer, Dean-Stark trap, and a nitrogen inlet/outlet. The flask was degassed by applying three vacuum/nitrogen cycles employing a vacuum of about 15 torr followed by back-filling with nitrogen. After degassing, the flask was back-filled with nitrogen, then 12.7 µL (200 ppm) Ti(O-nBu)$_4$ (obtained from Acros Organics of Geel, Belgium) was added to the flask via microliter pipette. The flask was degassed/backfilled an additional 3 times, followed by back-filling with nitrogen. The flask was placed in an oil bath and the temperature of the oil bath was set to 150° C. and left for 1 hour. Then the flask was cooled to 120° C., and 28.82 g (132 mmol) EtLGK was added to the flask. The oil bath temperature was increased to 210° C. and maintained for 7 hours. The pressure in the flask was then decreased to 20 torr over the ensuing 90 minutes and these conditions maintained for another 4 hours. The pressure was then further decreased to between 750 millitorr and 1000 millitorr and maintained for 8.5 hours. The flask was then backfilled with nitrogen and removed from the oil bath. The resulting polymer was analyzed by DSC and found to have a $T_g$ of 51° C.

Example 28

A 250 mL 3-neck roundbottom flask was charged with 43.27 g (116 mmol) EtBLEK and 7.06 g (116 mmol) 2-aminoethanol (obtained from TCI America of Portland, Oreg.). The flask was equipped with The flask was equipped with a mechanical stirrer, Dean-Stark trap, and a nitrogen inlet/outlet. The flask was degassed by applying three vacuum/nitrogen cycles employing a vacuum of about 30 torr followed by back-filling with nitrogen. After degassing, the flask was back-filled with nitrogen, then 10.2 µL (200 ppm) Ti(O-nBu)$_4$ (obtained from Acros Organics of Geel, Belgium) was added to the flask via microliter pipette. The flask was degassed/backfilled an additional 3 times, followed by back-filling with nitrogen. The flask was placed in an oil bath and the temperature of the oil bath was set to 150° C. and maintained for 14 hours. The temperature of the oil bath was then increased to 180° C. for 45 minutes, followed by 190° C. for 1 hour, then 200° C. for 40 minutes. The pressure in the flask was then decreased to about 15 torr over the next hour and maintained for an additional 22.5 hours. The resulting polymer was analyzed by DSC, and the $T_g$ was found to be 24° C. A small sample was also dissolved in DMF and analyzed by GPC. The polymer was found to have $M_n$=7476, $M_w$=15986, for PDI=2.14.

Example 29

A 250 mL four-neck round bottom flask was charged with 26.83 g (71.7 mmol) EtBLEK, 5.28 g (6.0 mL, 71.2 mmol) 1,3-diaminopropane (obtained from Acros Organics of Geel, Belgium) and 30.3 mg (0.2 mmol, 1000 ppm) 1,3,4,6,7,8-hexahydro-2H-pyrimido[1,2-a]-pyrimidine (TBD, obtained from the Sigma-Aldrich Company of St. Louis, Mo.). The flask was equipped with a mechanical stirrer, Dean-Stark apparatus, and a nitrogen/vacuum inlet. The contents of the flask were degassed with three repetitions of evacuating the flask to approximately 1 torr and back-filling with nitrogen while stirring in an oil bath having a temperature of about 25° C. After degassing was complete, the reaction mixture back-filled with nitrogen and the oil bath was heated to 120° C. The flask was stirred in the oil bath for 15 hours, at which point 1.0 mL of liquid had collected in the Dean-Stark trap and solution viscosity had increased noticeably. Then the temperature of the oil bath was raised to 200° C. over the next about 6 hours and total of 4.2 mL of liquid was observed to collect in the Dean-Stark trap. The Dean Stark trap was emptied and 0.5 torr vacuum applied to the flask at 200° C. for 6 hours. The reaction product was a red transparent solid. The amount of reaction product collected was 16.15 g. The reaction product was analyzed by DSC ($T_g$=76.7° C., ΔH=0.40 J/(g*° C.)).

Example 30

To a 250 mL three-neck flask was charged with 25.10 g (67.0 mmol) EtBLEK and 8.03 g (69.1 mmol) 1,6-hexamethylene diamine (obtained from Acros Organics of Geel, Belgium). The flask was equipped with a mechanical stirrer, Dean Stark apparatus, and nitrogen/vacuum inlet. The flask was degassed at room temperature with three repetitions of evacuating the flask to approximately 1 torr and back-filling with nitrogen. After degassing was completed the flask was back-filled with nitrogen, and the reaction mixture was placed in an oil bath having a temperature set to 190° C., with stirring, and maintained at this temperature for 18 hours, resulting in collection of 7.0 mL of liquid in the Dean Stark trap. The oil bath was then heated to 200° C. and 0.6 g (2.4 mmol) methylene-bis(4,4'-diphenyl) diisocyanate (obtained from the Sigma-Aldrich Company of St. Louis, Mo.) was added dropwise by syringe, resulting in the immediate increase in mixture viscosity to the point where stirring became completely ineffective. The contents of the flask were analyzed by DSC ($T_g$=57.1° C. ΔH=0.38 J/(g*° C.)).

Example 31

A 1 L, 3-neck roundbottom flask was warmed by placing it in an oil bath set to 50° C. The flask was charged with 209.26 g (1.20 mol) dimethyl adipate (obtained from the Sigma-Aldrich Company of St. Louis, Mo.) and 148.01 g (1.27 mol) 1,6 hexamethylenediamine (obtained from the Fluka Chemical Corporation of Milwaukee, Wis.) which was melted prior to its addition to the flask. The flask was equipped with a magnetic stir bar, nitrogen inlet, a Dean-Stark trap, and a nitrogen outlet running to a mineral oil bubbler. Nitrogen flow was commenced and 75 mg (210 ppm) 1,3,4,6,7,8-hexahydro-2H-pyrimido[1,2-a]-pyrimidine (obtained from the Sigma-Aldrich Company of St. Louis, Mo.) was added to the flask. The oil bath in which the flask was immersed was maintained at 50° C. for about 24 hours while under a slow stream of nitrogen and with stirring. Then the flask was removed from the oil bath and approximately 300 mL of deionized water was added to the flask and the contents stirred. The water was then stripped off by placing the contents of the flask into a 1 L single-neck roundbottom flask and placing the flask onto a rotary evaporator at a pressure of 10 torr. The stripped residue was a solid. The residue was placed in a vacuum oven at a temperature of about 60° C. and a pressure of about 10 torr for about 60 hours. After vacuum dried, the residue was not soluble in any common solvents and therefore could not be analyzed by GC, or GPC. An $^1$H-NMR spectrum run in CDCl$_3$/Hexafluoroisopropanol (HFIP) (95:5 v/v) confirmed the presence of a 1:1 adduct of dimethyl adipate and 1,6-hexamethylene diamine, but the presence of very broad peaks suggested that some polymerization may have taken place.

A 250 mL, 3-neck roundbottom flask was charged with 21.15 g (96.9 mmol) EtLGK and 25.10 g (97.1 mmol based on theoretical structure from 1:1 condensation) of the 1:1 adduct of dimethyl adipate and 1,6-hexamethylene diamine. The flask was equipped with a mechanical stirrer, nitrogen inlet, a Dean-Stark trap, and a nitrogen outlet running to a mineral oil bubbler. The flask was placed under a stream of nitrogen and placed in an oil bath set to a temperature of 160° C. The flask was stirred in the oil bath for about 2 hours, at which point the temperature of the oil bath was changed to 180° C., and maintained at this temperature for about 25 minutes. Then the temperature of the oil bath was increased to 200° C., and maintained at this temperature for about 90 minutes. Then the oil bath temperature was increased to 220° C. and maintained at this temperature for about 1 hour; then the temperature of the oil bath was increased to 240° C. After about 30 minutes, 4.7 µL (100 ppm) Ti(O-nBu)$_4$ (obtained from Acros Organics of Geel, Belgium) was added to the flask via metered micropipette; stirring at 240° C. was continued for about 8.5 hours. The heat was then shut off and the reaction cooled to room temperature. The product was an amber solid which contained small, inhomogeneous pieces. The contents of the flask were insoluble in common solvents and were analyzed only by DSC, which showed a $T_g$ of 13° C.

Example 32

A 250 mL, four-neck round bottom flask was charged with 26.06 g (69.6 mmol) EtBLEK and 8.40 g (72.3 mmol) 1,6-hexamethylene diamine (obtained from Acros Organics of Geel, Belgium). The flask was equipped with a mechanical stirrer, Dean Stark trap, and nitrogen/vacuum inlet. The contents of the flask were placed in an oil bath set to a temperature of 50° C. under nitrogen purge for about 16 hours. The contents of the flask were then degassed with three repetitions of evacuating the flask to approximately 1 torr and back-filling with nitrogen. After degassing was complete, the flask was back-filled with nitrogen. Then 6.9 µL (200 ppm) Ti(O-nBu)$_4$ (obtained from Acros Organics) was added to the flask via metered micropipette, and the temperature of the oil bath was increased to 190° C. The contents of the flask were stirred under nitrogen in the oil bath for 21 hours, then the oil bath temperature was increased to 210° C. and a vacuum of 0.5 torr applied to the flask for 7 hours. The flask was then removed from the oil bath and back-filled with nitrogen. A small sample of the contents of the flask were removed and analyzed by DSC, which showed $T_g$=55.1° C., ΔH=0.37 J/(g*° C.).

Example 33

To the flask containing the reaction product of Example 33 was added 12.16 g (70 mmol) dimethyl adipate (obtained from the Sigma-Aldrich Company of St. Louis, Mo.). The contents of the flask were placed in an oil bath set to a temperature of 90° C. and degassed with three repetitions of evacuating the flask to approximately 1 torr and back-filling with nitrogen. After the degassing was completed the flask was back-filled with nitrogen. The contents were stirred and the temperature of the oil bath was increased to 210° C. for one hour. Then the flask was equipped with an addition funnel charged with 7.23 g (62.2 mmol) 1,6-hexamethylene diamine (obtained from Acros Organics of Geel, Belgium). The 1,6-hexamethylene diamine was melted with a heat gun and the contents added dropwise over about 7 hours to the flask. The addition of 1,6-hexamethylene diamine was accompanied by marked increase in solution viscosity and collection of 4.0 mL of liquid in the Dean Stark trap. The oil bath temperature was increased to about 220° C. and a vacuum of about 0.5 torr was applied to the flask for about 3.5 hours, then the temperature of the oil bath was increased to about 240° C. for about 3 hours. Then the flask was removed from the oil bath and was allowed to cool under nitrogen. An opaque amber solid was isolated. The solid was completely insoluble in THF and DMF. DSC analysis of the solid showed $T_g$=47.33° C. (ΔH=0.35 J/(g*° C.)), $T_m$=187.95° C. (ΔH$_f$=17.30 J/g), and $T_c$=168.18° C. (ΔH$_f$=20.26 J/g).

Example 34

A 250 mL four-neck flask was charged with 25.52 g (68.2 mmol) EtBLEK, 14.98 g (74.1 mmol) diethyl adipate (obtained from SAFC® of Lenexa, Kans.), and 15.57 g (134 mmol) 1,6-hexamethylene diamine (obtained from Acros Organics of Geel, Belgium). The flask was equipped with a mechanical stirrer, Dean Stark trap, and nitrogen/vacuum inlet. The contents of the flask were degassed with three repetitions of evacuating the flask to approximately 1 torr and back-filling with nitrogen. After degassing, the flask was back-filled with nitrogen. The contents of the flask were stirred while immersed in an oil bath having a temperature set to 190° C. for 16 hours, leading to the collection of 13.3 mL of liquid in the Dean Stark trap. The temperature of the oil bath was raised to 220° C. and a vacuum of about 1 torr was applied to the flask for about 1 hour, and which point a yellow transparent solid was isolated. DSC analysis revealed $T_g$=34.88° C. (ΔH=0.29 J/(g*° C.)), $T_m$=177.72° C. (ΔH$_f$=36.74 J/g), and $T_c$=126.15° C. (ΔH$_f$=34.46 J/g).

Comparison of the DSC results from Example 34 and Example 35 reveal that controlling the order of addition of reagents, which gives rise to a segmented polymer structure, results in a significant difference in the polymer's thermal properties.

Example 35

A 250 mL round bottom flask was charged with 50.1 g (0.230 mol) of EtLGK and 40.0 g (0.230 mol) of dimethyl adipate (obtained from the Sigma-Aldrich Company of St. Louis, Mo.). The flask was equipped with a mechanical stirrer, nitrogen inlet, and a Dean Stark trap with a nitrogen inlet/outlet. The flask was immersed in an oil bath set to a temperature of 60° C. and the contents of the flask were degassed with 5 cycles of applying a vacuum of about 0.4 torr followed by back-filling with nitrogen. After the degassing was completed the flask was backfilled with nitrogen and a nitrogen sweep through the flask was commenced with stirring, and this was maintained for about 12 hours. At the end of the 12 hours the nitrogen sweep was stopped and the flask placed under a nitrogen blanket (e.g. nitrogen outlet from the flask was closed and the nitrogen flow directed to a bubbler). At this point, 23.4 µl (200 ppm) of titanium tetrabutoxide (obtained from Acros Organics of Geel, Belgium) was injected into the flask by a metered pipette and the flask was stirred for about 10-20 minutes. Then 26.7 g (0.230 mol) of 1,6-hexamethylenediamine (obtained from Acros Organics) was added all at once to the flask. The flask was then degassed again with 3 cycles of vacuum of about 1 torr followed by back-filling with nitrogen.

Figure 6:
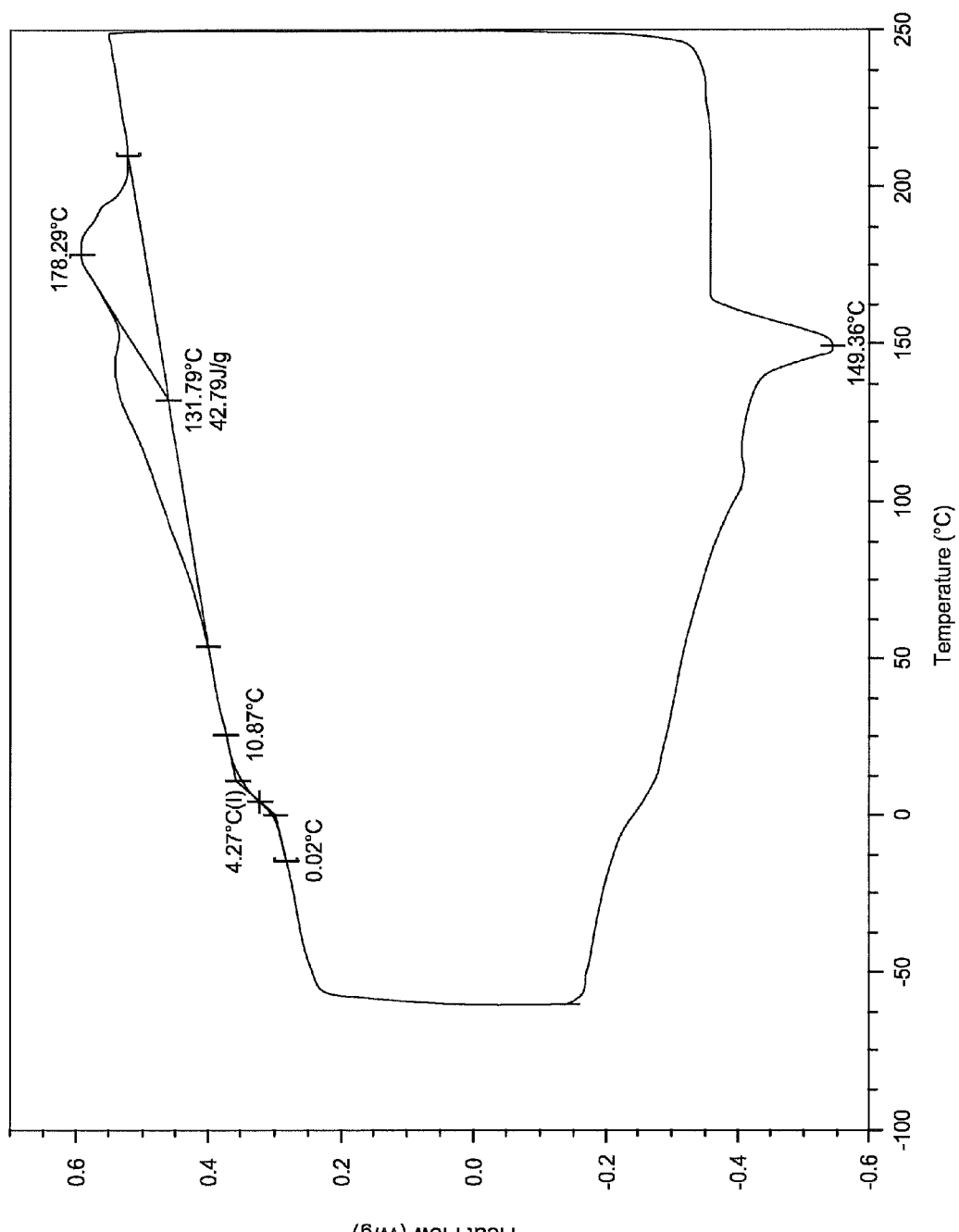
FIG. 6 is a plot of the differential scanning calorimetry measurements for a compound of the invention.

After degassing was complete, the flask was back-filled with nitrogen and the oil bath temperature was set to 190° C. This temperature was maintained for about 2 hours and then the temperature of the oil bath was raised to 200° C. This was maintained for about 2 hours, then the temperature of the oil bath was increased to 210° C. This temperature was maintained for about 30 minutes, then the temperature of the oil bath was increased to 220° C. After about 1 hour at 220° C. a vacuum was applied to the flask. The vacuum was observed to go from about 45 torr to about 8 torr over about 15 hours. At this point a high vacuum was applied to the flask and the pressure in the flask was observed to be about 0.5 torr, this vacuum was maintained for about 8 hours. At this point the flask was open under a rapid nitrogen flow and a small sample removed for analysis by DSC. The DSC showed that the product of the reaction had glass transition temperature ($T_g$) of about 4.3° C. and a melt temperature of about 178.3° C. During the cooling cycle, recrystallization was observed with a strong peak at about 148.7° C. The DSC trace for the sample is shown in FIG. 6.

Example 36

A 250 mL, 3-neck roundbottom flask was charged with 26.02 g (119 mmol) EtLGK and 13.75 g (118 mmol) 1,6-hexamethylene diamine (obtained from the Fluka Chemical Corporation of Milwaukee, Wis.). The flask was equipped with a mechanical stirrer, nitrogen inlet, a Dean-Stark trap, and a nitrogen outlet running to a mineral oil bubbler. The flask was placed under nitrogen and placed in an oil bath. The oil bath was set to 175° C., and maintained for about 16.5 hours. A small sample of the contents of the flask was removed for analysis.

Figure 7:
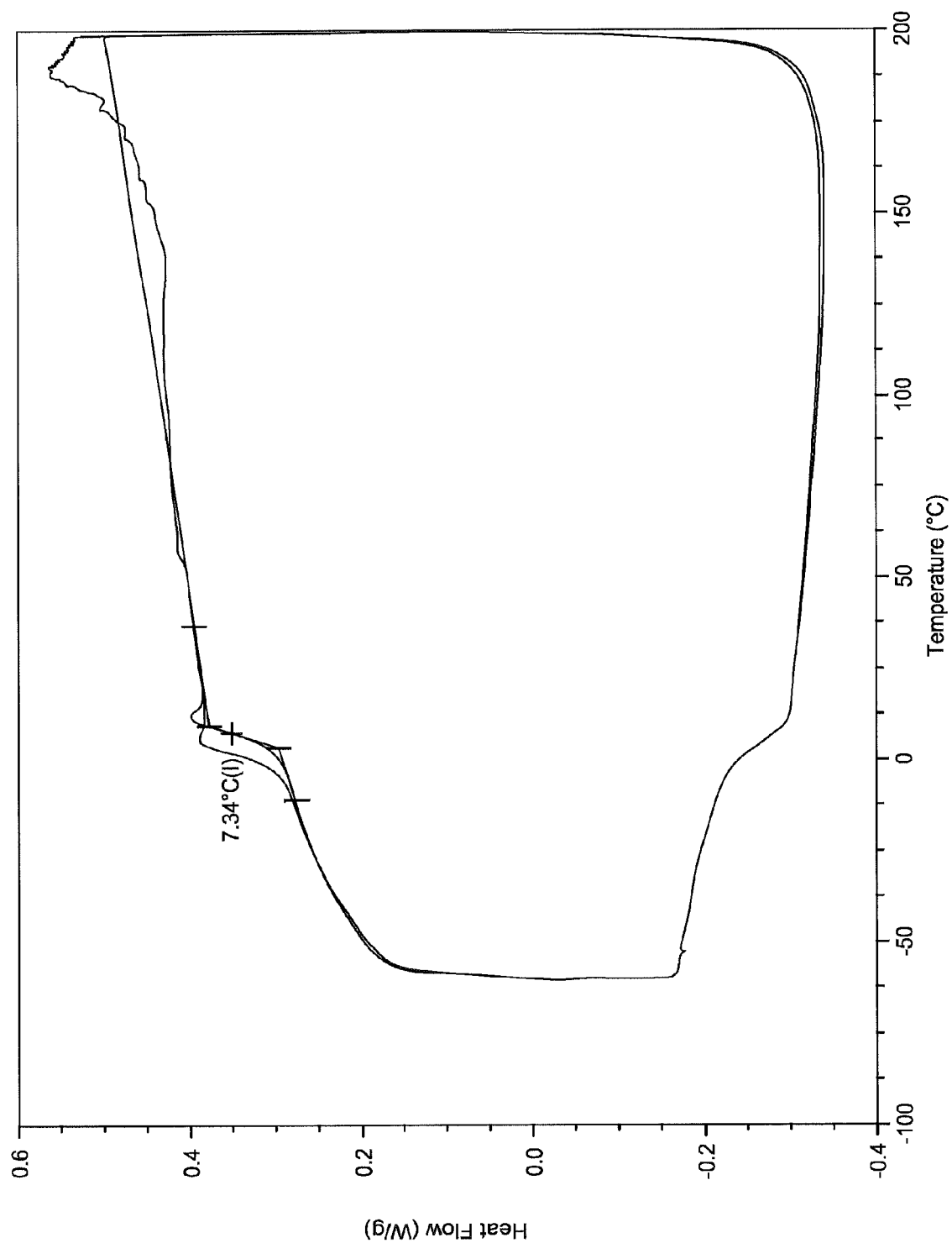
FIG. 7 is a plot of the differential scanning calorimetry measurements for a compound of the invention.

The oil bath was cooled to 75° C., and 20.54 g (118 mmol) dimethyl adipate (obtained from the Sigma-Aldrich Company of St. Louis, Mo.) was added to the flask. After 1 hour, the temperature was increased to 180° C. over the next three hours and then maintained for another 3.5 hours. The oil bath was then allowed to cool to 120° C., and 12.2 µL (200 ppm) Ti(O-nBu)$_4$ (obtained from Acros Organics of Geel, Belgium) was added to the flask. The temperature of the oil bath was then increased to 200° C., and maintained at this temperature for about 15 hours. The pressure in the flask was then reduced to about 10 torr, and maintained for 90 minutes, at which point the pressure was further reduced to about 5 torr, and maintained for approximately 4 hours. The flask was backfilled with nitrogen and allowed to cool to room temperature. The reaction product was rubbery and dark, and was analyzed by GPC and DSC. The GPC showed that $M_n$=1761, $M_w$=2610, and PDI=1.48. The DSC result showed that the polymer had a $T_g$ of approximately 7° C. and no crystalline transition. The DSC plot is shown in FIG. 7. By comparing the DSC results of Example 35 with this Example, it can be seen that affecting the degree of segmentation of the polymer by affecting the order of addition of reagents has a profound effect on the ability of the resulting polymer to form crystalline structure.

A sample of the reaction product was analyzed by $^1$H NMR (DMSO-d$_6$). The NMR was consistent with a proportion of monomer fragments corresponding to two EtLGK molecules condensed with one mole of diamine (e.g. the bis(ketal amide)).

Example 37

A 250 mL four-neck flask was charged with 23.3 g (62.2 mmol) EtBLEK, 8.2 g (132.1 mmol) ethylene glycol (obtained from Fisher Scientific of Waltham, Mass.), 5.30 g (61.5 mmol) piperazine (obtained from Sigma-Aldrich Company of St. Louis, Mo.), and 35.7 mg (0.26 mmol) 1,3,4,6,7,8-hexahydro-2H-pyrimido[1,2-a]-pyrimidine (obtained from the Sigma-Aldrich Company). The flask was equipped with a mechanical stirrer, Dean Stark trap. The contents of the flask were degassed at room temperature with three repetitions of evacuating the flask to approximately 1 torr, then back-filling with nitrogen. After degassing was complete the flask was back-filled with nitrogen. The reaction mixture was placed in an oil bath having a temperature set to 120° C. and stirred for 16 hours, leading to collection of 1.0 mL of liquid in the Dean Stark trap. The temperature was raised to 200° C. over 7 hours, leading to a total of 6.5 mL of liquid collected in the Dean Stark trap. The trap was drained and 1 torr vacuum was applied for 7 hours at 220° C., leading to collection of an additional 6.9 mL of liquid. The flask was back-filled with nitrogen and allowed to cool, resulting in the collection of 15.60 g of a dark red solid. DSC analysis of the solid revealed $T_g$=58.05° C. ($\Delta H$=0.41 J/(g*° C.)).

Example 38

A 250 mL, 3-neck roundbottom flask was charged with 39.40 g (181 mmol) EtLGK, 34.99 g (180 mmol) dimethyl terephthalate (DMT, obtained from the Sigma-Aldrich Company of St. Louis, Mo.) and 11.15 g (183 mmol) 2-aminoethanol (obtained from TCI America of Portland, Oreg.). The flask was equipped with a mechanical stirrer, Dean-Stark trap and condenser, and a nitrogen inlet/outlet. The contents of the flask were degassed with three repetitions of evacuating the flask to approximately 20 torr and back-filling with nitrogen. After degassing, the flask was back-filled with nitrogen. Then the flask was briefly opened and 17.3 µL (about 200 ppm) of Ti(O-nBu)$_4$ (obtained from Acros Organics of Geel Belgium), was added to the flask, followed by degassing with three repetitions of evacuating the flask to approximately 20 torr and back-filling with nitrogen. After degassing, the flask was back-filled with nitrogen.

The flask was placed, with stirring, in an oil bath having a temperature set to 150° C. The flask was maintained at these conditions for approximately 2.5 hours, and then the temperature of the oil bath was increased to 190° C. for 17 hours. The pressure in the flask was then reduced to approximately 35 torr, and the temperature of the oil bath was increased to 210° C. After 2.5 hours, the pressure was further reduced to approximately 1 torr, and these conditions maintained for approximately 10 hours. The flask was then backfilled with nitrogen and removed from the oil bath and allowed to cool to room temperature. The crude reaction product was analyzed by GPC (DMF solvent) and DSC. The reaction product was not completely soluble in DMF and was filtered using a 0.45 µm PTFE filter prior to analysis in order to remove the insoluble portions. The GPC data for the DMF-soluble fraction showed $M_n$=6617, $M_w$=39226, PDI=5.93. The DSC data showed that the reaction product had a $T_g$ of 62° C.

Comparison of this Example to the results obtained in Example 26 shows that a narrower polydispersity index (PDI) is obtained, in this embodiment of the invention, by controlling the order of addition of the reagents and thereby the morphology of the resulting reaction product.

The present invention may suitably comprise, consist of, or consist essentially of, any of the disclosed or recited elements. The invention illustratively disclosed herein can be suitably practiced in the absence of any element which is not specifically disclosed herein. The various embodiments described above are provided by way of illustration only and should not be construed to limit the claims attached hereto. It will be recognized that various modifications and changes may be made without following the example embodiments and applications illustrated and described herein, and without departing from the true spirit and scope of the following claims.

The invention claimed is:

1. A compound comprising one or more fragments having structure V:

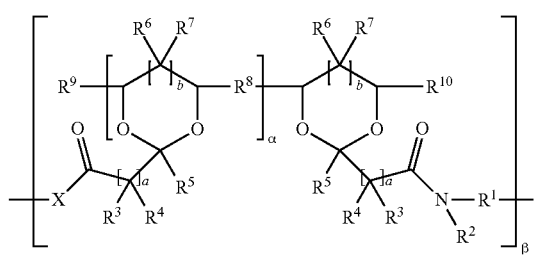

wherein

α is an integer of at least 1;

β is an integer of at least 1;

each X is independently O or NR$^2$—;

each R$^1$ is independently a linear, branched, or cyclic alkyl, a linear, branched, or cyclic alkenyl, alkynyl, aryl, or alkaryl group, optionally comprising one or more heteroatoms; each R$^2$ is independently hydrogen or an alkyl group having between 1 and 6 carbon atoms, or a portion of a piperazine moiety wherein X is NR$^2$;

each R$^3$, R$^4$, R$^5$, R$^6$, and R$^7$ is independently hydrogen, a linear, branched, or cyclic alkyl, a linear, branched, or cyclic alkenyl, alkynyl, aryl, or alkaryl group, optionally comprising one or more hetero atoms;

each R$^8$ is independently a covalent bond, methylene, ethylene, or hydroxymethylene;

R$^9$ and R$^{10}$ are independently hydrogen, a linear, branched, or cyclic alkyl, a linear, branched, or cyclic alkenyl, alkynyl, aryl, alkaryl, or a polymeric moiety; and optionally comprises one or more heteroatoms;

each a is independently 0 or an integer of 1 to 12; and each b is independently 0 or 1, wherein b=0 indicates a five membered ring:

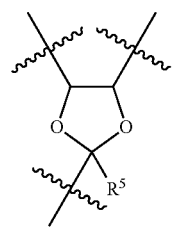

and b=1 indicates a 6 membered ring:

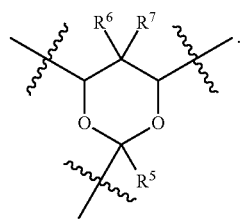

2. A compound comprising one or more fragments having structure V':

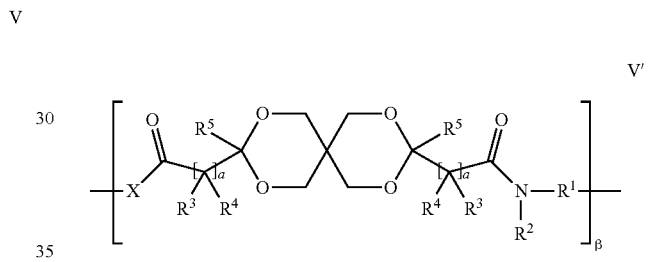

wherein

β is an integer of at least 1;

each X is O;

each a is independently 0 or an integer of 1 to 12;

each R$^1$ is independently a linear, branched, or cyclic alkyl, a linear, branched, or cyclic alkenyl, alkynyl, aryl, or alkaryl group, optionally comprising one or more heteroatoms;

each R$^2$ is independently hydrogen or an alkyl group having between 1 and 6 carbon atoms, or a portion of a piperazine moiety wherein X is NR$^2$; and each R$^3$, R$^4$, and R$^5$ is independently hydrogen, a linear, branched, or cyclic alkyl, a linear, branched, or cyclic alkenyl, alkynyl, aryl, or alkaryl group, optionally comprising one or more heteroatoms.

3. The compound of claim 1, wherein a is 0, 1 or 2.

4. The compound of claim 1, wherein a is 2 and all R$^3$ and R$^4$ are hydrogen.

5. The compound of claim 4, wherein R1 is 1,2-cyclohexyl, —(CH$_2$)$_3$—, or —(CH$_2$)$_6$—.

6. The compound of claim 1, wherein β is 1.

7. The compound of claim 1, wherein β is between about 2 and about 500.

8. A formulation comprising the compound of claim 1.

9. An article comprising the compound of claim 1.

10. The article of claim 9, wherein the article is transparent.

11. A film comprising the compound of claim 1.

12. An injection-molded product comprising the compound of claim 1.

13. An extrusion coated product comprising the compound of claim 1.

14. A fiber comprising the compound of claim 1.

15. A foam comprising the compound of claim 1.

16. A thermoformed product comprising the compound of claim 1.

17. An extruded profile or sheet comprising the compound of claim 1.

18. A coating comprising the compound of claim 1.

19. The coating of claim 18, wherein the coating is a paint, adhesive, or glue.

20. A polymer blend comprising the compound of claim 1 and an aromatic/aliphatic polyester, a biodegradable polyester, a polystyrene, a copolymer of polystyrene, a polyurethane, a polycarbonate, a polyamide, or a polyolefin.

21. A polymer blend comprising the compound of claim 1 and a starch, cellulose, chitosan, alginate, natural rubber, or natural fiber.

22. A polymer alloy comprising the compound of claim 1 and a polyamide polymer or a polyamide copolymer.

23. The compound of claim 2, wherein a is 0, 1 or 2.

24. The compound of claim 2, wherein all $R^2$ and $R^3$ are hydrogen.

25. The compound of claim 24, wherein $R^1$ is 1,2-cyclohexyl, $-(CH_2)_3-$, or $-(CH_2)_6-$.

26. The compound of claim 2, wherein β is 1.

27. The compound of claim 2, wherein 0 is between about 2 and about 500.

28. A formulation comprising the compound of claim 2.

29. An article comprising the compound of claim 2.

30. The article of claim 29, wherein the article is transparent.

31. A film comprising the compound of claim 3.

32. An injection-molded product comprising the compound of claim 2.

33. An extrusion coated product comprising the compound of claim 2.

34. A fiber comprising the compound of claim 2.

35. A foam comprising the compound of claim 2.

36. A thermoformed product comprising the compound of claim 2.

37. An extruded profile or sheet comprising the compound of claim 2.

38. A coating comprising the compound of claim 2.

39. The coating of claim 38, wherein the coating is a paint, adhesive, or glue.

40. A polymer blend comprising the compound of claim 2 and an aromatic/aliphatic polyester, a biodegradable polyester, a polystyrene, a copolymer of polystyrene, a polyurethane, a polycarbonate, a polyamide, or a polyolefin.

41. A polymer blend comprising the compound of claim 2 and a starch, cellulose, chitosan, alginate, natural rubber, or natural fiber.

42. A polymer alloy comprising the compound of claim 2 and a polyamide polymer or a polyamide copolymer.

* * * * *